(12) United States Patent
Albrecht et al.

(10) Patent No.: US 11,529,347 B2
(45) Date of Patent: Dec. 20, 2022

(54) SHP2 PHOSPHATASE INHIBITORS AND METHODS OF USE THEREOF

(71) Applicants: Relay Therapeutics, Inc., Cambridge, MA (US); D. E. Shaw Research, LLC, New York, NY (US)

(72) Inventors: Brian K. Albrecht, Cambridge, MA (US); Fabrizio Giordanetto, New York, NY (US); Jack Benjamin Greisman, New York, NY (US); Paul Maragakis, New York, NY (US); Alexander M. Taylor, Cambridge, MA (US); W. Patrick Walters, Westborough, MA (US)

(73) Assignees: Relay Therapeutics, Inc., Cambridge, MA (US); D. E. Shaw Research, LLC, New York, NY (US)

( * ) Notice: Subject to any disclaimer, the term of this patent is extended or adjusted under 35 U.S.C. 154(b) by 0 days.

(21) Appl. No.: 16/335,933

(22) PCT Filed: Sep. 22, 2017

(86) PCT No.: PCT/US2017/052950
§ 371 (c)(1),
(2) Date: Mar. 22, 2019

(87) PCT Pub. No.: WO2018/057884
PCT Pub. Date: Mar. 29, 2018

(65) Prior Publication Data
US 2019/0307745 A1    Oct. 10, 2019

Related U.S. Application Data

(60) Provisional application No. 62/398,100, filed on Sep. 22, 2016.

(51) Int. Cl.
| | |
|---|---|
| *A61K 31/4985* | (2006.01) |
| *A61K 31/55* | (2006.01) |
| *C07D 487/04* | (2006.01) |
| *C07D 519/00* | (2006.01) |
| *C07D 498/10* | (2006.01) |

(52) U.S. Cl.
CPC .......... *A61K 31/4985* (2013.01); *A61K 31/55* (2013.01); *C07D 487/04* (2013.01); *C07D 498/10* (2013.01); *C07D 519/00* (2013.01)

(58) Field of Classification Search
CPC .................................................. C07D 487/04
See application file for complete search history.

(56) References Cited

U.S. PATENT DOCUMENTS

| | | | |
|---|---|---|---|
| 10,280,171 B2 * | 5/2019 | Jones | A61K 31/4985 |
| 10,934,302 B1 | 3/2021 | Taylor et al. | |
| 2011/0130396 A1 | 6/2011 | Hoelzemann et al. | |
| 2017/0001975 A1 | 1/2017 | Chen et al. | |
| 2017/0015680 A1 | 1/2017 | Chen et al. | |
| 2017/0204080 A1 | 7/2017 | Chen et al. | |

(Continued)

FOREIGN PATENT DOCUMENTS

| | | |
|---|---|---|
| CN | 107286150 A | 10/2017 |
| CN | 110143949 A | 8/2019 |

(Continued)

OTHER PUBLICATIONS

Bollu et al. Clin Cancer Res. May 1, 2017; 23(9): 2136-2142. (Year: 2017).*

(Continued)

*Primary Examiner* — Erich A Leeser
(74) *Attorney, Agent, or Firm* — Alston & Bird LLP

(57) ABSTRACT

The present invention relates to novel compounds having the general formula:

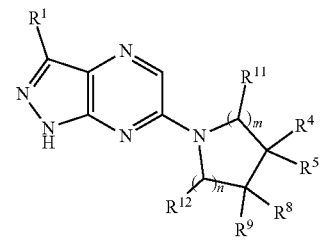

and pharmaceutical compositions thereof, and methods for inhibiting the activity of SHP2 phosphatase with the compounds and compositions of the invention. The present invention further relates to, but is not limited to, methods for suppressing tumor cell growth, ameliorating the pathogenesis of systemic lupus erythematosus, and the treatment of various other disorders, including Noonan syndrome, diabetes, neutropenia, neuroblastoma, melanoma, juvenile leukemia, juvenile myelomonocytic leukemia, chronic myelomonocytic leukemia, acute myeloid leukemia, and other cancers associated with SHP2 deregulation with the compounds and compositions of the invention, alone or in combination with other treatments. Other cancers associated with SHP2 deregulation include HER2-positive breast cancer, triple-negative breast cancer, ductal carcinoma of the breast, invasive ductal carcinoma of the breast, non-small cell lung cancer, esophageal cancer, gastric cancer, squamous-cell carcinoma of the head and neck (SCCHN), and colon cancer.

8 Claims, No Drawings

(56) References Cited

U.S. PATENT DOCUMENTS

| | | | |
|---|---|---|---|
| 2017/0342078 A1* | 11/2017 | Jones | A61K 31/4985 |
| 2018/0186770 A1 | 7/2018 | Chen et al. | |
| 2018/0251471 A1 | 9/2018 | Chen et al. | |
| 2019/0077792 A1 | 3/2019 | Volkmann et al. | |
| 2019/0127378 A1 | 5/2019 | Ma et al. | |
| 2019/0185475 A1 | 6/2019 | Bagdanoff et al. | |
| 2019/0210977 A1 | 7/2019 | Jogalekar et al. | |
| 2019/0270746 A1 | 9/2019 | Jones et al. | |
| 2019/0290649 A1 | 9/2019 | Xie et al. | |
| 2019/0307745 A1 | 10/2019 | Albrecht et al. | |
| 2019/0389867 A1 | 12/2019 | Jones et al. | |
| 2020/0002330 A1 | 1/2020 | Chen et al. | |
| 2020/0017511 A1 | 1/2020 | Blank et al. | |
| 2020/0017517 A1 | 1/2020 | Gill et al. | |
| 2020/0048249 A1 | 2/2020 | Jones et al. | |
| 2020/0062760 A1 | 2/2020 | Giordanetto et al. | |
| 2020/0108071 A1 | 4/2020 | Chin et al. | |
| 2020/0115389 A1 | 4/2020 | Fu et al. | |
| 2020/0172546 A1 | 6/2020 | Taylor et al. | |
| 2020/0253969 A1 | 8/2020 | Taylor et al. | |
| 2020/0392161 A1 | 12/2020 | Walters et al. | |
| 2021/0069188 A1 | 3/2021 | Taylor et al. | |
| 2021/0085677 A1 | 3/2021 | Taylor et al. | |

FOREIGN PATENT DOCUMENTS

| | | |
|---|---|---|
| CN | 111153899 | 5/2020 |
| TW | 201925186 A | 7/2019 |
| WO | WO-2004/111060 A1 | 12/2004 |
| WO | WO-2020076723 A1 | 1/2007 |
| WO | WO-2010/011666 A2 | 1/2010 |
| WO | WO-2010/097798 A1 | 9/2010 |
| WO | WO-2010/121212 A2 | 10/2010 |
| WO | WO-2011/130396 A1 | 10/2011 |
| WO | WO 2015/107493 A1 | 7/2015 |
| WO | WO-2015/107494 A1 | 7/2015 |
| WO | WO-2015/107495 A1 | 7/2015 |
| WO | WO-2016/203404 A1 | 12/2016 |
| WO | WO-2016/203406 A1 | 12/2016 |
| WO | WO-2017156397 A1 | 9/2017 |
| WO | WO-2017/210134 A1 | 12/2017 |
| WO | WO-2017/211303 A1 | 12/2017 |
| WO | WO-2018/013597 A1 | 1/2018 |
| WO | WO-2018/057884 A1 | 3/2018 |
| WO | WO-2018/081091 A1 | 5/2018 |
| WO | WO-2018/172984 A1 | 9/2018 |
| WO | WO-2018/218133 A1 | 11/2018 |
| WO | WO-2019051084 A1 | 3/2019 |
| WO | WO-2019/067843 A1 | 4/2019 |
| WO | WO-2019/075265 A1 | 4/2019 |
| WO | WO-2019118909 A1 | 6/2019 |
| WO | WO-2019/165073 A1 | 8/2019 |
| WO | WO-2019158019 A1 | 8/2019 |
| WO | WO-2019/183364 A1 | 9/2019 |
| WO | WO-2019/183367 A1 | 9/2019 |
| WO | WO-2019167000 A1 | 9/2019 |
| WO | WO-2019199792 A1 | 10/2019 |
| WO | WO-2019233810 A1 | 12/2019 |
| WO | WO-2020022323 A1 | 1/2020 |
| WO | WO-2020063760 A1 | 4/2020 |
| WO | WO-2020065452 A1 | 4/2020 |
| WO | WO-2020065453 A1 | 4/2020 |
| WO | WO-2020073945 A1 | 4/2020 |
| WO | WO-2020073949 A1 | 4/2020 |
| WO | WO-2020081848 A1 | 4/2020 |
| WO | WO-2020094018 A1 | 5/2020 |
| WO | WO-2020094104 A1 | 5/2020 |

OTHER PUBLICATIONS

Lazo et al. SLAS Discovery 2017, vol. 22(9) 1071-1083 (Year: 2017).*

Jones et al. Provisional U.S. Appl. No. 62/343,455, filed May 31, 2016. (Year: 2016).*

U.S. Appl. No. 16/344,061, dated Mar. 22, 2019.

Chloe, Copin et al. "Snar Versus Buchwald-Hartwig Amination/ Amidation in the Imidazo[2,1-b] [1,3,4]thiadiazole Series," European Journal of Organic Chemistry, vol. 2015, No. 31, Sep. 29, 2015, pp. 6932-6942.

Larochelle, Jonathan et al. "Identification of An Allosteric Benzothiazolopyrimidone Inhibitor of the Oncogenic Protein Tyrosine Phosphatase SHP2," Bioorganic & Medicinal Chemistry, vol. 25, No. 24, Oct. 20, 2017, pp. 6479-6485.

Temple, Kayla et al. "Identification of the Minimum PAR4 Inhibitor Pharmacophore and Optimization of a Series of 2-Methoxy-6-Arylimidazo[2,1-b][1,3,4]Thiadiazoles," Bioorganic & Medicinal Chemistry Letters, Pergamon, Amsterdam, NL, vol. 26, No. 22, 11 Oct. 11, 2016, pp. 5481-5486.

Yokoi, Taiyo et al. "Quantitative Structure-Activity Relationship of Substituted Imidazothiadiazoles for Their Binding Against the Ecdysone Receptor of Sf-9 Cells," Bioorganic & Medicinal Chemistry Letters, vol. 27, No. 23, Oct. 13, 2017, pp. 5305-5309.

Saifidin, Safarov et al. "Preparation of 5-Bromo-6-phenylimidazo(2,1-b)(1,3,4)thiadiazol-2-ylamines," Journal of Heterocyclic Chemistry, Wiley-Blackwell Publishing, Inc, Us, vol. 45, No. 1, Jan. 1, 2008, pp. 299-302.

Krasavin M et al. "Tert-Butyl Isocyanide Revisited as a Convertible Reagent in the Groebke-Blackburn Reaction," Tetrahedron Letters, Elsevier, Amsterdam, NL, vol. 49, No. 51, Dec. 15, 2008, pp. 7318-7321.

Shen, Jiayi et al. "3-Aminopyrazolopyrazine Derivatives as Spleen Tyrosine Kinase Inhibitors," Hemical Biology & Drug Design, vol. 88, No. 5, 2016, pp. 690-698.

Jorge, Fortanet et al. "Allosteric Inhibition of SHP2: Identification of a Potent, Selective, and Orally Efficacious Phosphatase Inhibitor," J. Med. Chem. 2016, 59, 17, pp. 7773-7782.

U.S. Appl. No. 16/616,361, dated Nov. 22, 2019.

International Search Report and Written Opinion for International Patent Application PCT/US2019/023389 dated May 10, 2019 (12 pages).

U.S. Appl. No. 16/651,733, dated Mar. 27, 2020.

Hellmuth et al., Specific inhibitors of the protein tyrosine phosphatase Shp2 identified by high-throughput docking, PNAS, 105(20), 7275-7280, (2008).

Horig et ai., "From bench to clinic and back: Perspective on the 1st IQPC Translational Research Conference" Journal of Translational Medicine, 2, 44, (Dec. 2004).

Schafer et al., "Failure is an option: learning from unsuccessful proof-of-concept trials," Drug Discovery Today, 13, 913-916, (Nov. 2018).

U.S. Appl. No. 16/355,661, Non-Final Office Action dated Feb. 19, 2021.

U.S. Appl. No. 16/355,661, Requirement for Restriction/Election dated Jul. 31, 2020.

U.S. Appl. No. 16/616,361, Requirement for Restriction/Election dated Oct. 30, 2020.

U.S. Appl. No. 16/886,105, Notice of Allowance dated Sep. 9, 2020.

U.S. Appl. No. 16/886,105, Notice of Allowance dated Nov. 4, 2020.

WIPO Application No. PCT/US2017/052950, PCT International Preliminary Report on Patentability dated Mar. 26, 2019.

WIPO Appiication No. PCT/US2017/052950, PCT International Search Report and Written Opinion of the International Searching Authority dated Mar. 29, 2018.

WIPO Appiication No. PCT/US2017/058048, PCT International Preliminary Report on Patentability dated Apr. 30, 2019.

WIPO Appiication No. PCT/US2017/058048, PCT International Search Report and Written Opinion of the International Searching Authority mailed May 3, 2018.

WIPO Appiication No. PCT/US2018/034614, PCT International Preliminary Report on Patentability dated Nov. 26, 2019.

WIPO Appiication No. PCT/US2018/034614, PCT International Search Report and Written Opinion of the International Searching Authority dated Nov. 29, 2018.

WIPO Application No. PCT/US2018/053322, PCT International Preliminary Report on Patentability dated Mar. 31, 2020.

(56) References Cited

OTHER PUBLICATIONS

WIPO Application No. PCT/US2108/053322, PCT International Search Report and Written Opinion of the International Searching Authority dated Apr. 4, 2019.
WIPO Application No. PCT/US2019/023389, PCT International Preliminary Report on Patentability dated Sep. 22, 2020.
WIPO Application No. PCT/US2020/052118, PCT International Search Report and Written Opinion of the International Searching Authority dated Dec. 14, 2020.
Hackam, et al., "Translation of Research Evidence from Animals to Humans," JAMA, 296(14):1731 -1732, (2006).
Jordan, V.C., "Tamoxifen: A Most Unlikely Pioneering Medicine," Nature Reviews: Drug Discovery, 2:205-213, (2003).
U.S. Appl. No. 16/616,361, Non-Final Office Action dated May 13, 2021.
U.S. Appl. No. 16/651,733, Non-Final Office Action dated Jul. 23, 2021.
Aceto, N. et al., "Tyrosine phosphatase SHP2 promotes breast cancer progression and maintains tumor-initiating cells via activation of key transcription factors and a positive feedback signaling loop," Nature Medicine, 18(4):529-538, (2012).
Gould, P.L., "Salt selection for basic drugs," Int J. Pharmaceutics, 33:201-217, (1986).
Grossman, K.S. et al., "The tyrosine phosphatase Shp2 in development and cancer," Adv. Cancer Res., 106:53-89, (2010).
Bentires-Alj, M. et al., "Activating Mutations of the Noonan Syndrome-Associated SHP2/PTPN11 Gene in Human Solid Tumors and Adult Acute Myelogenous Leukemia," Cancer Res., 64:8816-8820, (2004).
Berge, et al., "Pharmaceutical Salts," J. Pharm. Sci., 66(1):1, (1977).
Cai, P. et al., "Expression and clinical significance of tyrosine phosphatase SHP-2 in colon cancer," Biomedicine & Pharmacotherapy, 68:285-290, (2014).
Chen, Y.-N.P. et al., "Allosteric inhibition of SHP2 phosphatase inhibits cancers driven by receptor tyrosine kinases," Nature, 535:158-152, (2016).
Furcht, C.M. et al., "Diminished functional role and altered localization of SHP2 in non-small cell lung cancer cells with EGFR-activating mutations," Oncogene, 32:2346-2355, (2013).
Schneeberger, V.E. et al., "Inhibition of Shp2 suppresses mutant EGFR-induced iung tumors in transgenic mouse model of lung adenocarcinoma," Oncotarget, 6:6191-6202, (2015).
Wang, J. et al., "Inhibition of SHP2 ameliorates the pathogenesis of systemic lupus erythematosus," The Journal of Clinical Invest. 126:2077-2092, (2016).

* cited by examiner

SHP2 PHOSPHATASE INHIBITORS AND METHODS OF USE THEREOF

CROSS REFERENCE TO RELATED APPLICATIONS

This application is a national stage filing under 35 U.S.C. § 371 of PCT/US2017/052950, filed Sep. 22, 2017, which claims the benefit of, and priority to, U.S. Provisional Patent Application No. 62/398,100, filed Sep. 22, 2016, the contents of each of which are hereby incorporated by reference in their entirety.

FIELD OF THE INVENTION

The present invention relates to novel compounds and pharmaceutical compositions thereof, and methods for inhibiting the activity of SHP2 phosphatase with the compounds and compositions of the invention. The present invention further relates to, but is not limited to, methods for suppressing tumor cell growth, ameliorating the pathogenesis of systemic lupus erythematosus, and the treatment of various other disorders, including, e.g., Noonan syndrome (NS), Leopard Syndrome, diabetes, neutropenia (Kostmann's syndrome), neuroblastoma, melanoma, juvenile leukemia, juvenile myelomonocytic leukemia (JMML), chronic myelomonocytic leukemia, acute myeloid leukemia, and other cancers associated with SHP2 deregulation with the compounds and compositions of the invention, alone or in combination with other treatments. Other cancers associated with SHP2 deregulation include HER2-positive breast cancer, triple-negative breast cancer, ductal carcinoma of the breast, invasive ductal carcinoma of the breast, non-small cell lung cancer (including adenocarcinoma of the lung), esophageal cancer, gastric cancer, squamous-cell carcinoma of the head and neck (SCCHN), and colon cancer. (See, e.g, N. Aceto et al. *Nature Medicine,* 2012, 28, 529-538; C. M. Furcht et al. *Oncogene,* 2013, 32, 2346-2355; V. E. Schneeberger et al. *Oncotarget,* 2015, 6, 6191-6202; P. Cai et al., *Biomedicine & Pharmacotherapy* 2014, 68, 285-290; and references cited therein; each of which hereby incorporated by reference in its entirety).

BACKGROUND OF THE INVENTION

Cellular biological activities are tightly regulated through cellular signal-transduction pathways. Activation of different signaling pathways leads to diverse physiological responses, such as cell proliferation, death, differentiation, and metabolism. The extracellular signals received by cells must be transmitted effectively into the cell to ensure an appropriate response. The impairment of intracellular signaling pathways can result in malfunctioning cells, eventually leading to disorders such as cancer, infectious diseases, inflammation, arteriosclerosis, arthritis, and neurodegenerative diseases.

Many important cellular activities are highly controlled by the cellular signal transduction processes in which protein phosphorylation and dephosphorylation are central events. Protein tyrosine phosphatases (PTP), which remove phosphate groups from tyrosine phosphorylated signaling molecules, play an important role transducing signal flow and controlling cellular behavior.

Src homology region 2 (SH2)-containing protein tyrosine phosphatase 2 (SHP2) is a protein tyrosine phosphatase encoded by the PTPN11 gene. SHP2 contains two Src homology 2 (SH2) $NH_2$-terminal domains and a C-terminal protein-tyrosine phosphatase domain. It is ubiquitously expressed in various tissues and cell types. SHP2 plays an important role in diverse signaling pathways to regulate cellular biological processes and is involved in the signaling pathways of a variety of growth factors and cytokines. Within a single signaling pathway, SHP2 can play both positive (signal enhancing) and negative (signal diminishing) roles in intracellular signaling processes. SHP2 is believed to function by dephosphorylating its associated signaling molecules, thereby attenuating the local signaling flow. However, the main effect of SHP2 action in most signaling pathways (e.g., growth factor, cytokine, and extracellular matrix receptors) is to enhance signal transduction. For example, SHP2 is a positive regulator of the ERK/MAPK signaling pathway, playing a key role in regulating cellular proliferation and survival. (For a review of SHP2 phosphatase, see, e.g, K. S. Grossman et al., *Adv. Cancer Res.* 2010, 106, 53-89; and references cited therein; each of which hereby incorporated by reference in its entirety.)

In the basal state, SHP2 is normally auto-inhibited due to intramolecular interactions between its N-terminal SH2 (N-SH2) domain and its catalytic (PTP) domain, which blocks access to the catalytic site. Activating proteins that interact with the SH2 domains induce a conformational change that reverses this inhibition and allows substrate access to the catalytic site. Mutations in the PTPN11 gene that affect the N-SH2 or PTP domain residues involved in basal inhibition of SHP2 result in more readily activatable forms of SHP2 protein, which can lead to unregulated or increased SHP2 activity. Such activated mutants of SHP2 have been associated with developmental disorders such as Noonan syndrome, where nearly all mutated forms of SHP2 demonstrate increased PTP activity. Activating SHP2 mutations have also been detected in juvenile myelomonocytic leukemia (e.g., Q506P), chronic myelomonocytic leukemia (e.g., Y63C), neuroblastoma (e.g., T507K), melanoma (e.g., R138Q), acute myeloid leukemia (e.g., G503V), breast cancer, lung cancer (e.g., E76V), colorectal cancer (e.g., E76G). (M. Bentires-Alj et al., in *Cancer Res.* 2004, 64, 8816-8820; and references cited therein; each of which hereby incorporated by reference in its entirety). Additional PTPN11 mutations associated with cancers are disclosed in WO 2015/107495; and references cited therein; each of which hereby incorporated by reference in its entirety. Thus, there is a need for SHP2 phosphatase inhibitor compounds and methods for treating cancer with said compounds.

SUMMARY

It is understood that any of the embodiments described below can be combined in any desired way, and that any embodiment or combination of embodiments can be applied to each of the aspects described below, unless the context indicates otherwise.

In one aspect, the invention provides a compound of Formula (I), or a pharmaceutically acceptable salt thereof,

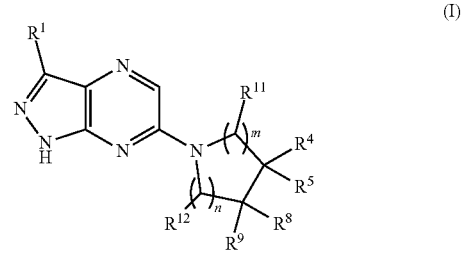

wherein $R^1$ is a 5-10 membered monocyclic or bicyclic aryl or heteroaryl, which is optionally substituted with one or more substituents selected from the group consisting of —$R^{10}$, —$OR^{10}$, —$SR^{10}$, —$N(R^{10})_2$, —$OSO_2R^{10}$, —$SO_2R^{10}$, —$C(O)N(R^{10})_2$, halogen, or nitrile, wherein each $R^{10}$ is, independently, H, —$(C_1$-$C_6)$alkyl, —$(C_1$-$C_6)$haloalkyl, or —$(C_1$-$C_6)$heterocycloalkyl;

each of $R^4$ and $R^5$ is, independently, H, —OH, —$(C_1$-$C_6)$alkyl, —$O(C_1$-$C_6)$alkyl, —$(C_1$-$C_6)$alkyl-O—$R^6$, —$C(O)NH_2$, —$N(R^6)_2$, halogen, —$(C_1$-$C_6)$alkyl-$N(R^6)_2$, or nitrile, wherein said —$(C_1$-$C_6)$alkyl, —$O(C_1$-$C_6)$alkyl, —$(C_1$-$C_6)$alkyl-O—$R^6$, or —$(C_1$-$C_6)$alkyl-$N(R^6)_2$ is optionally substituted with one or more substituents selected from the group consisting of —OH, —$N(R^6)_2$, oxo, and halogen, wherein each $R^6$ is independently H or —$(C_1$-$C_6)$alkyl;

or $R^4$ and $R^5$, taken together with the atoms to which they are attached, form a 3-7 membered carbocyclic or heterocyclic ring, which ring is optionally substituted with —OH, —$(C_1$-$C_6)$alkyl, —$O(C_1$-$C_6)$alkyl, —$N(R^6)_2$, halogen, oxo, or nitrile;

or $R^4$ and $R^8$, taken together with the atoms to which they are attached, form a 4-7 membered carbocyclic or heterocyclic ring, which ring is optionally substituted with —OH, —$(C_1$-$C_6)$alkyl, —$O(C_1$-$C_6)$alkyl, —$N(R^6)_2$, halogen, oxo, or nitrile;

or $R^4$ is a bond, and $R^4$ and $R^8$, taken together with the atoms to which they are attached, form a 3-membered carbocyclic or heterocyclic ring, which ring is optionally substituted with —OH, —$(C_1$-$C_6)$alkyl, —$O(C_1$-$C_6)$alkyl, —$N(R^6)_2$, halogen, oxo, or nitrile;

each of $R^{11}$ and $R^{12}$ is, independently, H, —OH, —$(C_1$-$C_6)$alkyl, —$O(C_1$-$C_6)$alkyl, —$(C_1$-$C_6)$alkyl-O—$R^6$, —$C(O)NH_2$, —$N(R^6)_2$, halogen, —$(C_1$-$C_6)$alkyl-$N(R^6)_2$, —$CO_2H$, or nitrile, wherein said —$(C_1$-$C_6)$alkyl, —$O(C_1$-$C_6)$alkyl, —$(C_1$-$C_6)$alkyl-O—$R^6$, or —$(C_1$-$C_6)$alkyl-$N(R^6)_2$ is optionally substituted with one or more substituents selected from the group consisting of —OH, —$N(R^6)_2$, and halogen;

or $R^{11}$ and $R^{12}$, taken together with the atoms to which they are attached, form a 5-7 membered heterocyclic ring;

or $R^4$ and $R^{12}$, taken together with the atoms to which they are attached, form a 5-7 membered carbocyclic or heterocyclic ring;

or $R^8$ and $R^{11}$, taken together with the atoms to which they are attached, form a 5-7 membered carbocyclic or heterocyclic ring;

each of $R^8$ and $R^9$ is, independently, H, —$(C_1$-$C_6)$alkyl, —$(C_1$-$C_6)$alkyl-$N(R^6)_2$, —$OR^6$, —$(C_1$-$C_6)$alkyl-O—$R^6$, —$C(O)NH_2$, —$N(R^6)_2$, halogen, or nitrile;

and each of m and n is, independently, 0, 1, 2, or 3, with m+n being no more than 4.

The invention also provides pharmaceutical compositions containing the compounds described herein. Further, the invention provides a method of inhibiting SHP2 phosphatase activity in a subject by administering a therapeutically effective amount of a compound or composition described herein, to a subject, e.g., a human, in need. The method may include additionally administering a therapeutically effective amount of an antibody, an antibody-drug conjugate, an immunomodulator, or a histone deacetylase inhibitor.

The invention further provides a method of treating a disorder in a subject by administering a therapeutically effective amount of a compound or composition described herein, to a subject in need thereof. Examples of disorders include Noonan syndrome, neutropenia, diabetes, neuroblastoma, melanoma, acute myeloid leukemia, juvenile leukemia, juvenile myelomonocytic leukemia, breast cancer, lung cancer, and colorectal cancer. In addition to the compound or composition described herein, such method may include administration of a therapeutically effective amount of an antibody, an antibody-drug conjugate, an immunomodulator, or a histone deacetylase inhibitor.

The present invention is based, in part, on certain discoveries which are described more fully in the Examples section of the present application. For example, the present invention is based, in part, on the discovery of compounds of Formula (I) and the SHP2 phosphatase inhibition exhibited by such compounds.

These and other embodiments of the invention are further described in the following sections of the application, including the Detailed Description, Examples, and Claims. Still other objects and advantages of the invention will become apparent by those of skill in the art from the disclosure herein, which are simply illustrative and not restrictive. Thus, other embodiments will be recognized by the ordinarily skilled artisan without departing from the spirit and scope of the invention.

DETAILED DESCRIPTION

SHP2 phosphatase inhibitors are disclosed, e.g., in WO 2015/107493; WO 2015/107494; WO 2015/107495; and J. G. Fortanet et al., in *J. Med. Chem.* 2016, DOI: 10.1021/acs.jmedchem.6b00680; and references cited therein; each of which is hereby incorporated by reference in its entirety. The effects of SHP2 phsophatase inhibition are described, e.g., Y.-N. P. Chen et al., in *Nature*, 2016, doi:10.1038/nature18621; J. Wang et al., in *J. Clin. Invest.* 2016, 126, 2077-2092; and references cited therein; each of which is hereby incorporated by reference in its entirety. SHP2 phosphatase inhibitors include, e.g., 8-Hydroxy-7-[(6-sulfo-2-naphthyl)azo]-5-quinolinesulfonic acid (NSC 87877) and SHP099. A novel family of SHP2 phosphatase inhibitors has been discovered and is described herein.

The compounds and/or compositions of the invention, alone or in combination with other treatments, may be effective in treating, reducing, and/or suppressing disorders related to SHP2 phosphatase activity such as, e.g., Noonan syndrome, diabetes, neuroblastoma, melanoma, juvenile leukemia, juvenile myelomonocytic leukemia (JMML), chronic myelomonocytic leukemia, acute myeloid leukemia, HER2-positive breast cancer, triple-negative breast cancer, ductal carcinoma of the breast, invasive ductal carcinoma of the breast, non-small cell lung cancer (including adenocarcinoma of the lung), colorectal cancer, esophageal cancer, gastric cancer, squamous-cell carcinoma of the head and neck (SCCHN), and neutropenia (Kostmann's syndrome). Inhibition of SHP2 phosphatase is described in WO 2015/107493; WO 2015/107494; WO 2015/107495; and references cited therein; each of which hereby incorporated by reference in its entirety.

Abbreviations and Definitions

The term "compound of the invention" as used herein means a compound of Formula (I). The term is also intended to encompass salts thereof.

The term "composition(s) of the invention" as used herein means compositions comprising a compound of the invention, and salts thereof. The compositions of the invention may further comprise other agents such as, e.g., excipients, stabilants, lubricants, solvents, and the like.

The term "isomer" as used herein refers to a compound having the identical chemical formula but different structural or optical configurations. The term "stereoisomer" as used herein refers to and includes isomeric molecules that have the same molecular formula but differ in positioning of atoms and/or functional groups in the space. All stereoisomers of the present compounds (e.g., those which may exist due to asymmetric carbons on various substituents), including enantiomeric forms and diastereomeric forms, are contemplated within the scope of this invention.

The term "tautomer" as used herein refers to one of two or more structural isomers which exist in equilibrium and which are readily converted from one isomeric form to another. It is understood that tautomers encompass valence tautomers and proton tautomers (also known as prototropic tautomers). Valence tautomers include interconversions by reorganization of some of the bonding electrons. Proton tautomers include interconversions via migration of a proton, such as keto-enol and imine-enamine isomerizations.

The term "isotopic substitution" as used herein refers to the substitution of an atom with its isotope. The term "isotope" as used herein refers to an atom having the same atomic number as that of atoms dominant in nature but having a mass number (neutron number) different from the mass number of the atoms dominant in nature. It is understood that a compound with an isotopic substitution refers to a compound in which at least one atom contained therein is substituted with its isotope. Atoms that can be substituted with its isotope include, but are not limited to, hydrogen, carbon, and oxygen. Examples of the isotope of a hydrogen atom include $^2$H (also represented as D) and $^3$H. Examples of the isotope of a carbon atom include $^{13}$C and $^{14}$C. Examples of the isotope of an oxygen atom include $^{18}$O.

The term "alkyl", as used herein, unless otherwise indicated, refers to a monovalent aliphatic hydrocarbon radical having a straight chain, branched chain, monocyclic moiety, or polycyclic moiety or combinations thereof, wherein the radical is optionally substituted at one or more carbons of the straight chain, branched chain, monocyclic moiety, or polycyclic moiety or combinations thereof with one or more substituents at each carbon, wherein the one or more substituents are independently $C_1$-$C_{10}$ alkyl. Examples of "alkyl" groups include methyl, ethyl, propyl, isopropyl, butyl, iso-butyl, sec-butyl, tert-butyl, pentyl, hexyl, heptyl, cyclopropyl, cyclobutyl, cyclopentyl, cyclohexyl, cycloheptyl, norbornyl, and the like.

The term "pharmaceutically acceptable salt" is intended to include salts derived from inorganic or organic acids including, e.g., hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids; and salts derived from inorganic or organic bases including, e.g., sodium, potassium, calcium, magnesium, zinc, ammonia, lysine, arginine, histidine, polyhydroxylated amines or tetrafluoroborate. Exemplary pharmaceutically acceptable salts are found, e.g., in Berge, et al. (*J. Pharm. Sci.* 1977, 66(1), 1; and Gould, P. L., *Int. J. Pharmaceutics* 1986, 33, 201-217; (each hereby incorporated by reference in its entirety). Pharmaceutically acceptable salts are also intended to encompass hemi-salts, wherein the ratio of compound:acid is respectively 2:1. Exemplary hemi-salts are those salts derived from acids comprising two carboxylic acid groups, such as malic acid, fumaric acid, maleic acid, succinic acid, tartaric acid, glutaric acid, oxalic acid, adipic acid and citric acid. Other exemplary hemi-salts are those salts derived from diprotic mineral acids such as sulfuric acid. Exemplary preferred hemi-salts include, but are not limited to, hemimaleate, hemifumarate, and hemisuccinate.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, e.g., to reduce or ameliorate the severity and/or duration of afflictions related to SHP2 phosphatase, or one or more symptoms thereof, prevent the advancement of conditions or symptoms related to afflictions related to SHP2 phosphatase, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease or affliction, a stabilized (i.e., not worsening) state of disease or affliction, preventing spread of disease or affliction, delay or slowing of disease or affliction progression, amelioration or palliation of the disease or affliction state and remission (whether partial or total), whether detectable or undetectable. "Treatment" can also mean prolonging survival as compared to expected survival if not receiving treatment.

The phrase "in need thereof" refers to the need for symptomatic or asymptomatic relief from conditions related to SHP2 phosphatase activity or that may otherwise be relieved by the compounds and/or compositions of the invention.

In some embodiments, SHP2 phosphatase inhibitors described herein encompass compounds of Formula (I) or pharmaceutically acceptable salts thereof,

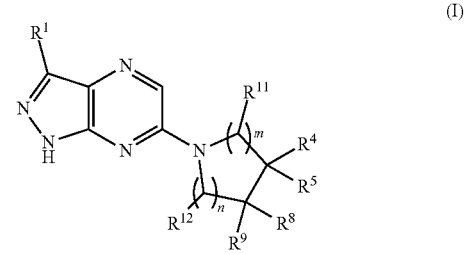

(I)

wherein
$R^1$ is a 5-10 membered monocyclic or bicyclic aryl or heteroaryl, which is optionally substituted with one or more substituents selected from the group consisting of —$R^{10}$, —$OR^{10}$, —$SR^{10}$, —$N(R^{10})_2$, —$OSO_2R^{10}$, —$SO_2R^{10}$, —$C(O)N(R^{10})_2$, halogen, or nitrile, wherein
each $R^{10}$ is, independently, H, —($C_1$-$C_6$)alkyl, —($C_1$-$C_6$)haloalkyl, or —($C_1$-$C_6$)heterocycloalkyl;

each of $R^4$ and $R^5$ is, independently, H, —OH, —($C_1$-$C_6$)alkyl, —O($C_1$-$C_6$)alkyl, —($C_1$-$C_6$)alkyl-O—$R^6$, —C(O)NH$_2$, —N($R^6$)$_2$, halogen, —($C_1$-$C_6$)alkyl-N($R^6$)$_2$, or nitrile, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —OH, —N($R^6$)$_2$, oxo, and halogen, wherein each $R^6$ is independently H or —($C_1$-$C_6$)alkyl;

or $R^4$ and $R^5$, taken together with the atoms to which they are attached, form a 3-7 membered carbocyclic or heterocyclic ring, which ring is optionally substituted with —OH, —($C_1$-$C_6$)alkyl, —O($C_1$-$C_6$)alkyl, —N($R^6$)$_2$, halogen, oxo, or nitrile;

or $R^4$ and $R^8$, taken together with the atoms to which they are attached, form a 4-7 membered carbocyclic or heterocyclic ring, which ring is optionally substituted with —OH, —($C_1$-$C_6$)alkyl, —O($C_1$-$C_6$)alkyl, —N($R^6$)$_2$, halogen, oxo, or nitrile;

or $R^4$ is a bond, and $R^4$ and $R^8$, taken together with the atoms to which they are attached, form a 3-membered carbocyclic or heterocyclic ring, which ring is optionally substituted with —OH, —($C_1$-$C_6$)alkyl, —O($C_1$-$C_6$)alkyl, —N($R^6$)$_2$, halogen, oxo, or nitrile;

each of $R^{11}$ and $R^{12}$ is, independently, H, —OH, —($C_1$-$C_6$)alkyl, —O($C_1$-$C_6$)alkyl, —($C_1$-$C_6$)alkyl-O—$R^6$, —C(O)NH$_2$, —N($R^6$)$_2$, halogen, —($C_1$-$C_6$)alkyl-N($R^6$)$_2$, —CO$_2$H, or nitrile, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —OH, —N($R^6$)$_2$, and halogen;

or $R^{11}$ and $R^{12}$, taken together with the atoms to which they are attached, form a 5-7 membered heterocyclic ring;

or $R^4$ and $R^{12}$, taken together with the atoms to which they are attached, form a 5-7 membered carbocyclic or heterocyclic ring;

or $R^8$ and $R^{11}$, taken together with the atoms to which they are attached, form a 5-7 membered carbocyclic or heterocyclic ring;

each of $R^8$ and $R^9$ is, independently, H, —($C_1$-$C_6$)alkyl, —($C_1$-$C_6$)alkyl-N($R^6$)$_2$, —O$R^6$, —($C_1$-$C_6$)alkyl-O—$R^6$, —C(O)NH$_2$, —N($R^6$)$_2$, halogen, or nitrile;

and each of m and n is, independently, 0, 1, 2, or 3, with m+n being no more than 4.

In some embodiments, $R^1$ is phenyl, pyridyl, or indolyl, wherein said phenyl, pyridyl, or indolyl is optionally substituted with —$R^{10}$, —O$R^{10}$, —S$R^{10}$, —N($R^{10}$)$_2$, —OSO$_2$$R^{10}$, —SO$_2$$R^{10}$, —C(O)N($R^{10}$)$_2$, halogen, or nitrile.

In some embodiments, $R^1$ is H, phenyl, pyridyl, indolyl, naphthyl, quinolinyl, isoquinolinyl, benzimidazolyl, indazolyl, benzotriazolyl, benzothiazolyl, benzofuranyl, pyrazolopyridyl, quinazolinyl, quinoxalinyl, or cinnolinyl.

In some embodiments, $R^1$ is phenyl. In some embodiments, $R^1$ is pyridyl. In some embodiments, $R^1$ is 2-pyridyl. In some embodiments, $R^1$ is 3-pyridyl. In some embodiments, $R^1$ is 4-pyridyl. In some embodiments, $R^1$ is naphthyl. In some embodiments, $R^1$ is 1-naphthyl. In some embodiments, $R^1$ is 2-naphthyl. In some embodiments, $R^1$ is quinolinyl. In some embodiments, $R^1$ is 2-quinolinyl. In some embodiments, $R^1$ is 3-quinolinyl. In some embodiments, $R^1$ is 4-quinolinyl. In some embodiments, $R^1$ is 5-quinolinyl. In some embodiments, $R^1$ is 6-quinolinyl. In some embodiments, $R^1$ is 7-quinolinyl. In some embodiments, $R^1$ is 8-quinolinyl. In some embodiments, $R^1$ is isoquinolinyl. In some embodiments, $R^1$ is 1-isoquinolinyl. In some embodiments, $R^1$ is 3-isoquinolinyl. In some embodiments, $R^1$ is 4-isoquinolinyl. In some embodiments, $R^1$ is 5-isoquinolinyl. In some embodiments, $R^1$ is 6-isoquinolinyl. In some embodiments, $R^1$ is 7-isoquinolinyl. In some embodiments, $R^1$ is 8-isoquinolinyl. In some embodiments, $R^1$ is indolyl. In some embodiments, $R^1$ is 2-indolyl. In some embodiments, $R^1$ is 3-indolyl. In some embodiments, $R^1$ is 4-indolyl. In some embodiments, $R^1$ is 5-indolyl. In some embodiments, $R^1$ is 6-indolyl. In some embodiments, $R^1$ is 7-indolyl. In some embodiments, $R^1$ is aryl. In some embodiments, $R^1$ is bicyclic aryl. In some embodiments, $R^1$ is heteroaryl. In some embodiments, $R^1$ is fused bicyclic heteroaryl.

In some embodiments, $R^1$ is phenyl, pyridyl, or indolyl, wherein said phenyl, pyridyl, or indolyl is optionally substituted with —O$R^{10}$, halogen, or nitrile.

In some embodiments, $R^1$ is phenyl, wherein said phenyl is optionally substituted with —O$R^{10}$, halogen, or nitrile.

In some embodiments, $R^1$ is pyridyl, wherein said pyridyl is optionally substituted with —O$R^{10}$, halogen, or nitrile.

In some embodiments, $R^1$ is indolyl, wherein said indolyl is optionally substituted with —O$R^{10}$, halogen, or nitrile.

In some embodiments, $R^1$ is phenyl, pyridyl, or indolyl, wherein said phenyl, pyridyl, or indolyl is optionally substituted with —O$R^{10}$ or halogen.

In some embodiments, $R^1$ is phenyl, pyridyl, or indolyl, wherein said phenyl, pyridyl, or indolyl is optionally substituted with halogen.

In some embodiments, $R^1$ is phenyl substituted with —$R^{10}$, —O$R^{10}$, —S$R^{10}$, —N($R^{10}$)$_2$, —OSO$_2$$R^{10}$, —SO$_2$$R^{10}$, —C(O)N($R^{10}$)$_2$, halogen, or nitrile. In some embodiments, $R^1$ is phenyl substituted with —$R^{10}$. In some embodiments, $R^1$ is phenyl substituted with —O$R^{10}$. In some embodiments, $R^1$ is phenyl substituted with —S$R^{10}$. In some embodiments, $R^1$ is phenyl substituted with —N($R^{10}$)$_2$. In some embodiments, $R^1$ is phenyl substituted with —OSO$_2$$R^{10}$. In some embodiments, $R^1$ is phenyl substituted with —SO$_2$$R^{10}$. In some embodiments, $R^1$ is phenyl substituted with —C(O)N($R^{10}$)$_2$. In some embodiments, $R^1$ is phenyl substituted with halogen. In some embodiments, $R^1$ is phenyl substituted with nitrile.

In some embodiments, $R^1$ is pyridyl substituted with —$R^{10}$, —O$R^{10}$, —S$R^{10}$, —N($R^{10}$)$_2$, —OSO$_2$$R^{10}$, —SO$_2$$R^{10}$, —C(O)N($R^{10}$)$_2$, halogen, or nitrile. In some embodiments, $R^1$ is pyridyl substituted with —$R^{10}$. In some embodiments, $R^1$ is pyridyl substituted with —O$R^{10}$. In some embodiments, $R^1$ is pyridyl substituted with —S$R^{10}$. In some embodiments, $R^1$ is pyridyl substituted with —N($R^{10}$)$_2$. In some embodiments, $R^1$ is pyridyl substituted with —OSO$_2$$R^{10}$. In some embodiments, $R^1$ is pyridyl substituted with —SO$_2$$R^{10}$. In some embodiments, $R^1$ is pyridyl substituted with —C(O)N($R^{10}$)$_2$. In some embodiments, $R^1$ is pyridyl substituted with halogen. In some embodiments, $R^1$ is pyridyl substituted with nitrile.

In some embodiments, $R^1$ is 3-pyridyl substituted with —O$R^{10}$. In some embodiments, $R^1$ is 3-pyridyl substituted with —OCH$_3$. In some embodiments, $R^1$ is 6-methoxypyrid-3-yl. In some embodiments, $R^1$ is 3-pyridyl substituted with halogen. In some embodiments, $R^1$ is 3-pyridyl substituted with Cl. In some embodiments, $R^1$ is 4-chloropyrid-3-yl. In some embodiments, $R^1$ is 2,3-dichloropyrid-4-yl. In some embodiments, $R^1$ is 3-chloropyrid-2-yl.

In some embodiments, $R^1$ is naphthyl substituted with —$R^{10}$, —O$R^{10}$, —S$R^{10}$, —N($R^{10}$)$_2$, —OSO$_2$$R^{10}$, —SO$_2$$R^{10}$, —C(O)N($R^{10}$)$_2$, halogen, or nitrile. In some embodiments, $R^1$ is naphthyl substituted with —$R^{10}$. In some embodiments, $R^1$ is naphthyl substituted with —O$R^{10}$. In some embodiments, $R^1$ is naphthyl substituted with —S$R^{10}$. In some embodiments, $R^1$ is naphthyl substituted with —N($R^{10}$)$_2$. In some embodiments, $R^1$ is naphthyl substituted with —OSO$_2$R$^{10}$. In some embodiments, R$^1$ is naphthyl substituted with —SO$_2$R$^{10}$. In some embodiments, R$^1$ is naphthyl substituted with —C(O)N(R$^{10}$)$_2$. In some embodiments, R$^1$ is naphthyl substituted with halogen. In some embodiments, R$^1$ is naphthyl substituted with nitrile.

In some embodiments, R$^1$ is quinolinyl substituted with —R$^{10}$, —OR$^{10}$, —SR$^{10}$, —N(R$^{10}$)$_2$, —OSO$_2$R$^{10}$, —SO$_2$R$^{10}$, —C(O)N(R$^{10}$)$_2$, halogen, or nitrile. In some embodiments, R$^1$ is quinolinyl substituted with —R$^{10}$. In some embodiments, R$^1$ is quinolinyl substituted with —OR$^{10}$. In some embodiments, R$^1$ is quinolinyl substituted with —SR$^{10}$. In some embodiments, R$^1$ is quinolinyl substituted with —N(R$^{10}$)$_2$. In some embodiments, R$^1$ is quinolinyl substituted with —OSO$_2$R$^{10}$. In some embodiments, R$^1$ is quinolinyl substituted with —SO$_2$R$^{10}$. In some embodiments, R$^1$ is quinolinyl substituted with —C(O)N(R$^{10}$)$_2$. In some embodiments, R$^1$ is quinolinyl substituted with halogen. In some embodiments, R$^1$ is quinolinyl substituted with nitrile.

In some embodiments, R$^1$ is isoquinolinyl substituted with —R$^{10}$, —OR$^{10}$, —SR$^{10}$, —N(R$^{10}$)$_2$, —OSO$_2$R$^{10}$, —SO$_2$R$^{10}$, —C(O)N(R$^{10}$)$_2$, halogen, or nitrile. In some embodiments, R$^1$ is isoquinolinyl substituted with —R$^{10}$. In some embodiments, R$^1$ is isoquinolinyl substituted with —OR$^{10}$. In some embodiments, R$^1$ is isoquinolinyl substituted with —SR$^{10}$. In some embodiments, R$^1$ is isoquinolinyl substituted with —N(R$^{10}$)$_2$. In some embodiments, R$^1$ is isoquinolinyl substituted with —OSO$_2$R$^{10}$. In some embodiments, R$^1$ is isoquinolinyl substituted with —SO$_2$R$^{10}$. In some embodiments, R$^1$ is isoquinolinyl substituted with —C(O)N(R$^{10}$)$_2$. In some embodiments, R$^1$ is isoquinolinyl substituted with halogen. In some embodiments, R$^1$ is isoquinolinyl substituted with nitrile.

In some embodiments, R$^1$ is indolyl substituted with —R$^{10}$, —OR$^{10}$, —SR$^{10}$, —N(R$^{10}$)$_2$, —OSO$_2$R$^{10}$, —SO$_2$R$^{10}$, —C(O)N(R$^{10}$)$_2$, halogen, or nitrile. In some embodiments, R$^1$ is indolyl substituted with —R$^{10}$. In some embodiments, R$^1$ is indolyl substituted with —OR$^{10}$. In some embodiments, R$^1$ is indolyl substituted with —SR$^{10}$. In some embodiments, R$^1$ is indolyl substituted with —N(R$^{10}$)$_2$. In some embodiments, R$^1$ is indolyl substituted with —OSO$_2$R$^{10}$. In some embodiments, R$^1$ is indolyl substituted with —SO$_2$R$^{10}$. In some embodiments, R$^1$ is indolyl substituted with —C(O)N(R$^{10}$)$_2$. In some embodiments, R$^1$ is indolyl substituted with halogen. In some embodiments, R$^1$ is indolyl substituted with nitrile.

In some embodiments, R$^1$ is 1-methyl-1H-indol-4-yl. In some embodiments, R$^1$ is 1-methyl-1H-indol-3-yl.

In some embodiments, R$^4$ and R$^5$ are independently H, —OH, —(C$_1$-C$_6$)alkyl, —O(C$_1$-C$_6$)alkyl, —(C$_1$-C$_6$)alkyl-O—R$^6$, —C(O)NH$_2$, —N(R$^6$)$_2$, halogen, —(C$_1$-C$_6$)alkyl-N(R$^6$)$_2$, or nitrile.

In some embodiments, R$^4$ and R$^5$ are independently H, —OH, —(C$_1$-C$_3$)alkyl, —O(C$_1$-C$_3$)alkyl, —(C$_1$-C$_3$)alkyl-O—R$^6$, —C(O)NH$_2$, —N(R$^6$)$_2$, halogen, —(C$_1$-C$_3$)alkyl-N(R$^6$)$_2$, or nitrile.

In some embodiments, R$^4$ and R$^5$ are independently H, —(C$_1$-C$_6$)alkyl, or —(C$_1$-C$_6$)alkyl-N(R$^6$2. In some embodiments, R$^4$ and R$^5$ are independently H, —(C$_1$-C$_6$)alkyl, or —(C$_1$-C$_4$)alkyl-N(R$^6$)$_2$. In some embodiments, R$^4$ and R$^5$ are independently H, —(C$_1$-C$_2$)alkyl, or —(C$_1$-C$_4$)alkyl-N(R$^6$)$_2$. In some embodiments, R$^4$ and R$^5$ are independently H, —CH$_3$, or —(C$_1$-C$_4$)alkyl-NH$_2$. In some embodiments, R$^4$ and R$^5$ are independently H, —CH$_3$, or —(C$_1$-C$_2$)alkyl-NH$_2$. In some embodiments, R$^4$ and R$^5$ are independently H, —CH$_3$, or —CH$_2$—NH$_2$. In some embodiments, R$^4$ and R$^5$ are independently —CH$_3$ or —(C$_1$-C$_4$)alkyl-NH$_2$. In some embodiments, R$^4$ and R$^5$ are independently —CH$_3$ or —(C$_1$-C$_2$)alkyl-NH$_2$. In some embodiments, R$^4$ and R$^5$ are independently —CH$_3$ or —CH$_2$—NH$_2$. In some embodiments, R$^4$ and R$^5$ are independently —CH$_3$ or —CH$_2$CH$_2$—NH$_2$. In some embodiments, R$^4$ and R$^5$ are independently H or —CH$_2$—NH$_2$.

In some embodiments, R$^4$ and R$^5$ are independently H, —(C$_1$-C$_6$)alkyl, or —N(R$^6$)$_2$. In some embodiments, R$^4$ and R$^5$ are independently —(C$_1$-C$_6$)alkyl or —N(R$^6$)$_2$. In some embodiments, R$^4$ and R$^5$ are independently —(C$_1$-C$_4$)alkyl or —N(R$^6$)$_2$. In some embodiments, R$^4$ and R$^5$ are independently —(C$_1$-C$_2$)alkyl or —N(R$^6$)$_2$. In some embodiments, R$^4$ and R$^5$ are independently —CH$_3$ or —N(R$^6$)$_2$. In some embodiments, R$^4$ and R$^5$ are independently —CH$_3$ or —NH$_2$. In some embodiments, R$^4$ and R$^5$ are independently —CH$_3$ or —NHCH$_3$.

In some embodiments, R$^4$ and R$^5$ are independently H, —OH, or —(C$_1$-C$_6$)alkyl-N(R$^6$)$_2$. In some embodiments, R$^4$ and R$^5$ are independently H, OH, or —(C$_1$-C$_4$)alkyl-N(R$^6$)$_2$. In some embodiments, R$^4$ and R$^5$ are independently H, OH, or —(C$_1$-C$_4$)alkyl-NH$_2$. In some embodiments, R$^4$ and R$^5$ are independently H, OH, or —(C$_1$-C$_2$)alkyl-NH$_2$. In some embodiments, R$^4$ and R$^5$ are independently H, OH, or —CH$_2$—NH$_2$. In some embodiments, R$^4$ and R$^5$ are independently OH or —(C$_1$-C$_4$)alkyl-NH$_2$. In some embodiments, R$^4$ and R$^5$ are independently OH or —(C$_1$-C$_2$)alkyl-NH$_2$. In some embodiments, R$^4$ and R$^5$ are independently OH or —CH$_2$—NH$_2$. In some embodiments, R$^4$ and R$^5$ are independently OH or —CH$_2$CH$_2$—NH$_2$.

In some embodiments, R$^4$ and R$^5$ are independently —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$, wherein said —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$ is optionally substituted with one or more substituents selected from the group consisting of —OH, —N(R$^6$)$_2$, C(O), and halogen. In some embodiments, R$^4$ and R$^5$ are independently —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$, wherein said —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$ is optionally substituted with one or more substituents selected from the group consisting of —OH, —NH$_2$, and fluoro. In some embodiments, R$^4$ and R$^5$ are independently —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$, wherein said —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$ is optionally substituted with one or more substituents selected from the group consisting of —OH and fluoro. In some embodiments, R$^4$ and R$^5$ are independently —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$, wherein said —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$ is optionally substituted with one or more substituents selected from the group consisting of —NH$_2$ and fluoro.

In some embodiments, R$^4$ and R$^5$, taken together with the atoms to which they are attached, form a 3-7 membered carbocyclic or heterocyclic ring. In some embodiments, the 3-7 membered carbocyclic or heterocyclic ring is optionally substituted with —OH, —(C$_1$-C$_6$)alkyl, —O(C$_1$-C$_6$)alkyl, —N(R$^6$)$_2$, halogen, oxo, or nitrile.

In some embodiments, R$^4$ and R$^8$, taken together with the atoms to which they are attached, form a 4-7 membered carbocyclic or heterocyclic ring. In some embodiments, the 4-7 membered carbocyclic or heterocyclic ring is optionally substituted with —OH, —(C$_1$-C$_6$)alkyl, —O(C$_1$-C$_6$)alkyl, —N(R$^6$)$_2$, halogen, oxo, or nitrile.

In some embodiments, $R^4$ is a bond, and $R^4$ and $R^8$, taken together with the atoms to which they are attached, form a 3-membered carbocyclic or heterocyclic ring. In some embodiments, the 3-membered carbocyclic or heterocyclic ring is optionally substituted with —OH, —($C_1$-$C_6$)alkyl, —O($C_1$-$C_6$)alkyl, —N($R^6$)$_2$, halogen, oxo, or nitrile.

In some embodiments, $R^1$ and $R^{12}$ are independently H, —OH, —($C_1$-$C_6$)alkyl, —O($C_1$-$C_6$)alkyl, —($C_1$-$C_6$)alkyl-O—$R^6$, —C(O)NH$_2$, —N($R^6$)$_2$, halogen, —($C_1$-$C_6$)alkyl-N($R^6$)$_2$, —CO$_2$H, or nitrile. In some embodiments, $R^{11}$ and $R^{12}$ are independently H or —($C_1$-$C_6$)alkyl. In some embodiments, $R^{11}$ and $R^{12}$ are independently H or —($C_1$-$C_4$)alkyl. In some embodiments, $R^{11}$ and $R^{12}$ are independently H or —($C_1$-$C_2$)alkyl. In some embodiments, $R^{11}$ and $R^{12}$ are independently H or —CH$_3$.

In some embodiments, $R^{11}$ and $R^{12}$ are independently —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —OH, —N($R^6$)$_2$, and halogen. In some embodiments, $R^{11}$ and $R^{12}$ are independently —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —OH, —NH$_2$, and fluoro. In some embodiments, $R^{11}$ and $R^{12}$ are independently —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —OH and fluoro. In some embodiments, $R^{11}$ and $R^{12}$ are independently —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —NH$_2$ and fluoro.

In some embodiments, each $R^6$ is independently H or —($C_1$-$C_6$)alkyl. In some embodiments, each $R^6$ is independently H or —($C_1$-$C_4$)alkyl. In some embodiments, each $R^6$ is independently H or —($C_1$-$C_3$)alkyl. In some embodiments, each $R^6$ is independently H or —($C_1$-$C_2$)alkyl. In some embodiments, each $R^6$ is independently H or —CH$_3$. In some embodiments, each $R^6$ is independently —($C_1$-$C_6$)alkyl. In some embodiments, each $R^6$ is independently —($C_1$-$C_4$)alkyl. In some embodiments, each $R^6$ is independently —($C_1$-$C_2$)alkyl. In some embodiments, each $R^6$ is independently —CH$_3$. In some embodiments, each $R^6$ is independently H, —CH$_3$, or —CH$_2$CH$_3$. In some embodiments, each $R^6$ is independently —CH$_3$ or —CH$_2$CH$_3$.

In some embodiments, $R^8$ and $R^9$ are independently H, —($C_1$-$C_6$)alkyl, —($C_1$-$C_6$)alkyl-N($R^6$)$_2$, —O$R^6$, —($C_1$-$C_6$)alkyl-O—$R^6$, —C(O)NH$_2$, —N($R^6$)$_2$, halogen, or nitrile. In some embodiments, $R^8$ and $R^9$ are independently H, —($C_1$-$C_6$)alkyl, or —($C_1$-$C_6$)alkyl-N($R^6$)$_2$. In some embodiments, $R^8$ and $R^9$ are independently H, —($C_1$-$C_6$)alkyl, or —($C_1$-$C_4$)alkyl-N($R^6$)$_2$. In some embodiments, $R^8$ and $R^9$ are independently H, —($C_1$-$C_2$)alkyl, or —($C_1$-$C_4$)alkyl-N($R^6$)$_2$. In some embodiments, $R^8$ and $R^9$ are independently H, —CH$_3$, or —($C_1$-$C_4$)alkyl-NH$_2$. In some embodiments, $R^8$ and $R^9$ are independently H, —CH$_3$, or —($C_1$-$C_2$)alkyl-NH$_2$. In some embodiments, $R^8$ and $R^9$ are independently H, —CH$_3$, or —CH$_2$—NH$_2$. In some embodiments, $R^8$ and $R^9$ are independently —CH$_3$ or —($C_1$-$C_4$)alkyl-NH$_2$. In some embodiments, $R^8$ and $R^9$ are independently —CH$_3$ or —($C_1$-$C_2$)alkyl-NH$_2$. In some embodiments, $R^8$ and $R^9$ are independently —CH$_3$ or —CH$_2$—NH$_2$. In some embodiments, $R^8$ and $R^9$ are independently —CH$_3$ or —CH$_2$CH$_2$—NH$_2$. In some embodiments, $R^8$ and $R^9$ are independently H or —CH$_2$—NH$_2$.

In some embodiments, each $R^{10}$ is independently H, —($C_1$-$C_{10}$)alkyl, —($C_1$-$C_{10}$)heteroalkyl, or —($C_1$-$C_6$)heterocycloalkyl. In some embodiments, each $R^{10}$ is independently H, —($C_1$-$C_{10}$)alkyl, or —($C_1$-$C_{10}$)heteroalkyl. In some embodiments, each $R^{10}$ is independently H or —($C_1$-$C_4$)alkyl. In some embodiments, each $R^{10}$ is independently H or —($C_1$-$C_2$)alkyl. In some embodiments, each $R^{10}$ is independently H or —CH$_3$. In some embodiments, each $R^{10}$ is independently —($C_1$-$C_{10}$)alkyl. In some embodiments, each $R^{10}$ is independently —($C_1$-$C_8$)alkyl. In some embodiments, each $R^{10}$ is independently —($C_1$-$C_6$)alkyl. In some embodiments, each $R^{10}$ is independently —($C_1$-$C_4$)alkyl. In some embodiments, each $R^{10}$ is independently —($C_1$-$C_2$)alkyl. In some embodiments, each $R^{10}$ is independently —CH$_3$. In some embodiments, each $R^{10}$ is independently H, —CH$_3$, or —CH$_2$CH$_3$. In some embodiments, each $R^{10}$ is independently —CH$_3$ or —CH$_2$CH$_3$.

In some embodiments, each $R^{10}$ is —($C_1$-$C_{10}$)alkyl or —($C_1$-$C_{10}$)heteroalkyl independently substituted with one or more substituents selected from the group consisting of —O$R^6$, —N($R^6$)$_2$, —C(O), and halogen. In some embodiments, each $R^{10}$ is —($C_1$-$C_{10}$)alkyl or —($C_1$-$C_{10}$)heteroalkyl independently substituted with one or more substituents selected from the group consisting of —O$R^6$, —N($R^6$)$_2$, and halogen. In some embodiments, each $R^{10}$ is —($C_1$-$C_{10}$)alkyl or —($C_1$-$C_{10}$)heteroalkyl independently substituted with one or more substituents selected from the group consisting of —O$R^6$ and —N($R^6$)$_2$. In some embodiments, each $R^{10}$ is —($C_1$-$C_{10}$)alkyl or —($C_1$-$C_{10}$)heteroalkyl independently substituted with one or more substituents selected from the group consisting of —C(O), and halogen. In some embodiments, each $R^{10}$ is —($C_1$-$C_{10}$)alkyl or —($C_1$-$C_{10}$)heteroalkyl independently substituted with one or more substituents selected from the group consisting of —N($R^6$)$_2$ and —C(O). In some embodiments, each $R^{10}$ is —($C_1$-$C_{10}$)alkyl or —($C_1$-$C_{10}$)heteroalkyl independently substituted with one or more substituents selected from the group consisting of —OH, —NH$_2$, —C(O), and halogen. In some embodiments, each $R^{10}$ is —($C_1$-$C_{10}$)alkyl or —($C_1$-$C_{10}$)heteroalkyl independently substituted with one or more substituents selected from the group consisting of —OH, —NH$_2$, and halogen. In some embodiments, each $R^{10}$ is —($C_1$-$C_{10}$)alkyl or —($C_1$-$C_{10}$)heteroalkyl independently substituted with one or more substituents selected from the group consisting of —OH and —NH$_2$.

In some embodiments, each $R^{10}$ is independently substituted with one or more substituents selected from the group consisting of —O$R^6$, —N($R^6$)$_2$, —C(O), and halogen. In some embodiments, each $R^{10}$ is independently substituted with one or more substituents selected from the group consisting of —O$R^6$, —N($R^6$)$_2$, and halogen. In some embodiments, each $R^{10}$ is independently substituted with one or more substituents selected from the group consisting of —O$R^6$ and —N($R^6$)$_2$. In some embodiments, each $R^{10}$ is independently substituted with one or more substituents selected from the group consisting of —C(O), and halogen. In some embodiments, each $R^{10}$ is independently substituted with one or more substituents selected from the group consisting of —N($R^6$)$_2$ and —C(O). In some embodiments, each $R^{10}$ is independently substituted with one or more substituents selected from the group consisting of —OH, —NH$_2$, —C(O), and halogen. In some embodiments, each R$^{10}$ is independently substituted with one or more substituents selected from the group consisting of —OH, —NH$_2$, and halogen. In some embodiments, each R$^{10}$ is independently substituted with one or more substituents selected from the group consisting of —OH and —NH$_2$.

In some embodiments, each R$^{10}$, taken together with the atoms to which they are attached, form a 3-7 membered carbocyclic or heterocyclic ring.

In some embodiments, R$^1$ is selected from the group consisting of

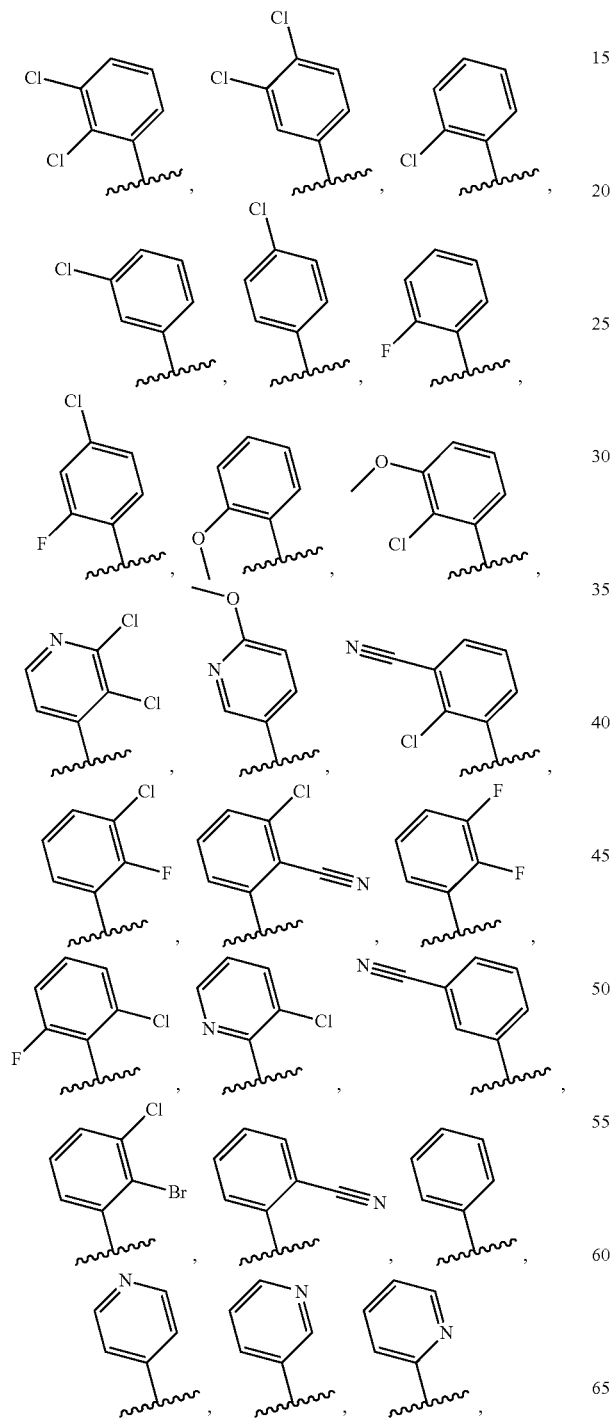

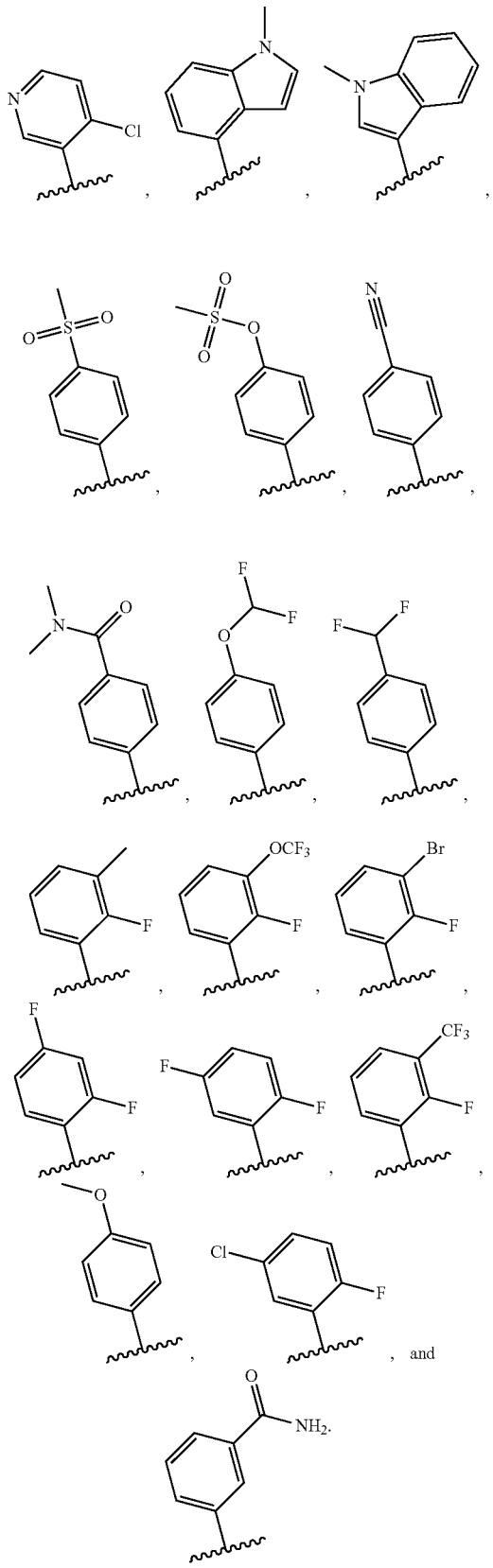

In some embodiments, R¹ is
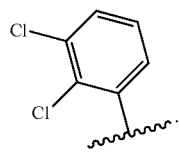
In some embodiments, R¹ is
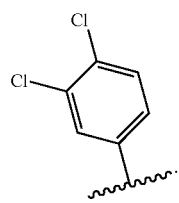 [SMILES: *c1ccc(Cl)c(Cl)c1]
In some embodiments, R¹ is
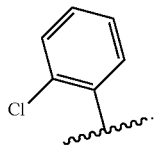 [SMILES: *c1ccccc1Cl]
In some embodiments, R¹ is
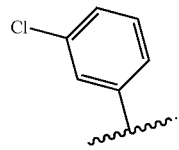
In some embodiments, R¹ is
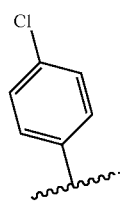 [SMILES: *c1ccc(Cl)cc1]
In some embodiments, R¹ is
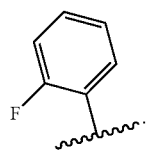
In some embodiments, R¹ is
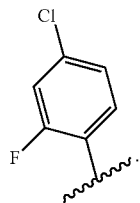
In some embodiments, R¹ is
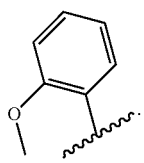 [SMILES: *c1ccccc1OC]
In some embodiments, R¹ is
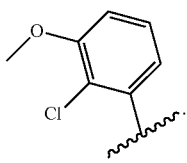 [SMILES: *c1cccc(OC)c1Cl]
In some embodiments, R¹ is
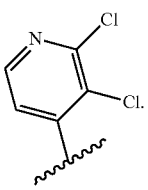 [SMILES: *c1ccnc(Cl)c1Cl]
In some embodiments, R¹ is
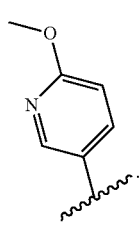 [SMILES: *c1ccc(OC)nc1]
In some embodiments, R¹ is
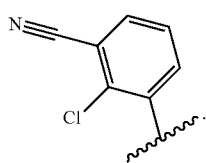 [SMILES: *c1cccc(C#N)c1Cl]

In some embodiments, R¹ is
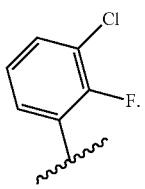
In some embodiments, R¹ is
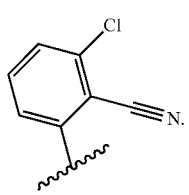 [SMILES: *c1cccc(Cl)c1C#N]
In some embodiments, R¹ is
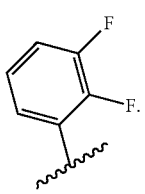
In some embodiments, R¹ is
In some embodiments, R¹ is
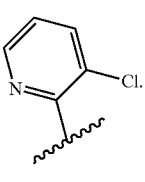 [SMILES: *c1ncccc1Cl]
In some embodiments, R¹ is
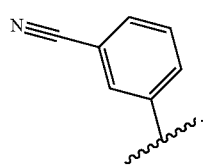 [SMILES: *c1cccc(C#N)c1]
In some embodiments, R¹ is
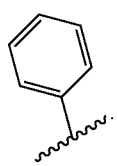 [SMILES: *c1ccccc1]
In some embodiments, R¹ is
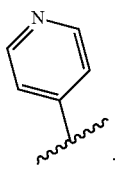 [SMILES: *c1ccncc1]
In some embodiments, R¹ is
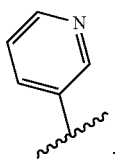 [SMILES: *c1cccnc1]
In some embodiments, R¹ is
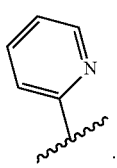

In some embodiments, $R^1$ is
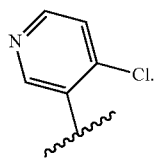
In some embodiments, $R^1$ is
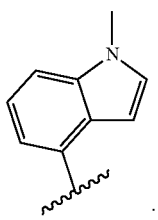 [SMILES: *c1cccc2c1ccn2C]
In some embodiments, $R^1$ is
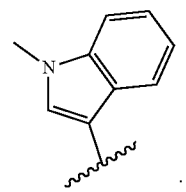 [SMILES: *c1cn(C)c2ccccc12]
In some embodiments, $R^1$ is
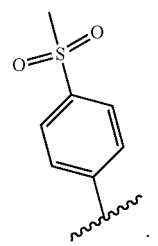 [SMILES: *c1ccc(S(C)(=O)=O)cc1]
In some embodiments, $R^1$ is
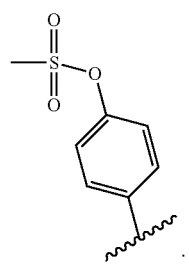 [SMILES: *c1ccc(OS(C)(=O)=O)cc1]
In some embodiments, $R^1$ is
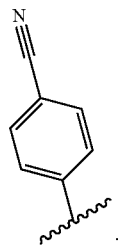 [SMILES: *c1ccc(C#N)cc1]
In some embodiments, $R^1$ is
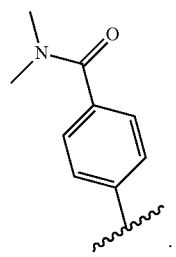 [SMILES: *c1ccc(C(=O)N(C)C)cc1]
In some embodiments, $R^1$ is
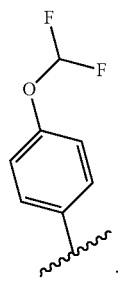 [SMILES: *c1ccc(OC(F)F)cc1]
In some embodiments, $R^1$ is
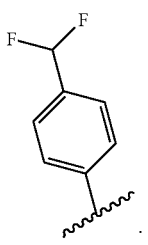
In some embodiments, $R^1$ is
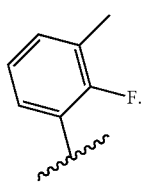 [SMILES: *c1cccc(C)c1F]

In some embodiments, R¹ is
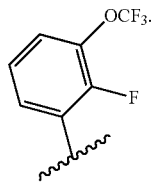 [SMILES: *c1cccc(OC(F)(F)F)c1F]
In some embodiments, R¹ is
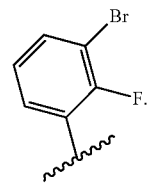
In some embodiments, R¹ is
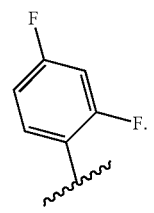 [SMILES: *c1ccc(F)cc1F]
In some embodiments, R¹ is
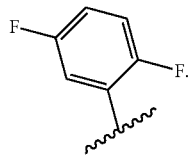 [SMILES: *c1cc(F)ccc1F]
In some embodiments, R¹ is
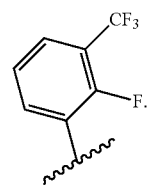
In some embodiments, R¹ is
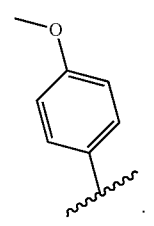 [SMILES: *c1ccc(OC)cc1]
In some embodiments, R¹ is. In some embodiments, R¹ is
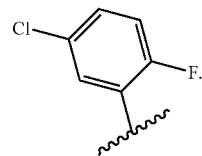 [SMILES: *c1cc(Cl)ccc1F]
In some embodiments, R¹ is
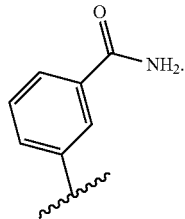 [SMILES: *c1cccc(C(N)=O)c1]
In some embodiments, the moiety
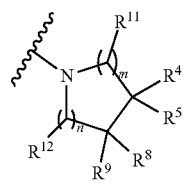
is selected from the group consisting of
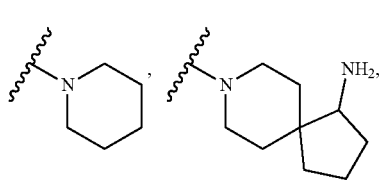
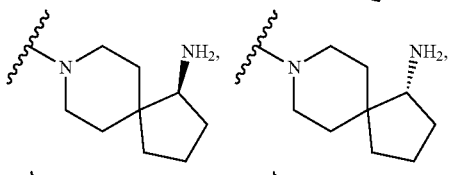
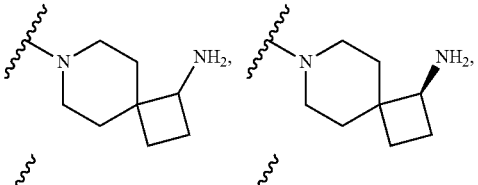
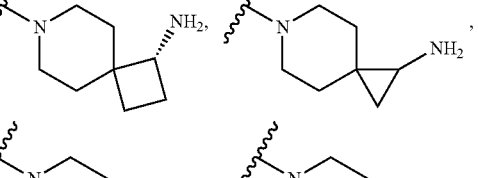
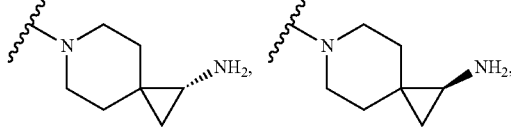

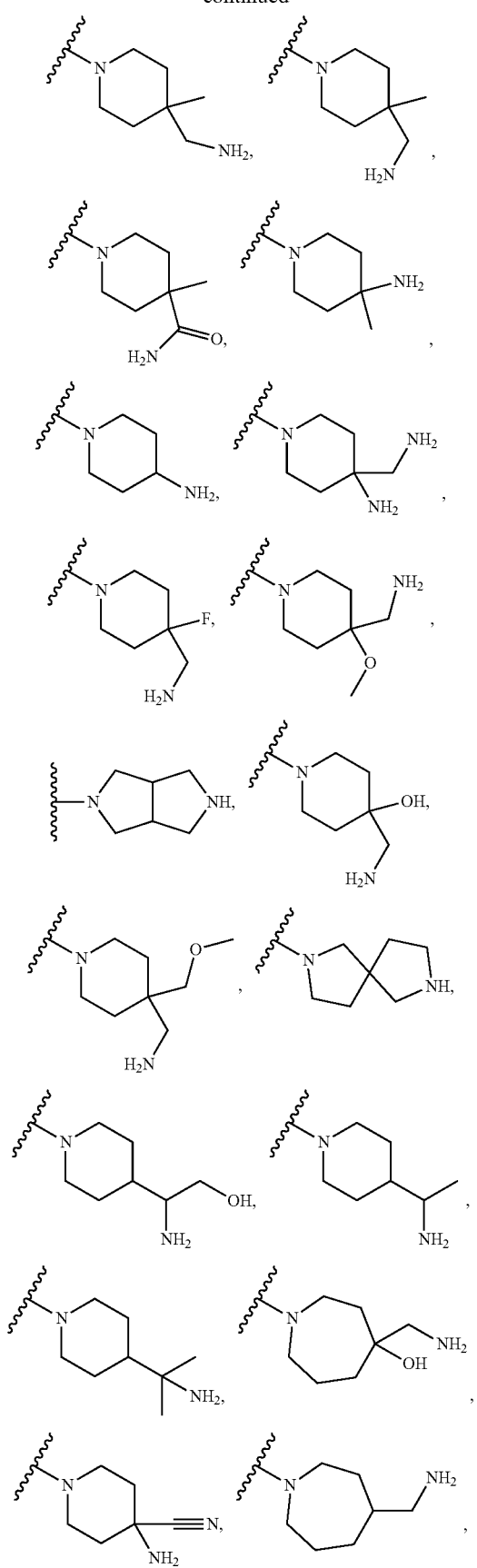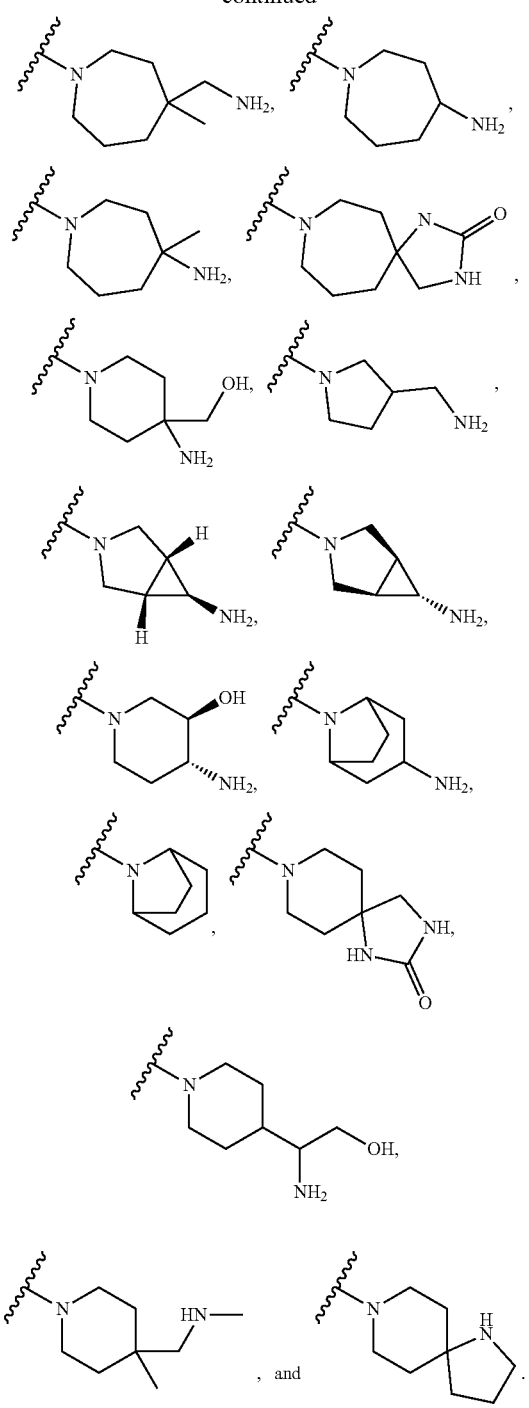
In some embodiments, the moiety
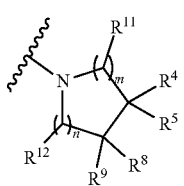

is selected from the group consisting of
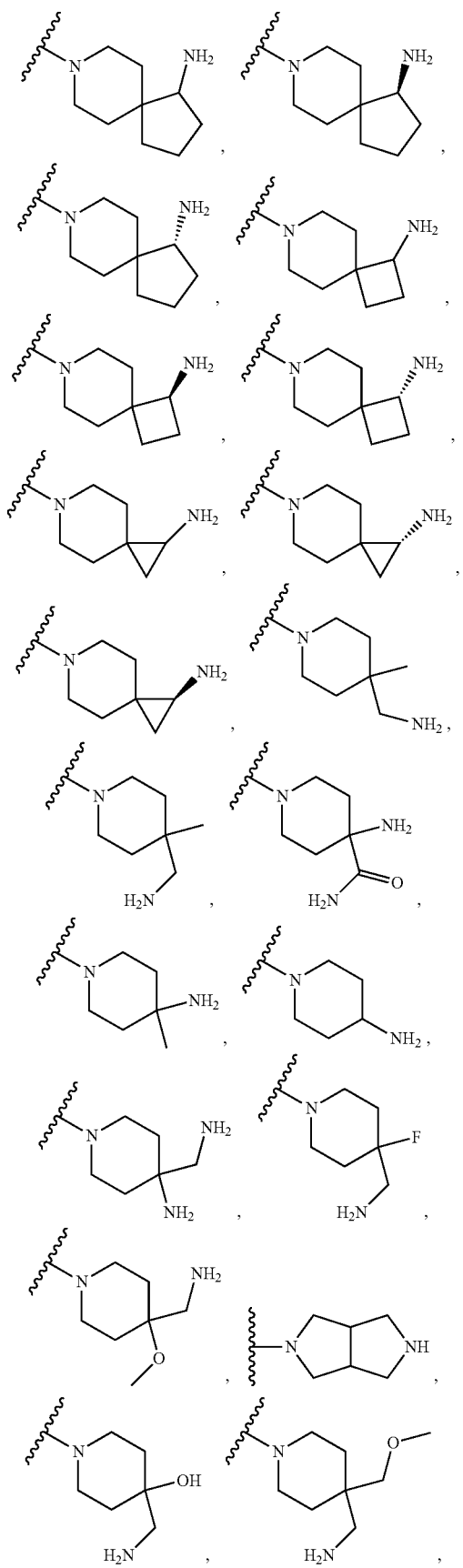
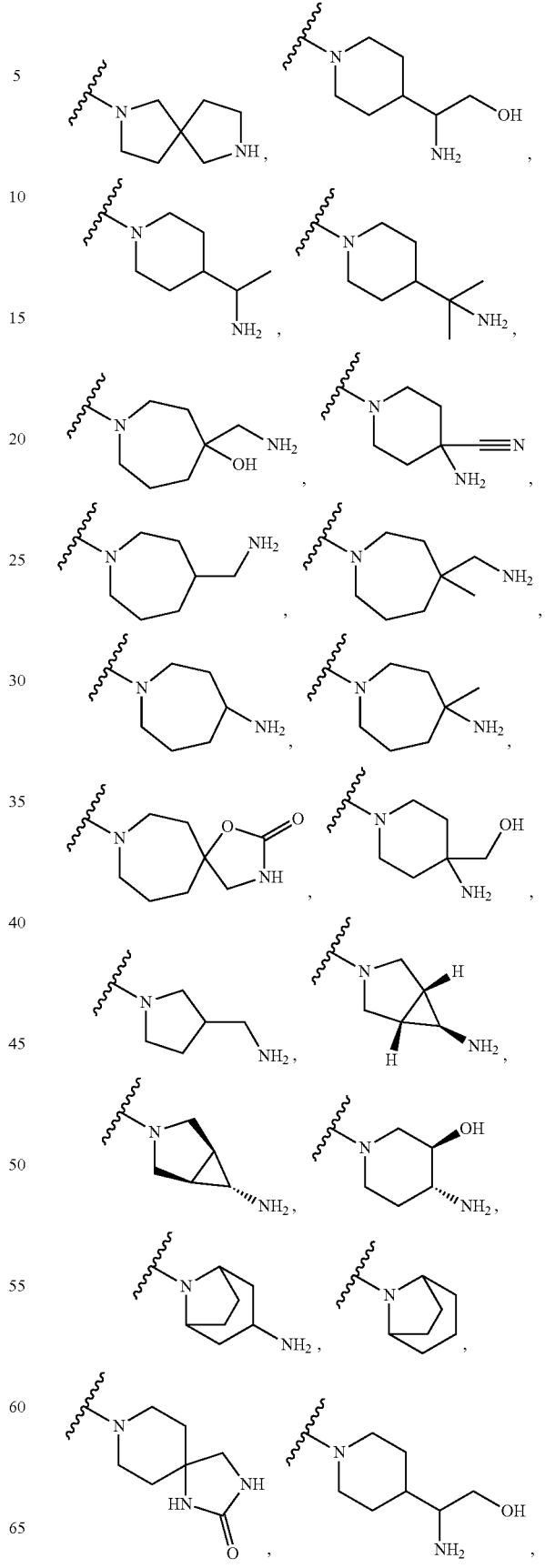

-continued
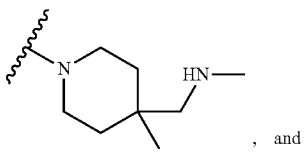
, and
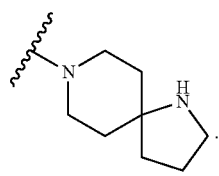
In some embodiments, the moiety shown below is referred to as R².
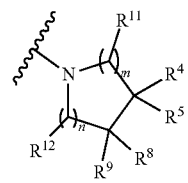
In some embodiments, R² is
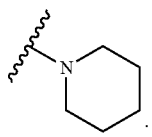
In some embodiments, R² is
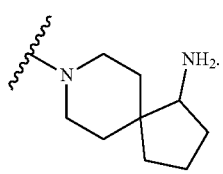 [SMILES: *N1CCC2(CCCC2N)CC1]
In some embodiments, R² is
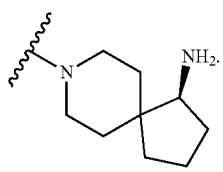 [SMILES: *N1CCC2(CCC[C@@H]2N)CC1]
In some embodiments, R² is
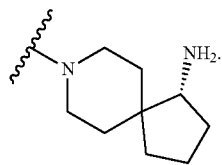 [SMILES: *N1CCC2(CCC[C@H]2N)CC1]
In some embodiments, R² is
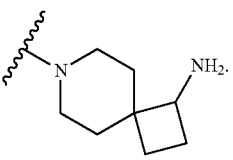 [SMILES: *N1CCC2(CCC2N)CC1]
In some embodiments, R² is
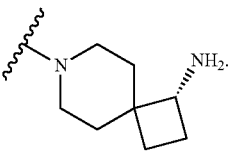 [SMILES: *N1CCC2(CC[C@H]2N)CC1]
In some embodiments, R² is
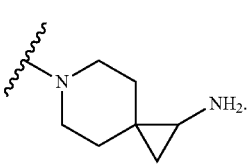 [SMILES: *N1CCC2(CC1)CC2N]
In some embodiments, R² is
embodiments, R² is
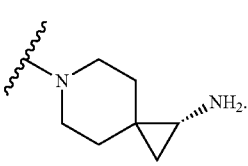 [SMILES: *N1CCC2(CC1)C[C@H]2N]

In some embodiments, R² is
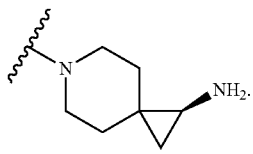
In some embodiments, R² is
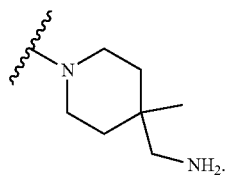
In some embodiments, R² is
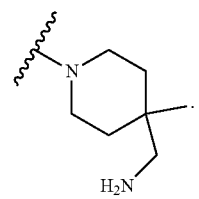
In some embodiments, R² is
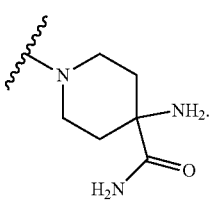
In some embodiments, R² is
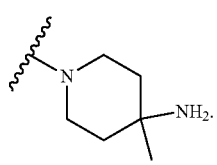 [SMILES: *N1CCC(C)(N)CC1]
In some embodiments, R² is
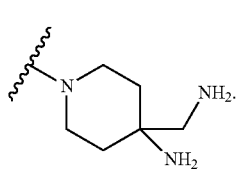 [SMILES: *N1CCC(N)(CN)CC1]
In some embodiments, R² is
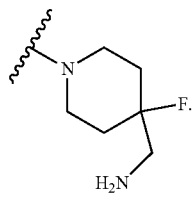 [SMILES: *N1CCC(F)(CN)CC1]
In some embodiments, R² is
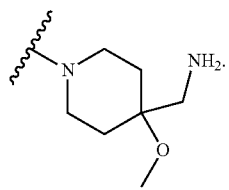 [SMILES: *N1CCC(CN)(OC)CC1]
In some embodiments, R² is
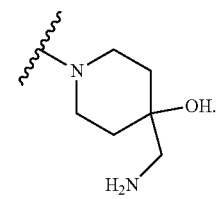 [SMILES: *N1CCC(O)(CN)CC1]
In some embodiments, R² is
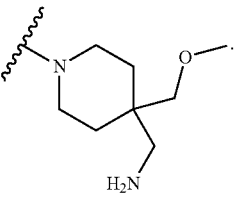 [SMILES: *N1CCC(CN)(COC)CC1]
In some embodiments, R² is
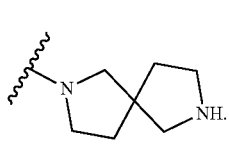 [SMILES: *N1CCC2(CCNC2)C1]
In some embodiments, R is
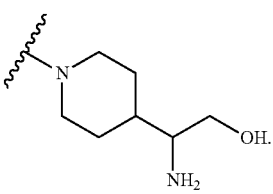 [SMILES: *N1CCC(C(N)CO)CC1]

In some embodiments, R² is
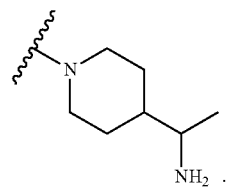 [SMILES: *N1CCC(C(C)N)CC1]
In some embodiments, R² is
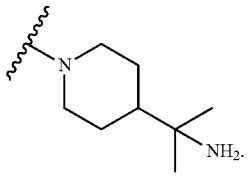 [SMILES: *N1CCC(C(C)(C)N)CC1]
In some embodiments, R² is
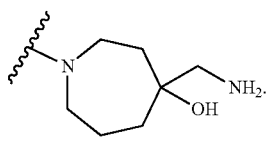 [SMILES: *N1CCCC(O)(CN)CC1]
In some embodiments, R² is
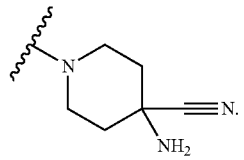 [SMILES: *N1CCC(N)(C#N)CC1]
In some embodiments, R² is
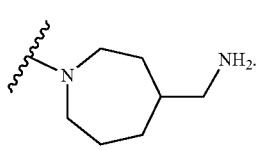 [SMILES: *N1CCCC(CN)CC1]
In some embodiments, R² is
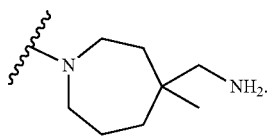 [SMILES: *N1CCCC(C)(CN)CC1]
In some embodiments, R² is
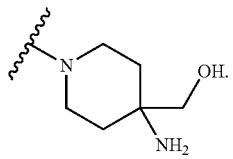 [SMILES: *N1CCC(N)(CO)CC1]
In some embodiments, R² is
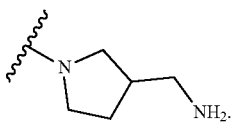
In some embodiments, R² is
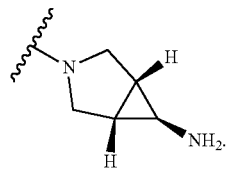 [SMILES: *N1C[C@@H]2[C@@H](N)[C@@H]2C1]
In some embodiments, R² is
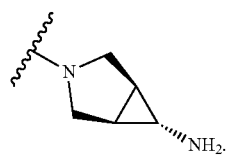
In some embodiments, R² is
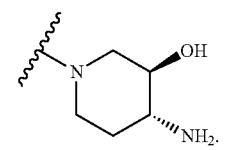
In some embodiments, R² is
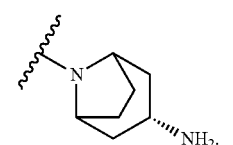
In some embodiments, R² is
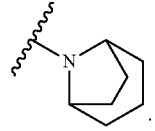 [SMILES: *N1C2CCCC1CC2]

In some embodiments, R² is

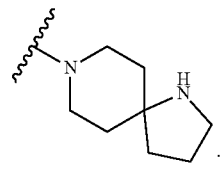 [SMILES: *N1CCC2(CCCN2)CC1]

In some embodiments, R² is

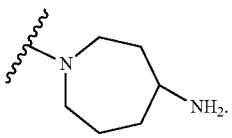 [SMILES: *N1CCCC(N)CC1]

In some embodiments, R² is

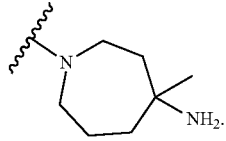 [SMILES: *N1CCCC(C)(N)CC1]

In some embodiments, R² is

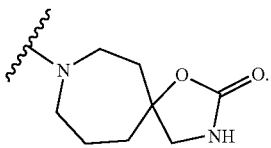 [SMILES: *N1CCCC2(CC1)CNC(=O)O2]

In some embodiments, R² is

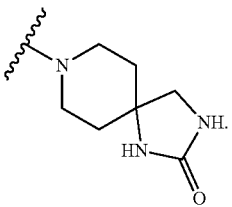 [SMILES: *N1CCC2(CC1)CNC(=O)N2]

In some embodiments, R² is

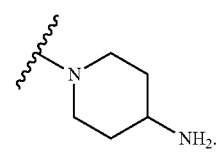 [SMILES: *N1CCC(N)CC1]

In some embodiments, R² is

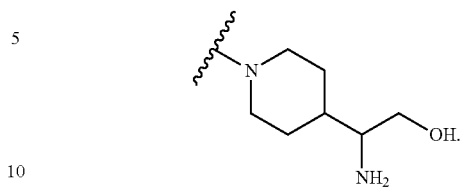

In some embodiments, R² is

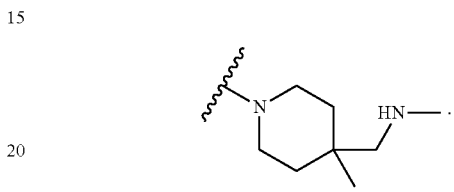

In some embodiments, m is an integer selected from 0, 1, 2, or 3 and n is an integer selected from 0, 1, 2, or 3. In some embodiments, m is an integer selected from 0, 1, or 2 and n is an integer selected from 0, 1, or 2. In some embodiments, m is an integer selected from 0 or 1 and n is an integer selected from 0 or 1. In some embodiments, m is 0 and n is 0. In some embodiments, m is 0 and n is 1. In some embodiments, m is 0 and n is 2. In some embodiments, m is 0 and n is 3. In some embodiments, m is 1 and n is 0. In some embodiments, m is 1 and n is 1. In some embodiments, m is 1 and n is 2. In some embodiments, m is 1 and n is 3. In some embodiments, m is 2 and n is 0. In some embodiments, m is 2 and n is 1. In some embodiments, m is 2 and n is 2. In some embodiments, m is 3 and n is 0. In some embodiments, m is 3 and n is 1.

Examples of compounds of the invention include:

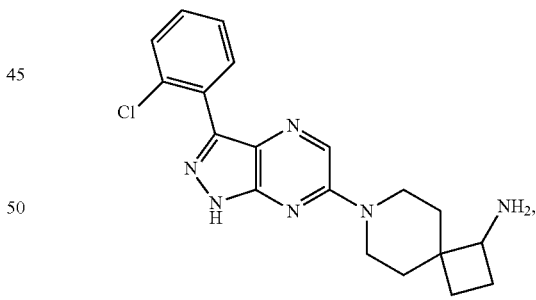

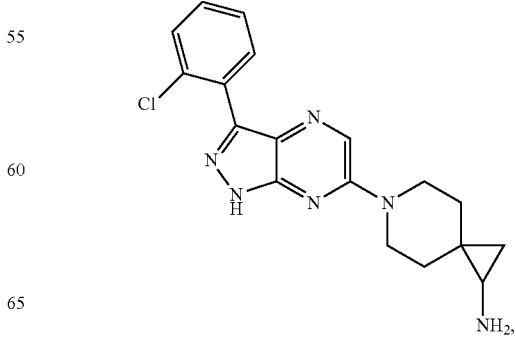

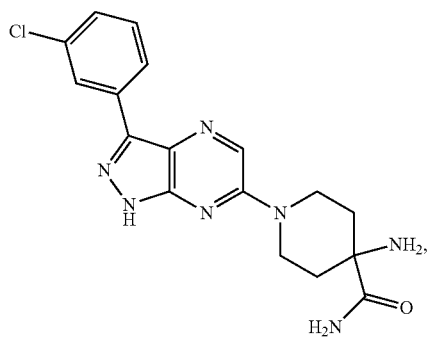
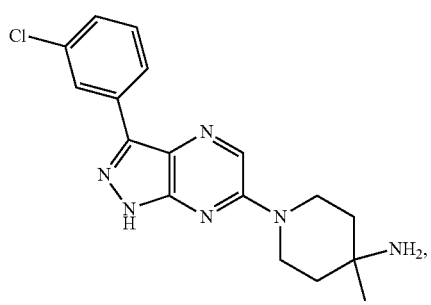
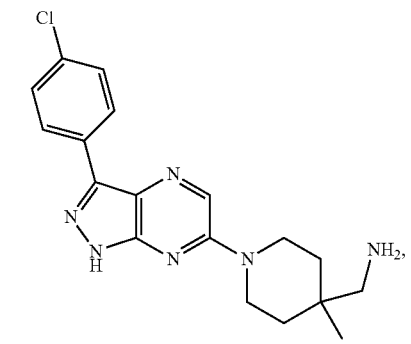
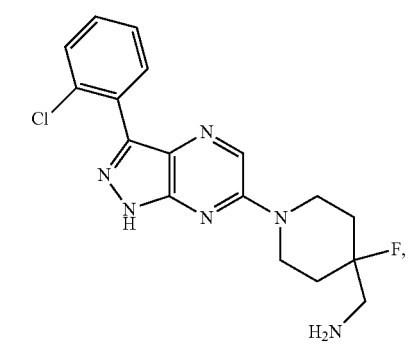
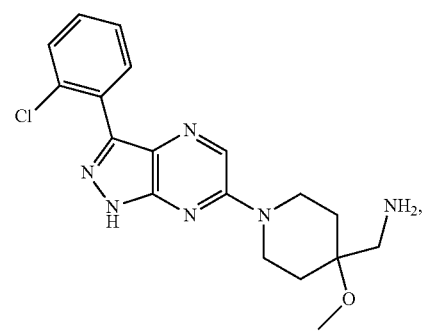
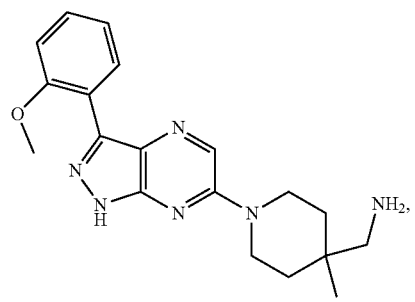
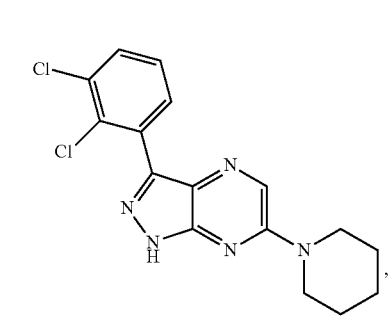
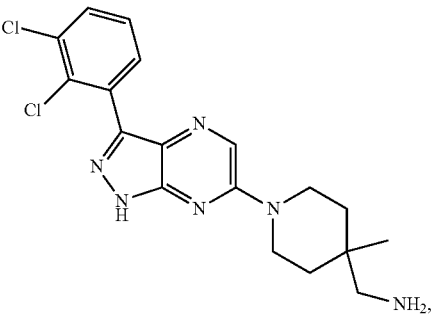
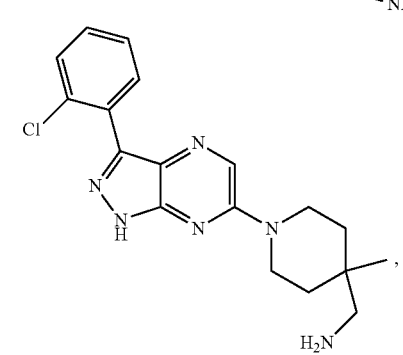
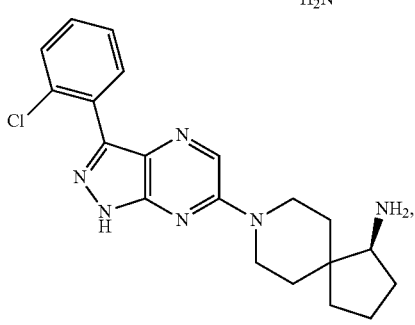

-continued
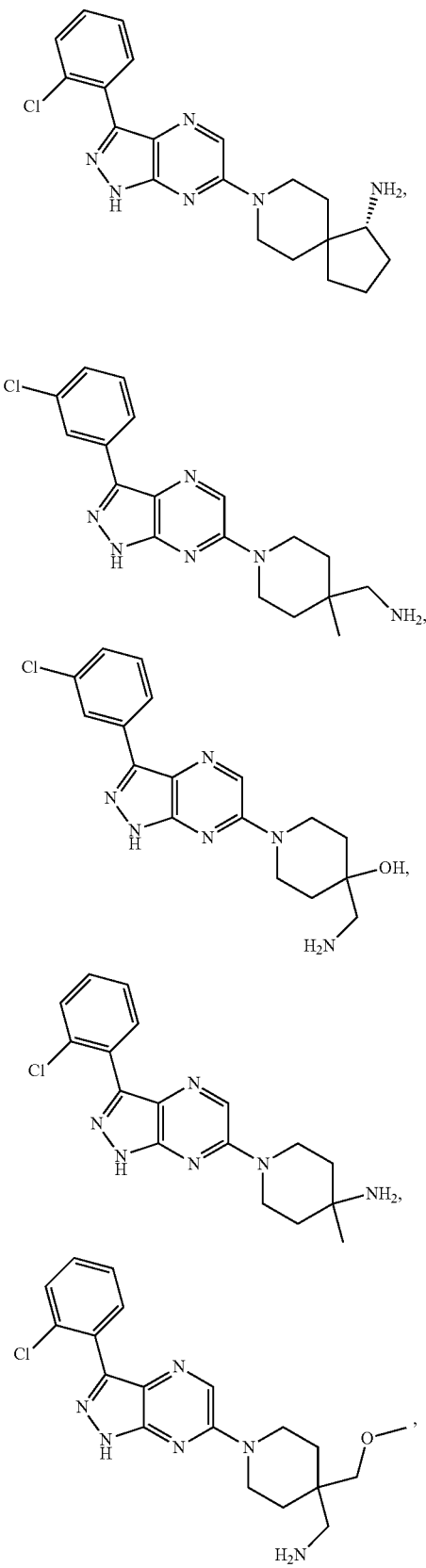
-continued
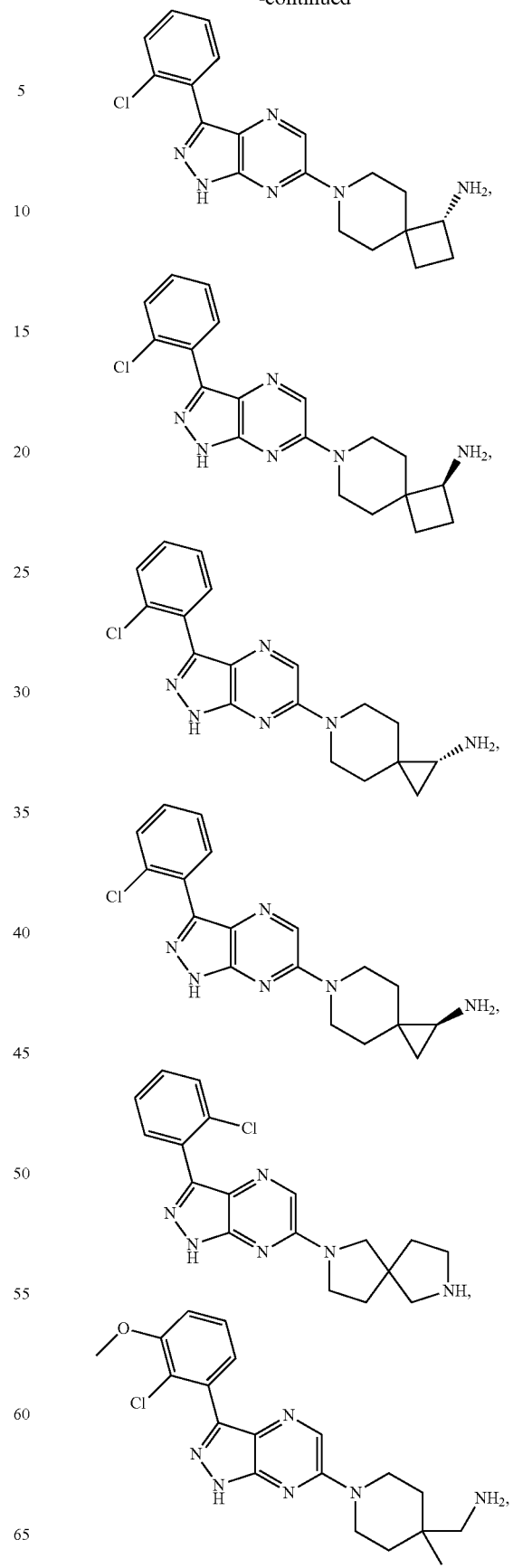

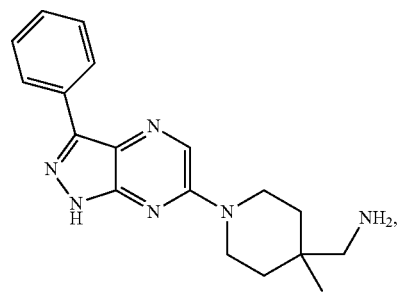
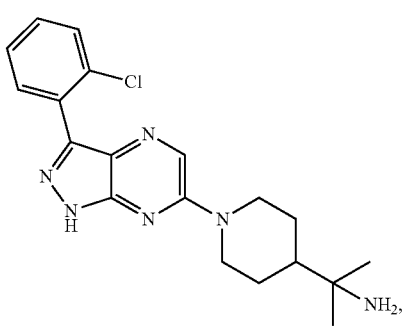
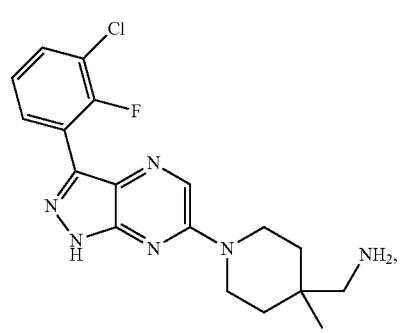
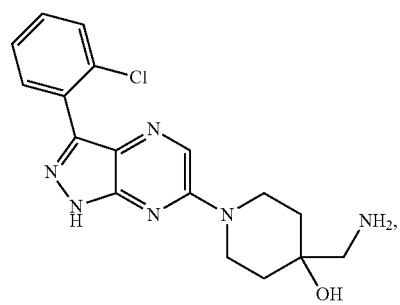
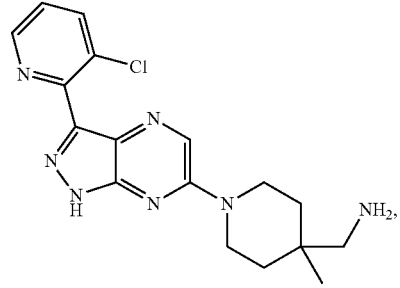
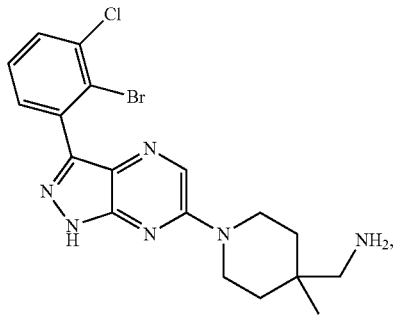
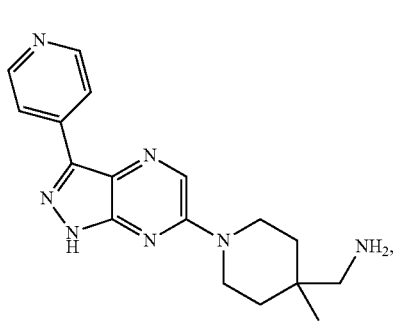
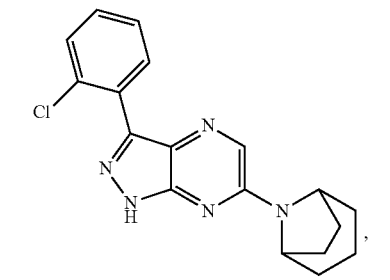
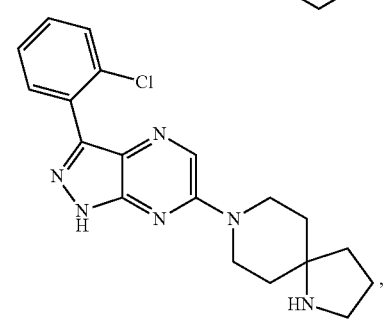
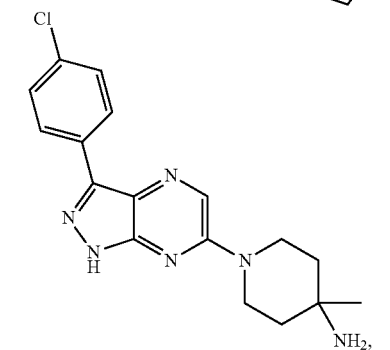

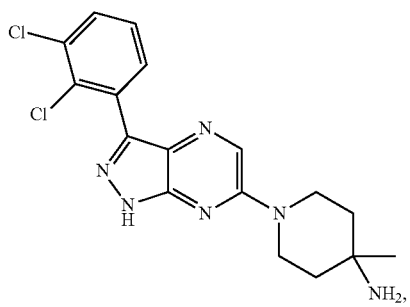
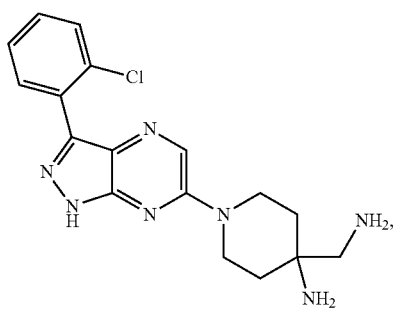
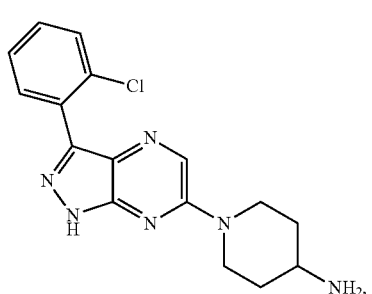
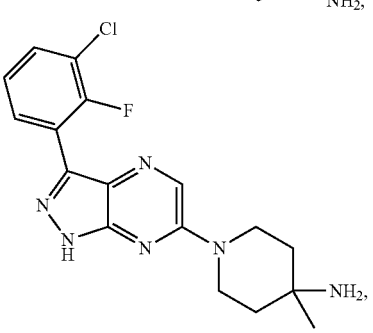
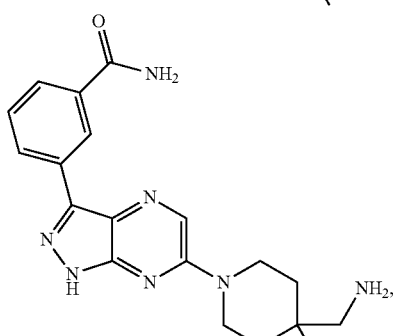
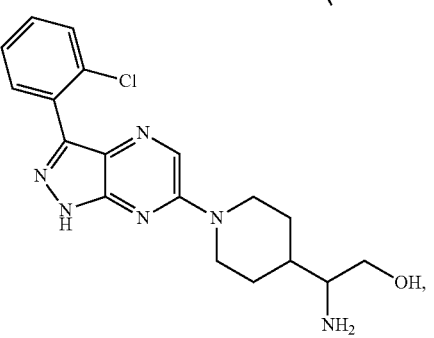

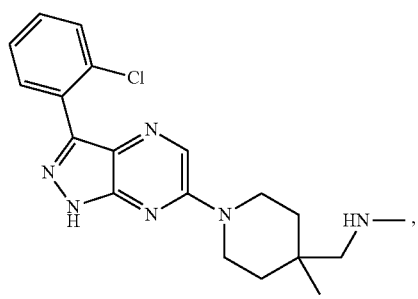
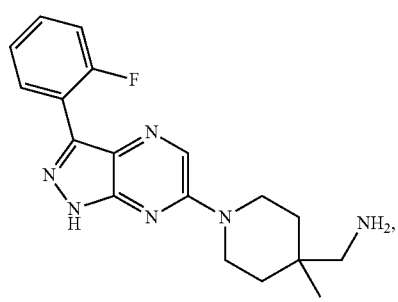
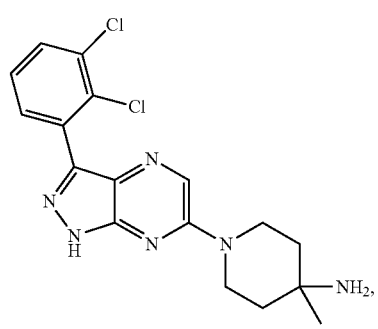
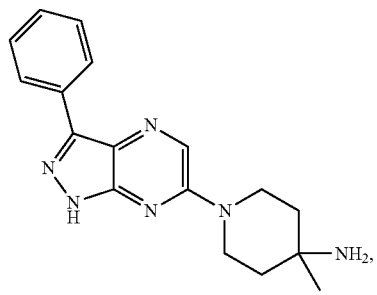
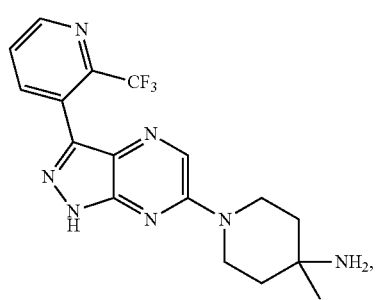
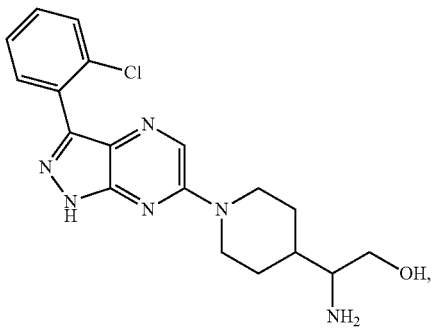
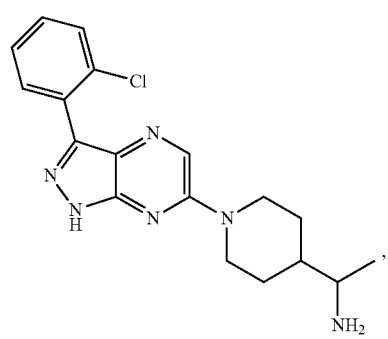
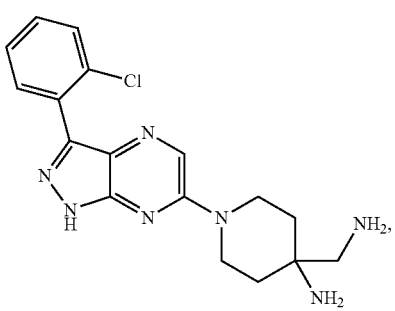
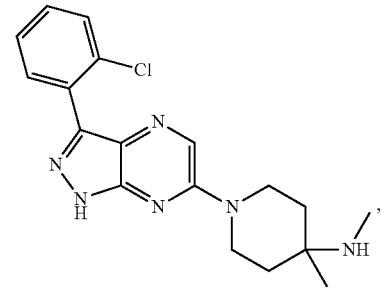
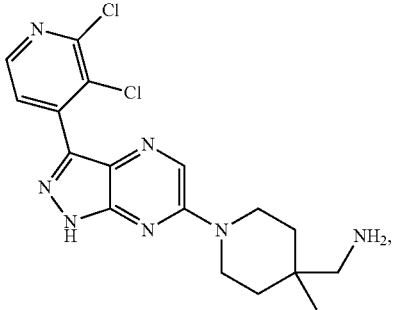

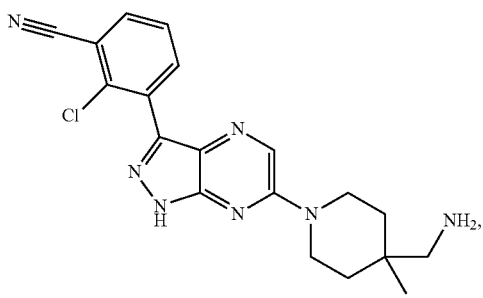
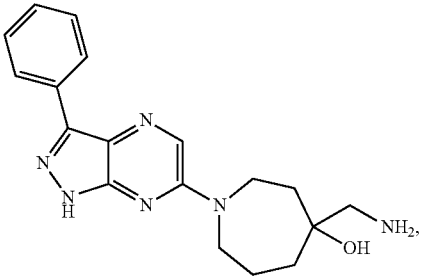
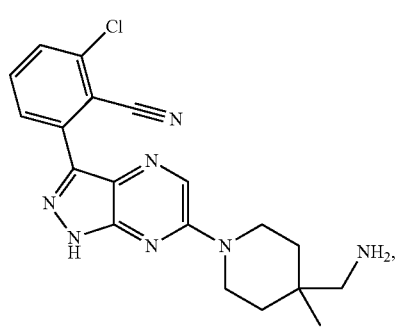
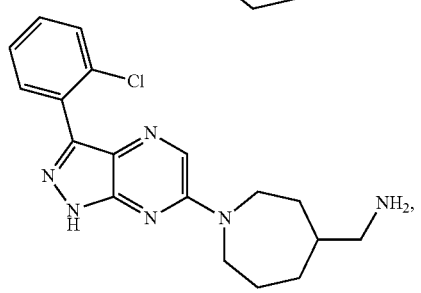
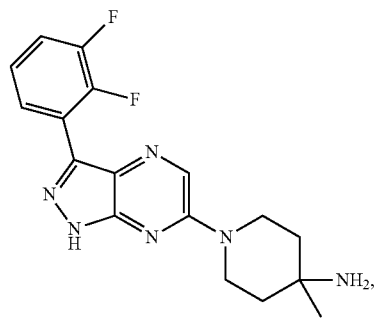
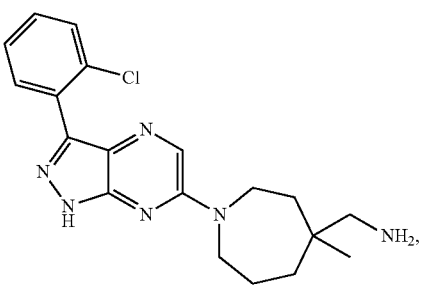
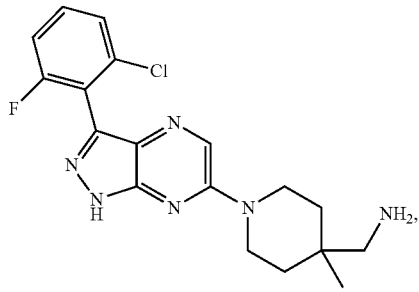
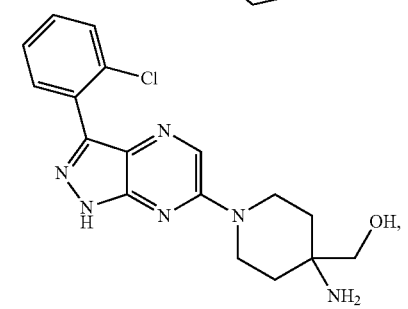
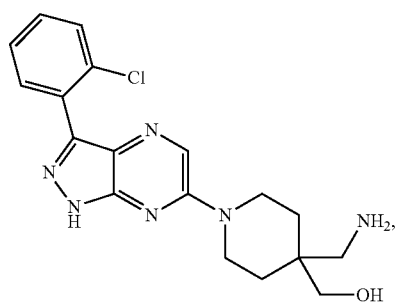
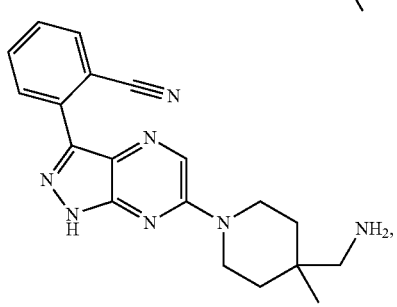

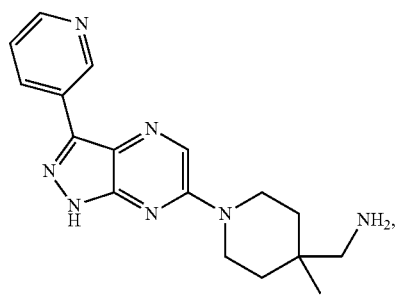
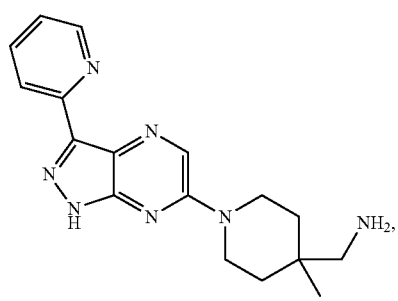
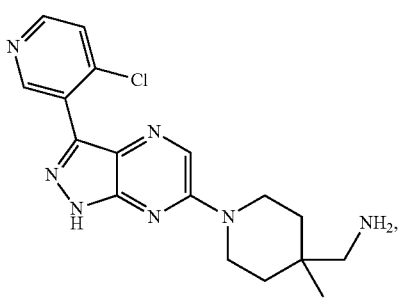
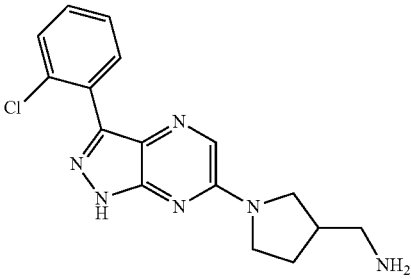
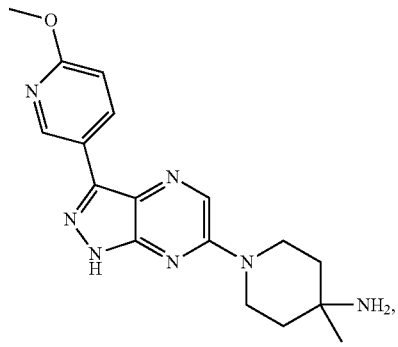
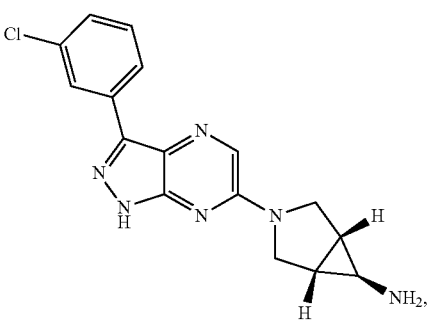
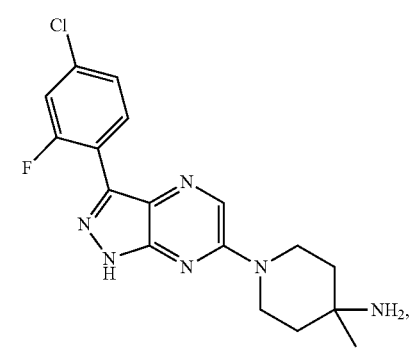
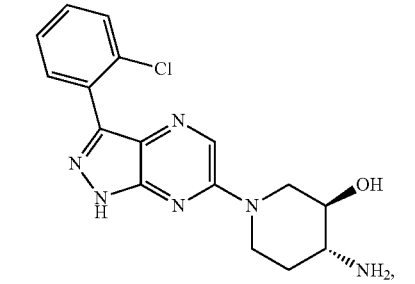
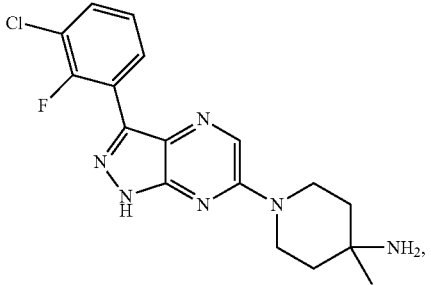
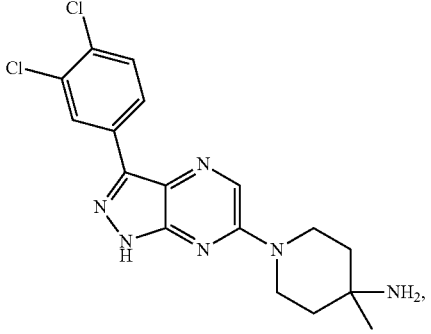

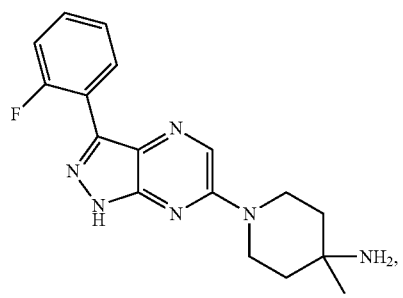
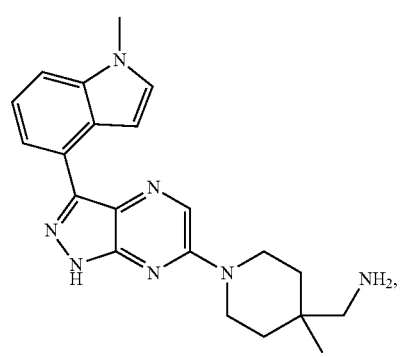
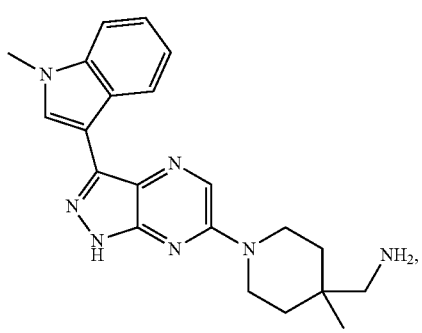
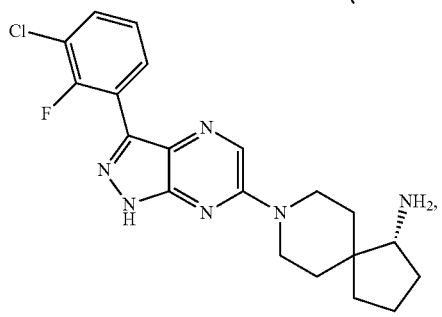
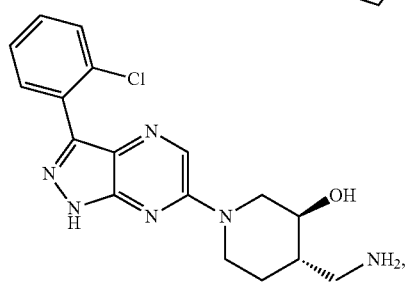
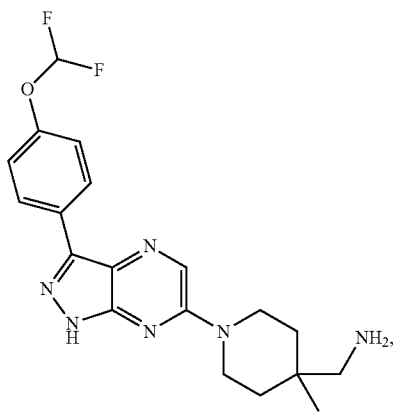
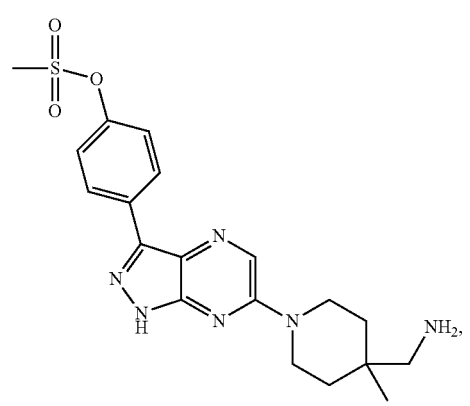
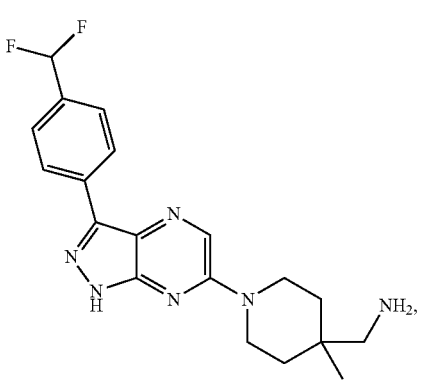
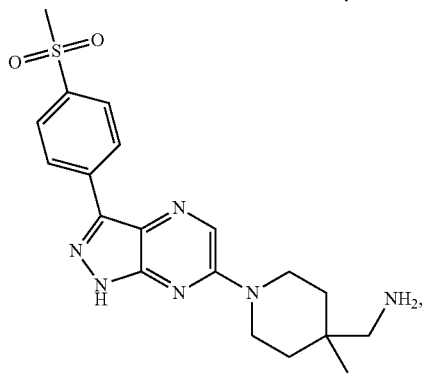

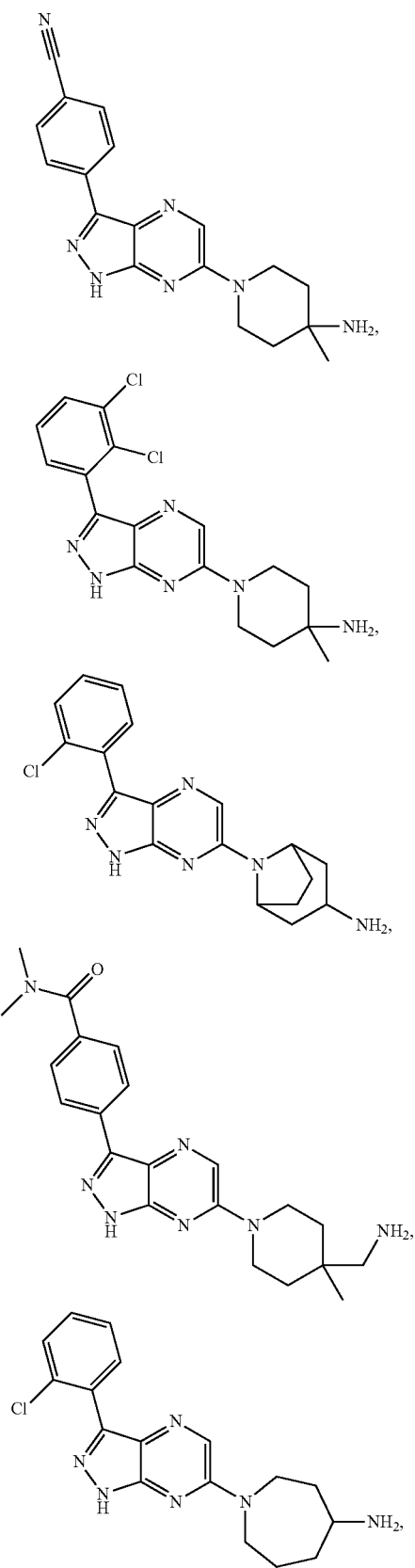
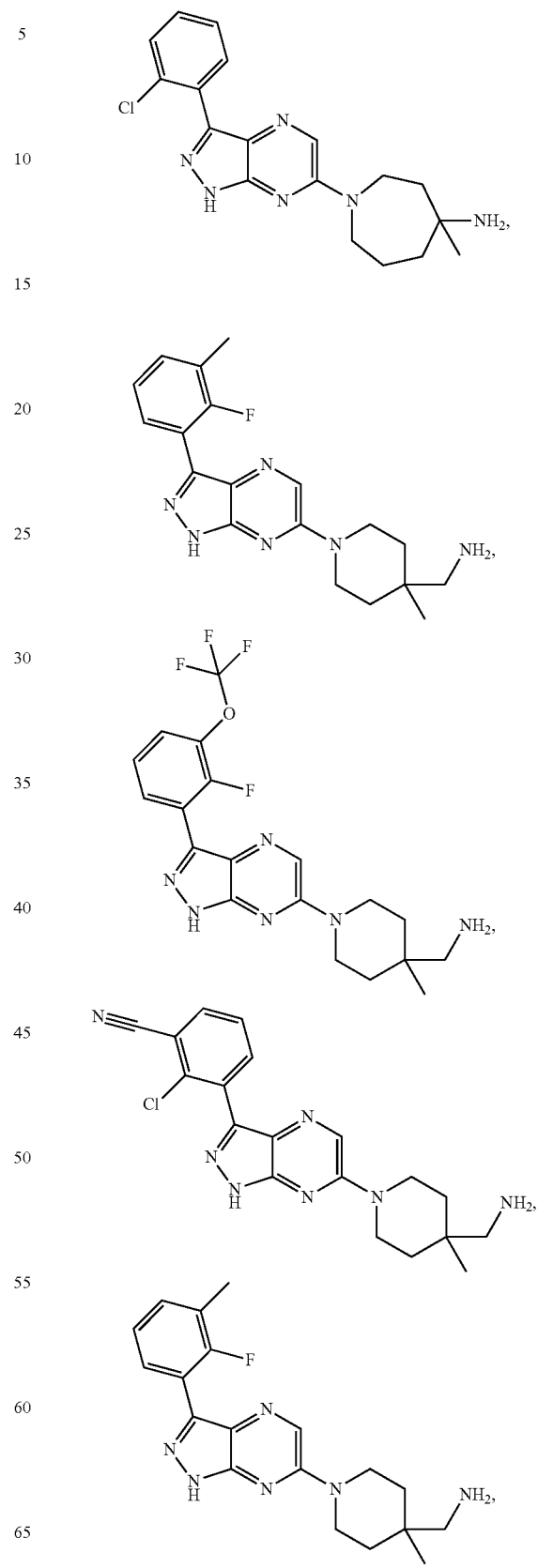

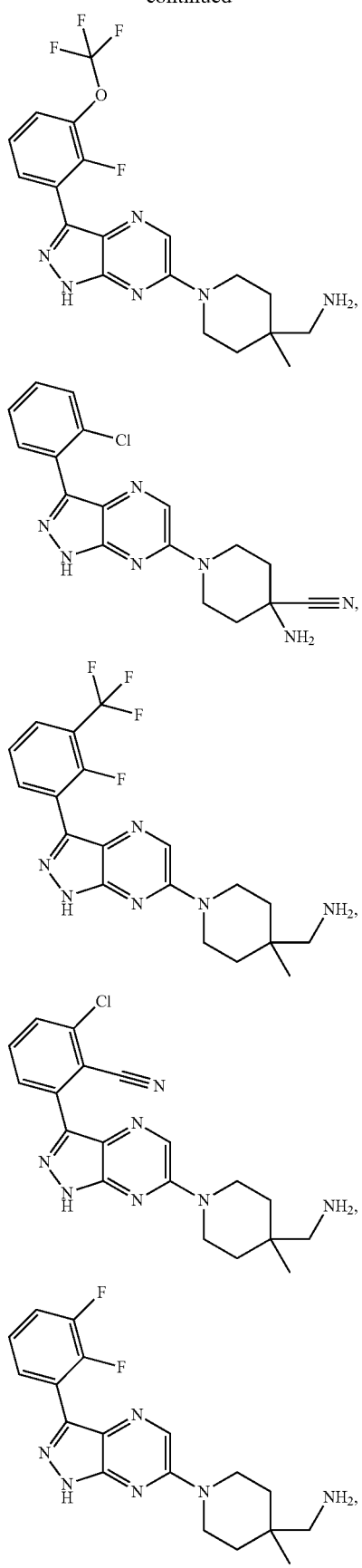
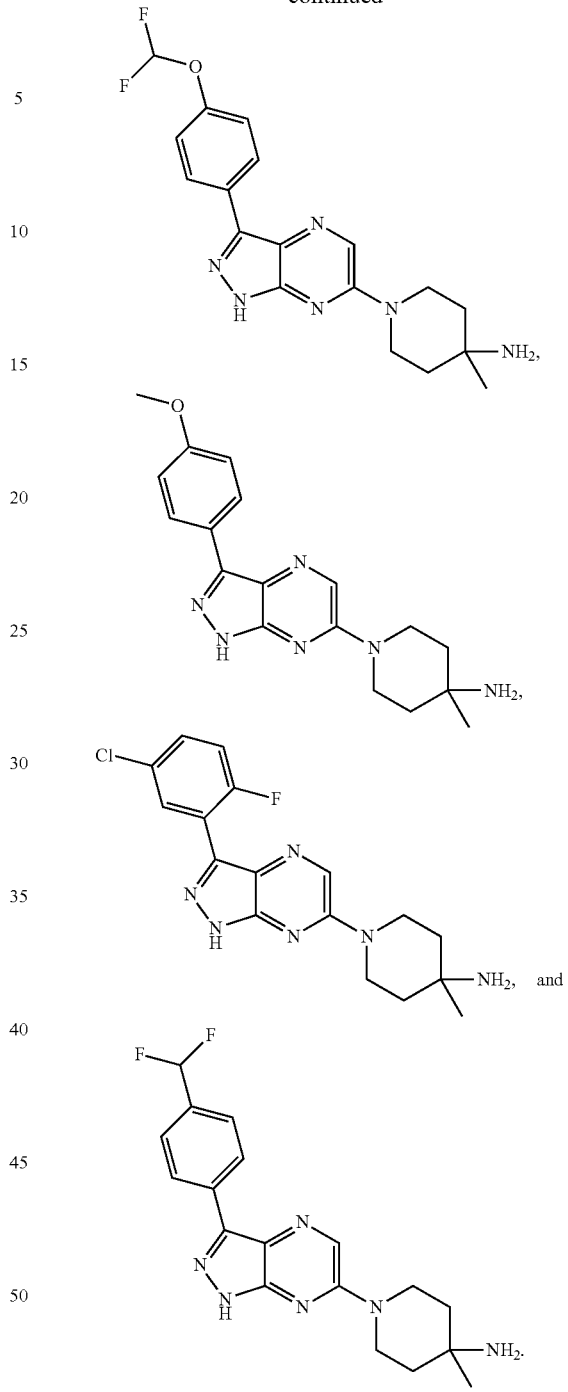

Synthesis

The compounds described herein can be prepared according to known processes. Examples 1-32 represent synthetic schemes for preparing compounds of Formula (I). These schemes are illustrative and are not meant to limit the possible techniques one skilled in the art may use to prepare compounds disclosed herein. Different methods will be evident to those skilled in the art. Additionally, the various steps in the synthesis may be performed in an alternate sequence or order to provide the compound(s). Various modifications to these methods may be envisioned by those skilled in the art to achieve similar results to that of the inventors provided below. For example, optional protecting groups can be used as described, e.g., in Greene et al., Protective Groups in Organic Synthesis (4$^{th}$ ed. 2006).

The compounds of Formula (I) can generally be prepared according to exemplary Scheme 1:

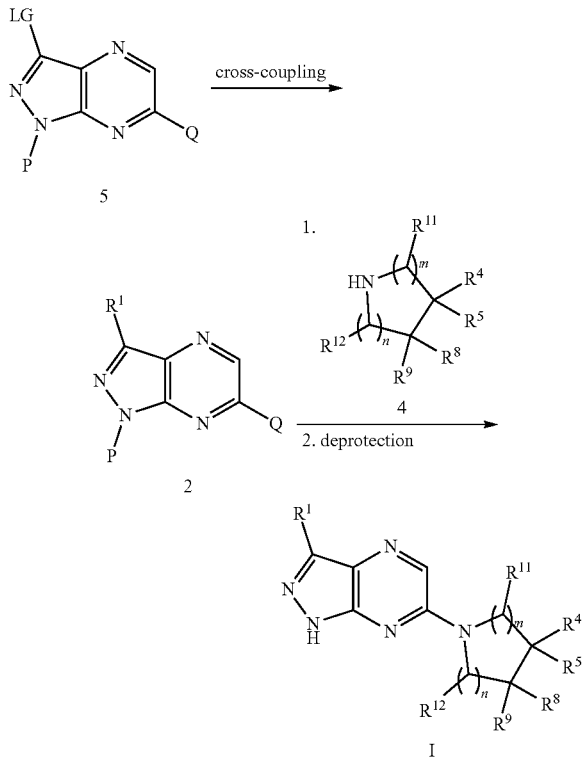

where $R^1$, $R^4$, $R^5$, $R^8$, $R^9$, $R^{11}$, and $R^{12}$ are defined as above, Q is independently a halogen, such as Cl, Br, I, and the like, or any other leaving group, such as $OSO_2Me$, OMs, OTs, OTf, and the like, LG is a leaving group, such as Cl, Br, I, OTs, OTf, and the like, and P is a protecting group, such as tetrahydropyran and the like. Alternative protecting groups that can be used are described, e.g., in Greene et al., Protective Groups in Organic Synthesis (4$^{th}$ ed. 2006).

As shown in Scheme 1, an aryl compound such as 5 undergoes a cross-coupling reaction to provide a compound of Formula 2. The compound of Formula 2 then undergoes a substitution reaction with an amine such as 4, followed by removal of the protecting group to provide a compound of Formula (I). In some embodiments, LG is I. In some embodiments, LG is Cl. In some embodiments, LG is OTf or OTs.

In some embodiments, the cross-coupling reaction is a Suzuki reaction. In some embodiments, the cross-coupling reaction is a Stille reaction. In some embodiments, the cross-coupling reaction is a Negishi coupling. In some embodiments, the cross-coupling reaction is a Hiyama coupling. Other cross-coupling reactions may be employed as would be apparent to one of ordinary skill in the art.

In some embodiments, the protecting group is removed under acidic conditions, such as HBr in AcOH. Conditions for removal of the protecting group will depend on the nature of the protecting group. Conditions for the removal of various protecting groups can be found, e.g., in Greene et al., Protective Groups in Organic Synthesis (4$^{th}$ ed. 2006).

Compounds or compositions of the invention can be useful in applications that benefit from inhibition of SHP2 phosphatase enzymes. For example, inhibition of SHP2 phosphatase may offer a therapeutic approach for the treatment of cancer. (See, e.g., Y.-N. P. Chen et al., in Nature, 2016, doi:10.1038/nature18621; and references cited therein; each of which hereby incorporated by reference in its entirety.) Inhibition of SHP2 phosphatase also has been found to ameliorate the pathogensis of systemic lupus erythematosus. (See, e.g., J. Wang et al., in J. Clin. Invest. 2016, 126, 2077-2092; and references cited therein; each of which hereby incorporated by reference in its entirety.)

In some embodiments, compounds or compositions of the invention can be useful in suppressing tumor cell growth. In some embodiments, compounds or compositions of the invention can be useful in ameliorating the pathogenesis of systemic lupus erythematosus. In some embodiments, compounds or compositions of the invention can be useful in the treatment of various other disorders, including Noonan syndrome (NS), diabetes, neuroblastoma, melanoma, juvenile leukemia, juvenile myelomonocytic leukemia (JMML), chronic myelomonocytic leukemia, acute myeloid leukemia, HER2-positive breast cancer, triple-negative breast cancer, ductal carcinoma of the breast, invasive ductal carcinoma of the breast, non-small cell lung cancer (including adenocarcinoma of the lung), colorectal cancer (SW480, SW620, CACO2, HCT116, HT29 colon cancer cell lines), esophageal cancer, gastric cancer, squamous-cell carcinoma of the head and neck (SCCHN), and neutropenia (Kostmann's syndrome).

In some embodiments, compounds or compositions of the invention can be used in combination with other treatments and/or cancer therapies. For example, compounds or compositions of the invention can be used in combination with, but are not limited to, antibodies, antibody-drug conjugates, kinase inhibitors, immunomodulators, and histone deacetylase inhibitors. The compounds or compositions of the invention can also be used in combination with other treatments and/or cancer therapies as disclosed in WO 2015/107495; and references cited therein; each of which is hereby incorporated by reference in its entirety. For example, the compounds disclosed herein (or pharmaceutical compositions containing them) can be used in the treatment of one or more of the diseases mentioned herein, alone or in combination with another therapeutic agent. For example, a compound of formula (I) can be used in combination with the following agents: BCR-ABL inhibitors: imatinib mesylate; inilotinib hydrochloride; nilotinib; dasatinib; bosutinib; ponatinib; bafetinib; danusertib; saracatinib; N-[2-[(1S,4R)-6-[[4-(Cyclobutylamino)-5-(tjifluoromethyl)-2-pyrimidinyl]amino]-1,2,3,4-tetrahydronaphthalen-1,4-imin-9-yl]-2-oxoethyl]-acetamide. ALK inhibitors: crizotinib; 5-chloro-N4-(2-(isopropylsulfonyl)phenyl)-N2-(2-methoxy-4-(4-(4-methylpiperazin-1-yl)piperidin-1-yl)phenyl)pyrimidine-2,4-diamine, ceritinib, alectinib, brigatinib, entrecinib. BRAF inhibitors: vemurafenib and dabrafenib. FGFR inhibitors: infigratinib, dovitinib, erdafitinib, BLU-554, AZD4547. FLT3 inhibitors: sunitinib malate; midostaurin; tanutinib; sorafenib, lestaurtinib, quizartinib and crenolanib. MEK Inhibitors—trametinib, combimetinib, binimetinib, selumetinib. VEGF receptor inhibitors: bevacizumab, axitinib, Aflibercept, (N-methyl-2-[[3-[(E)-2-pyridin-2-ylethenyl]-1H-indazol-6-yl]sulfanyl]benzamide, brivanib alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, motesanib (N-(2,3-dihydro-3,3-dimethyl- 1H-indol-6-yl)-2-[(4-pyridinylmethyl)amino]-3-pyridinecarboxamide, pasireotide, sorafenib. Tyrosine kinase inhibitors: erlotinib hydrochloride, linifanib, sunitinib malate, pazopanib. Epidermal growth factor receptor (EGFR) inhibitors: Gefitnib, osimertinib, cetuximab, panitumumab. HER2 receptor inhibitors: trastuzumab, neratinib, lapatinib or lapatinib ditosylate. MET inhibitors: crizotinib, cabozantinib. CD20 antibodies: rituximab, tositumomab, ofatumumab. DNA Synthesis inhibitors: capecitabine, gemcitabine hydrochloride, nelarabine, hydroxycarbamide. Antineoplastic agents: oxaliplatin. HER dimerization inhibitors: pertuzumab. Human Granulocyte colony-stimulating factor (G-CSF) modulators: Filgrastim. Immunomodulators: Afutuzumab, lenalidomide, thalidomide. CD40 inhibitors: Dacetuzumab. Pro-apoptotic receptor agonists (PARAs): Dulanermin. Heat Shock Protein (HSP) inhibitors: Tanespimycin (17-allylamino-17-demethoxygeldanamycin). Hedgehog antagonists: 2-chloro-N-[4-chloro-3-(2-pyridinyl)phenyl]-4-(methylsulfonyl)-benzamide. Proteasome inhibitors: Bortezomib. PI3K inhibitors: 4-[2-(1H-Indazol-4-yl)-6-[[4-(methylsulfonyl)piperazin-1-yl]methyl]thieno[3,2-d]pyrimidin-4-yl]mo choline, 2-Methyl-2-[4-[3-methyl-2-oxo-8-(quinolin-3-yl)-2,3-dihydroimidazo [4,5-c]quinolin-1-yl]phenyl]propiocyano, buparlisib, taselisib, idelalisib, duvelisib, TGR 1202. Phospholipase A2 inhibitors: Anagrelide. BCL-2 inhibitors: 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl] amino]-3-[(trifluoromethyl)sulfonyl]phenyl] sulfonyl]benzamide. Mitogen-activated protein kinase kinase (MEK) inhibitors: XL-518. Aromatase inhibitors: Exemestane, letrozole, anastrozole, faslodex, tamoxifen. Topoisomerase I inhibitors: Irinotecan, topotecan hydrochloride. Topoisomerase II inhibitors: etoposide, teniposide. mTOR inhibitors: Temsirolimus, ridaforolimus, everolimus. Osteoclastic bone resorption inhibitors: 1-Hydroxy-2-imidazol-1-yl-phosphonoethyl) phosphonic acid monohydrate. CD33 Antibody Drug Conjugates: Gemtuzumab ozogamicin. CD22 Antibody Drug Conjugates: Inotuzumab ozogamicin. CD20 Antibody Drug Conjugates: Ibritumomab tiuxetan. Somatostain analogs: octreotide. Synthetic Interleukin-11 (IL-11): oprelvekin. Synthetic erythropoietin: Darbepoetin alfa. Receptor Activator for Nuclear Factor κ B (RANK) inhibitors: Denosumab. Thrombopoietin mimetic peptides: Romiplostim. Cell growth stimulators: Palifermin. Anti-Insulin-like Growth Factor-1 receptor (IGF-1R) antibodies: Figitumumab. Anti-CSI antibodies: Elotuzumab. CD52 antibodies: Alemtuzumab. CTLA-4 inhibitors: Tremelimumab, ipilimumab. PD1 inhibitors: Nivolumab; pembrolizumab; an immunoadhesin; Pidilizumab; and AMP-224. PDL1 inhibitors: MSB0010718C; YW243.55.S70, MPDL3280A; MEDI-4736, MSB-0010718C, or MDX-1105. LAG-3 inhibitors: BMS-986016. GITR agonists: GITR fusion proteins and anti-GITR antibodies. Histone deacetylase inhibitors (HDI): Voninostat. Anti-CTLA4 antibodies: Tremelimumab; and Ipilimumab. Alkylating agents: Temozolomide, dactinomycin, melphalan, altretamine carmustine, bendamustine, busulfan, carboplatin, lomustine, cisplatin, chlorambucil, cyclophosphamide, dacarbazine, altretamine, ifosfamide, procarbazine, mechlorethamine, mustine and mechloroethamine hydrochloride, streptozocin, thiotepa. Biologic response modifiers: bacillus calmette-guerin, denileukin diftitox. Anti-tumor antibiotics: doxorubicin, bleomycin, daunorubicin, daunorubicin liposomal, mitoxantrone, epirubicin, idarubicin, mitomycin C. Anti-microtubule agents: Estramustine. Cathepsin K inhibitors: Odanacatib. Epothilone B analogs: Ixabepilone. TpoR agonists: Eltrombopag. Antimitotic agents: Docetaxel. Adrenal steroid inhibitors: aminoglutethimide. Anti-androgens: Nilutamide, Androgen Receptor inhibitors: enzalutamide, abiraterone acetate, orteronel, galeterone, and seviteronel, bicalutamide, flutamide. Androgens: Fluoxymesterone. CDK1 inhibitors: Alvocidib, palbociclib, ribociclib, trilaciclib, abemaciclib. Gonadotropin-releasing hormone (GnRH) receptor agonists: Leuprolide or leuprolide acetate. Taxane anti-neoplastic agents: Cabazitaxel (1-hydroxy^, 10-dimethoxy-9-oxo-5,20-epoxytax-11-ene-2a,4,13a-triyl-4-acetate-2-benzoate-13-[(2R,3S)-3-{[(tert-butoxy)carbonyl] amino}-2-hydroxy-3-phenylpropanoate), larotaxel ((2α,3ζ,4α,5β,7α,10β,13α)-4,10-bis(acetyloxy)-13-({(2R,3S)-3-[(tert-butoxycarbonyl) amino]-2-hydroxy-3-phenylpropanoyl} oxy)-1-hydroxy-9-oxo-5,20-epoxy-7,19-cyclotax-1 1-en-2-yl benzoate). 5HT1a receptor agonists: Xaliproden (also known as SR57746, 1-[2-(2-naphthyl)ethyl]-4-[3-(trifluoromethyl)phenyl]-1,2,3,6-tetrahydropyridine. HPC vaccines: Cervarix® sold by GlaxoSmithKline, Gardasil® sold by Merck; Iron Chelating agents: Deferasinox. Anti-metabolites: Claribine (2-chlorodeoxyadenosine), 5-fluorouracil, 6-thioguanine, pemetrexed, cytarabine, cytarabine liposomal, decitabine, hydroxyurea, fludarabine, floxuridine, cladribine, methotrexate, pentostatin. Bisphosphonates: Pamidronate. Demethylating agents: 5-azacitidine, decitabine.

Plant Alkaloids: Paclitaxel protein-bound; vinblastine, vincristine, vinorelbine, paclitaxel. Retinoids: Alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Claras®, Decutan@, Isotane®, Izotech®, Oratane®, Isotret®, and Sotret®), bexarotene (sold under the tradename Targretin®). Glucocorticosteroids: Hydrocortisone (also known as cortisone, hydrocortisone sodium succinate, hydrocortisone sodium phosphate, and sold under the tradenames Ala-Cort@, Hydrocortisone Phosphate, Solu-Cortef®, Hydrocort Acetate® and Lanacort®), dexamethazone ((8S,9R,10S,11S,13S,14S,16R,17R)-9-fluoro-11,17-dihydroxy-17-(2-hydroxy acetyl)-10,13,16-trimethyl-6,7,8,9,10, 11,12, 13, 14,15,16,17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®). Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®). Estrogen receptor downregulators: Fulvestrant (sold under the tradename Faslodex®). Anti-estrogens: tamoxifen (sold under the tradename Novaldex®). Toremifene (sold under the tradename Fareston®). Selective estrogen receptor modulators (SERMs): Raloxifene (sold under the tradename Evista®). Leutinizing hormone releasing hormone (LHRH) agonists: Goserelin (sold under the tradename Zoladex®); Progesterones: megestrol (also known as megestrol acetate, sold under the tradename Megace®); Miscellaneous cytotoxic agents: Arsenic trioxide (sold under the tradename Trisenox®), asparaginase (also known as L-asparaginase, Erwinia L-asparaginase, sold under the tradenames Elspar® and Kidrolase®). Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid). Immune checkpoint inhibitors: The term "immune checkpoints" refers to a group of molecules on the cell surface of CD4 and CD8 T cells. Immune checkpoint molecules include, but are not limited to, Programmed Death 1 (PD-1), Cytotoxic T-Lymphocyte Antigen 4 (CTLA-4), B7H1, B7H4, OX-40, CD 137, CD40, and LAG3. Immunotherapeutic agents which can act as immune checkpoint inhibitors useful in the methods of the present invention, include, but are not limited to, inhibitors of PD-L1, PD-L2, CTLA4, TIM3, LAG3, VISTA, BTLA, TIGIT, LAIR1, CD 160, 2B4 and/or TGFR beta.

The compounds described herein can function as allosteric inhibitors and block the activation of SHP2 by targeting the auto-inhibited conformation of SHP2.

The compounds described herein can also inhibit SHP2 function through incorporation into agents that catalyze the destruction of SHP2. For example, the compounds can be incorporated into proteolysis targeting chimeras (PROTACs). A PROTAC is a bifunctional molecule, with one portion capable of engaging an E3 ubiquitin ligase, and the other portion having the ability to bind to a target protein meant for degradation by the cellular protein quality control machinery. Recruitment of the target protein to the specific E3 ligase results in its tagging for destruction (i.e., ubiquitination) and subsequent degradation by the proteasome. Any E3 ligase can be used. The portion of the PROTAC that engages the E3 ligase is connected to the portion of the PROTAC that engages the target protein via a linker which consists of a variable chain of atoms. Recruitment of SHP2 to the E3 ligase will thus result in the destruction of the SHP2 protein. The variable chain of atoms can include, for example, rings, heteroatoms, and/or repeating polymeric units. It can be rigid or flexible. It can be attached to the two portions described above using standard techniques.

The compounds described herein can be linked to one end of a variable chain, while the other end of the variable chain can be bound to the E3 ligase. Recruitment of SHP2 to the ligase will thus result in the destruction of the SHP2 protein.

In some embodiments, compounds or compositions of the invention can be used in combination with an antibody. In some embodiments, compounds or compositions of the invention can be used in combination with an antibody-drug conjugate. In some embodiments, compounds or compositions of the invention can be used in combination with a kinase inhibitor. In some embodiments, compounds or compositions of the invention can be used in combination with an immunomodulator. In some embodiments, compounds or compositions of the invention can be used in combination with a histone deacetylase inhibitor.

In some embodiments, compounds of Formula (I) can be administered to a subject in need of treatment at dosages ranging from about 0.0001 mg to about 100 mg/kg body weight of the subject to be treated per day, such as from about 1.0 to 10 mg/kg. However, additional variations are within the scope of the invention.

The compound of Formula (I) can be administered alone or in combination with pharmaceutically acceptable carriers, such as diluents, fillers, aqueous solution, and even organic solvents. The compound and/or compositions of the invention can be administered as a tablet, powder, lozenge, syrup, injectable solution, and the like. Additional ingredients, such as flavoring, binder, excipients, and the like are within the scope of the invention.

In some embodiments, pharmaceutically acceptable compositions can contain a compound of Formula (I) and/or a pharmaceutically acceptable salt thereof at a concentration ranging from about 0.01 to about 2.0 wt %, such as 0.01 to about 1 wt % or about 0.05 to about 0.5 wt %. The composition can be formulated as a solution, suspension, ointment, or a capsule, and the like. The pharmaceutical composition can be prepared as an aqueous solution and can contain additional components, such as preservatives, buffers, tonicity agents, antioxidants, stabilizers, viscosity-modifying ingredients and the like.

In some embodiments, the present invention provides for the use of pharmaceutical compositions and/or medicaments comprised of a compound of Formula (I), or a pharmaceutically acceptable salt thereof, in a method of treating a disease state, and/or condition caused by or related to SHP2 phosphatase.

In some embodiments, the method of treatment comprises the steps of: i) identifying a subject in need of such treatment; (ii) providing a compound of Formula (I), or a pharmaceutically acceptable salt thereof; and (iii) administering said compound of Formula (I) in a therapeutically effective amount to treat, suppress and/or prevent the disease state or condition in a subject in need of such treatment.

In some embodiments, the method of treatment comprises the steps of: i) identifying a subject in need of such treatment; (ii) providing a composition comprising a compound of Formula (I), or a pharmaceutically acceptable salt thereof; and (iii) administering said composition in a therapeutically effective amount to treat, suppress and/or prevent the disease state or condition in a subject in need of such treatment.

In some embodiments, the subject is an animal. Animals include all members of the animal kingdom, but are not limited to humans, mice, rats, cats, monkeys, dogs, horses, and swine. In some embodiments, the subject is a human. In some embodiments, the subject is a mouse, a rat, a cat, a monkey, a dog, a horse, or a pig.

In some embodiments, the compound or composition is administered orally. In some embodiments, the compound or composition is administered intravenously.

In some embodiments, the methods comprise administering to the subject an effective amount of a compound of Formula (I), or a pharmaceutically acceptable salt thereof; or a composition comprising a compound of Formula (I), or a pharmaceutically acceptable salt thereof, and a pharmaceutically acceptable carrier.

Pharmaceutically acceptable carriers are well-known to those skilled in the art, and include, e.g., adjuvants, diluents, excipients, fillers, lubricants and vehicles. In some embodiments, the carrier is a diluent, adjuvant, excipient, or vehicle. In some embodiments, the carrier is a diluent, adjuvant, or excipient. In some embodiments, the carrier is a diluent or adjuvant. In some embodiments, the carrier is an excipient. Often, the pharmaceutically acceptable carrier is chemically inert toward the active compounds and is non-toxic under the conditions of use. Examples of pharmaceutically acceptable carriers may include, e.g., water or saline solution, polymers such as polyethylene glycol, carbohydrates and derivatives thereof, oils, fatty acids, or alcohols. Non-limiting examples of oils as pharmaceutical carriers include oils of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in e.g., Remington's: The Science and Practice of Pharmacy, 22nd Ed. (Allen, Loyd V., Jr ed., Pharmaceutical Press (2012)); Modern Pharmaceutics, $5^{th}$ Ed. (Alexander T. Florence, Juergen Siepmann, CRC Press (2009)); Handbook of Pharmaceutical Excipients, $7^{th}$ Ed. (Rowe, Raymond C.; Sheskey, Paul J.; Cook, Walter G.; Fenton, Marian E. eds., Pharmaceutical Press (2012)) (each of which hereby incorporated by reference in its entirety).

In some embodiments, the method of treatment, prevention and/or suppression of a condition related to SHP2 phosphatase comprises the steps of: i) identifying a subject in need of such treatment; (ii) providing a compound of Formula (I), or a pharmaceutically acceptable salt thereof; or a composition comprising a compound of Formula (I), or a pharmaceutically acceptable salt thereof, and a pharmaceutically acceptable carrier; and (iii) administering said compound or composition in a therapeutically effective amount to treat, prevent and/or suppress the disease state or condition related to SHP2 phosphatase in a subject in need of such treatment.

In some embodiments, the compounds of the invention are formulated into pharmaceutical compositions for administration to subjects in a biologically compatible form suitable for administration in vivo. According to another aspect, the present invention provides a pharmaceutical composition comprising a compound of Formula I in admixture with a pharmaceutically acceptable diluent and/or carrier. The pharmaceutically-acceptable carrier is "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, e.g., detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sufate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used, amine salts of formula $N+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine.

When administered to a subject, the compound of Formula I and pharmaceutically acceptable carriers can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present invention are prepared by methods well-known in the pharmaceutical arts. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Additionally, the compounds and/or compositions of the present invention are administered to a human or animal subject by known procedures including oral administration, sublingual or buccal administration. In some embodiments, the compound and/or composition is administered orally.

For oral administration, a formulation of the compounds of the invention may be presented in dosage forms such as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, e.g., sweetening agents such as fructose, aspartame or saccharin; flavoring agents such as peppermint, oil of wintergreen, or cherry; coloring agents; and preservative agents, to provide a pharmaceutically palatable preparation.

In some embodiments, the composition is in unit dose form such as a tablet, capsule or single-dose vial. Suitable unit doses, i.e., therapeutically effective amounts, may be determined during clinical trials designed appropriately for each of the conditions for which administration of a chosen compound is indicated and will, of course, vary depending on the desired clinical endpoint.

In accordance with the methods of the present invention, the compounds of the invention are administered to the subject in a therapeutically effective amount, e.g., to reduce or ameliorate symptoms related to SHP2 phosphatase activity in the subject. This amount is readily determined by the skilled artisan, based upon known procedures, including analysis of titration curves established in vivo and methods and assays disclosed herein.

In some embodiments, the methods comprise administration of a therapeutically effective dosage of the compounds of the invention. In some embodiments, the therapeutically effective dosage is at least about 0.0001 mg/kg body weight, at least about 0.001 mg/kg body weight, at least about 0.01 mg/kg body weight, at least about 0.05 mg/kg body weight, at least about 0.1 mg/kg body weight, at least about 0.25 mg/kg body weight, at least about 0.3 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. It will be recognized that any of the dosages listed herein may constitute an upper or lower dosage range, and may be combined with any other dosage to constitute a dosage range comprising an upper and lower limit.

In some embodiments, the therapeutically effective dosage is in the range of about 0.1 mg to about 10 mg/kg body weight, about 0.1 mg to about 6 mg/kg body weight, about 0.1 mg to about 4 mg/kg body weight, or about 0.1 mg to about 2 mg/kg body weight.

In some embodiments the therapeutically effective dosage is in the range of about 1 to 500 mg, about 2 to 150 mg, about 2 to 120 mg, about 2 to 80 mg, about 2 to 40 mg, about 5 to 150 mg, about 5 to 120 mg, about 5 to 80 mg, about 10 to 150 mg, about 10 to 120 mg, about 10 to 80 mg, about 10 to 40 mg, about 20 to 150 mg, about 20 to 120 mg, about 20 to 80 mg, about 20 to 40 mg, about 40 to 150 mg, about 40 to 120 mg or about 40 to 80 mg.

In some embodiments, the methods comprise a single dosage or administration (e.g., as a single injection or deposition). Alternatively, the methods comprise administration once daily, twice daily, three times daily or four times daily to a subject in need thereof for a period of from about 2 to about 28 days, or from about 7 to about 10 days, or from about 7 to about 15 days, or longer. In some embodiments, the methods comprise chronic administration. In yet other embodiments, the methods comprise administration over the course of several weeks, months, years or decades. In still other embodiments, the methods comprise administration over the course of several weeks. In still other embodiments, the methods comprise administration over the course of several months. In still other embodiments, the methods comprise administration over the course of several years. In still other embodiments, the methods comprise administration over the course of several decades.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens.

The precise dose to be employed in the compositions will also depend on the route of administration, and should be decided according to the judgment of the practitioner and each subject's circumstances. In specific embodiments of the invention, suitable dose ranges for oral administration of the compounds of the invention are generally about 1 mg/day to about 1000 mg/day. In some embodiments, the oral dose is about 1 mg/day to about 800 mg/day. In some embodiments, the oral dose is about 1 mg/day to about 500 mg/day. In some embodiments, the oral dose is about 1 mg/day to about 250 mg/day. In some embodiments, the oral dose is about 1 mg/day to about 100 mg/day. In some embodiments, the oral dose is about 5 mg/day to about 50 mg/day. In some embodiments, the oral dose is about 5 mg/day. In some embodiments, the oral dose is about 10 mg/day. In some embodiments, the oral dose is about 20 mg/day. In some embodiments, the oral dose is about 30 mg/day. In some embodiments, the oral dose is about 40 mg/day. In some embodiments, the oral dose is about 50 mg/day. In some embodiments, the oral dose is about 60 mg/day. In some embodiments, the oral dose is about 70 mg/day. In some embodiments, the oral dose is about 100 mg/day. It will be recognized that any of the dosages listed herein may constitute an upper or lower dosage range, and may be combined with any other dosage to constitute a dosage range comprising an upper and lower limit.

Any of the compounds and/or compositions of the invention may be provided in a kit comprising the compounds and/or compositions. Thus, in some embodiments, the compound and/or composition of the invention is provided in a kit.

Those skilled in the art will recognize, or be able to ascertain using no more than routine experimentation, many equivalents to the specific embodiments of the invention described herein. Such equivalents are intended to be within the scope of the present invention.

The invention is further described by the following non-limiting Examples.

EXAMPLES

Examples are provided below to facilitate a more complete understanding of the invention. The following examples serve to illustrate the exemplary modes of making and practicing the invention. However, the scope of the invention is not to be construed as limited to specific embodiments disclosed in these Examples, which are illustrative only.

Instrumentation and Methods:

Reactions were monitored and final products were characterized using one of the following methods. LCMS standard conditions were: Waters HPLC system equipped with an Alliance 2695 main module, Waters 996 diode array detector and ZQ micromass ESI-MS detector. Mobile phase A: H$_2$O (10.0 mM NH$_4$HCO$_2$), mobile phase B: CH$_3$CN. HPLC conditions were: XBridge C18 column, 4.6×30 mm, 3.5 μm, 0.0-0.2 min. isocratic (5% B), 0.2-2.0 min. gradient (5-100% B), 3.0-3.0 min. isocratic (100% B); flow rate: 3.0 mL/min; UV channel: 254 nm.

Purification of some racemic products was performed using semi preparative HPLC A, semi preparative HPLC B, or semi preparative SFC. Semi preparative HPLC A: Gilson 215 system equipped with a Waters 996 diode array detector and a Waters 2525 pump. Semi preparative HPLC B: Waters 2767 system equipped with a Waters 996 diode array detector, 2 X Waters 515 pumps, a Waters 2525 pump and a ZQ micromass ESI-MS detector. Semi preparative SFC: Mettler Toledo Minigram SFC equipped with a Knauer K-2501 UV detector and an Alcott Model 1719 Autosampler.

Product homogeneity and enantiomeric excess determination were performed using Analytical HPLC A: Agilent 1100 HPLC system equipped with an Agilent G1315A diode array detector.

Nuclear Magnetic resonance: NMR spectra were recorded on Bruker Avance II Ultra shield spectrometer (500 MHz).

Example 1: Preparation of benzyl 8-azaspiro[4.5]decan-1-ylcarbamate

Benzyl 8-azaspiro[4.5]decan-1-ylcarbamate was prepared as schematically illustrated below.

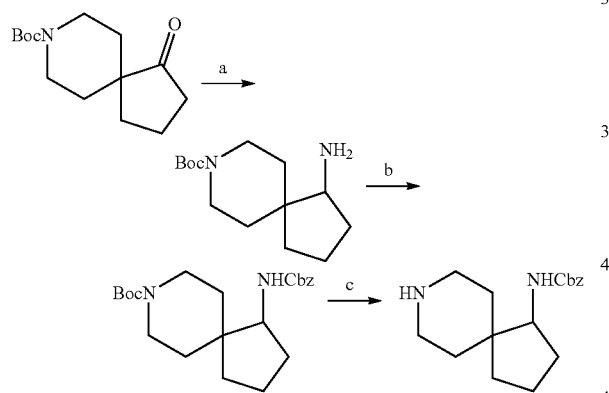

Step a: A mixture tert-butyl 1-oxo-8-azaspiro[4.5]decane-8-carboxylate (1000 mg, 3.94 mmol) and ammonium acetate (3037 mg, 39.4 mmol) in ethanol (10 mL) was stirred at room temperature for 5 min. Sodium cyanoborohydride (297 mg, 4.73 mmol) was added in three parts. The mixture was heated under micro-wave for 99 min at 110° C. The residue was dissolved in water and ethyl acetate and stirred vigorously. The ethyl acetate phase was separated, dried (MgSO$_4$), filtered and concentrated to give crude product, which was taken to the next step without purification. MS (ES+) m/z 198.1 ((M-C$_4$H$_9$)+1).

Step b: Triethylamine (713 μL, 5.11 mmol) and benzyl chloroformate (810 mg, 4.72 mmol) were added to a solution of spiroamine (1000 mg, 3.93 mmol) in dichloromethane (25 mL) at 0° C. The resulting mixture was stirred at room temperature for 15 h, treated with saturated sodium bicarbonate and extracted twice with dichloromethane. The combined organic extracts were washed with brine, dried (MgSO$_4$), filtered and concentrated. The residue was purified by chromatography on silica gel (hexane/Et2O, 5:1 to 1:1) to afford desired product tert-butyl 1-(((benzyloxy) carbonyl)amino)-8-azaspiro[4.5]decane-8-carboxylate (800 mg, 53% over two steps) as a clear oil. MS (ES+) m/z 333.1 ((M-C$_4$H$_9$)+1).

Step c: Tert-butyl 1-(((benzyloxy)carbonyl)amino)-8-azaspiro[4.5]decane-8-carboxylate (200 mg, 0.51 mmol) was dissolve in DCM (2 mL) and HCl in dioxane (4M, 2 mL, 8.0 mmol) was added. The mixture was stirred 15 min at room temperature and evaporated off. The solid was dissolved in DCM and washed with a saturated solution of NaHCO$_3$. The aqueous phase was extracted three other times with DCM. The organic phase was combined, separated, dried (MgSO$_4$), filtered and concentrated to give pure benzyl 8-azaspiro[4.5]decan-1-ylcarbamate (136 mg, 92%), which was taken to the next step without purification. $^1$H NMR (500 MHz, CDCl$_3$) δ 7.40-7.21 (m, 5H), 5.01 (dd, J=37.9, 12.2 Hz, 2H), 4.58 (s, 1H), 2.87 (s, 2H), 2.63 (dt, J=21.3, 10.7 Hz, 2H), 2.05-1.84 (m, 1H), 1.80-1.61 (m, 3H), 1.56 (dd, J=11.0, 8.2 Hz, 2H), 1.45-1.28 (m, 3H), 1.28-1.10 (m, 3H). MS (ES+) m/z 288.4 (M+).

Example 2: Preparation of (2,3-dichlorophenyl)(3,5-dichloropyrazin-2-yl)methanone (2,3-dichlorophenyl)(3,5-dichloropyrazin-2-yl)methanone was prepared as schematically illustrated below.

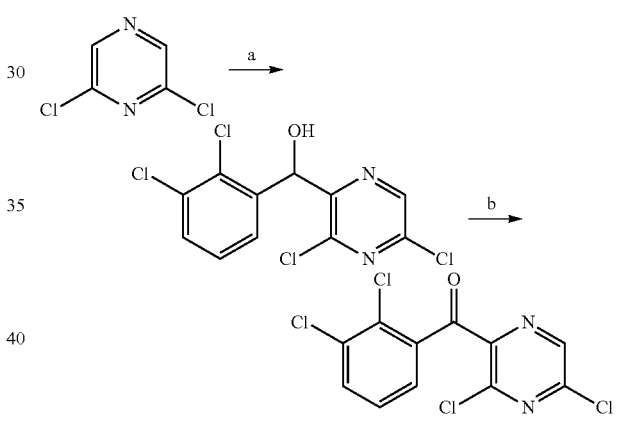

Step a: To a cold (−78° C.) solution of 2,2,6,6-tetramethylpiperidine (3.0 mL, 17.8 mmol) in THF (35 mL) was added n-BuLi (2.5 M, 8.8 mL, 17.0 mmol), then the mixture was warmed up to 0° C. and stirred for 30 min. The mixture was cooled down to −78° C. and 2,6-dichloropyrimidine (2.3 g, 15.4 mmol) in THF (3 mL) was added dropwise to the mixture. After stirring at −78° C. for 30 min., a solution of 2,3-dichlorobenzaldehyde (2.6 g, 18.5 mmol) was added to the mixture and stirred at −78° C. for 3 h and allowed to warmed-up. The reaction mixture was diluted with saturated aqueous ammonium chloride solution then extracted with dichloromethane. The organic layer was dried over magnesium sulfate, filtered and evaporated in vacuo. The resulting residue was purified by column chromatography on silica gel (AcOEt-hexane) to give alcohol (2,3-dichlorophenyl)(3, 5-dichloropyrazin-2-yl)methanol (750 mg, 24%) as an orange oil.

Step b: In a round bottom flask, (2,3-dichlorophenyl)(3, 5-dichloropyrazin-2-yl)methanol (500 mg, 1.55 mmol) was dissolved with dichloromethane (5 mL). Dess-Martin periodinane (792 mg, 1.86 mmol) was added and the mixture was stirred until completion. An aqueous solution of NaHCO$_3$ and Na$_2$S$_2$O$_3$ was then added. The mixture was stirred until the white solid went into the aqueous phase. The aqueous layer was extracted with DCM two more times. The combined organic extract was dried over magnesium sulfate, filtered and evaporated off, affording (2,3-dichlorophenyl)(3,5-dichloropyrazin-2-yl)methanone (485 mg, 93%) as an orange oil. MS (ES+) m/z 321.9 (MH+).

Example 3: Preparation of 6-chloro-3-(3-chlorophenyl)-1H-pyrazolo[3,4-b]pyrazine 6-chloro-3-(3-chlorophenyl)-1H-pyrazolo[3,4-b]pyrazine was prepared as schematically illustrated below.

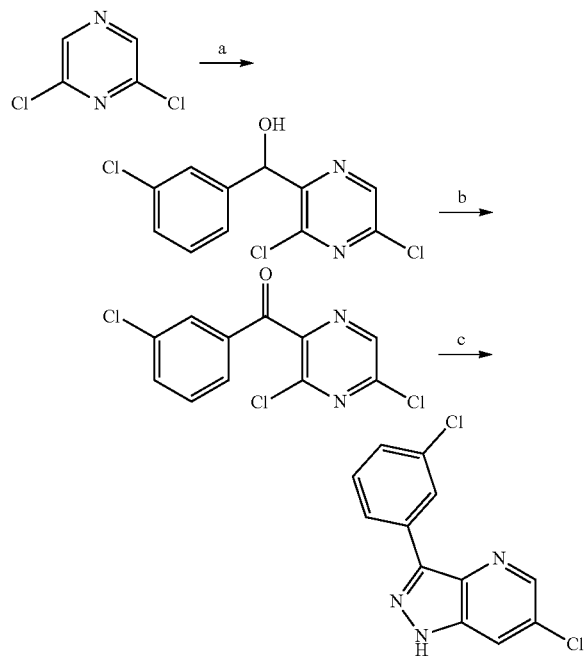

Step a: To a cold (−78° C.) solution of 2,2,6,6-tetramethylpiperidine(3.0 mL, 17.8 mmol) in THF (35 mL) was added n-BuLi (2.5 M, 8.8 mL, 17.0 mmol), then the mixture was warmed up to 0° C. and stirred for 30 min. The mixture was cooled down to −78° C. and 2,6-dichloropyrimidine (2.3 g, 15.4 mmol) in THF (3 mL) was added dropwise to the mixture. After stirring at −78° C. for 30 min., a solution of 3-chlorobenzaldehyde (2.1 g, 18.5 mmol) was added to the mixture and stirred at −78° C. for 3 h and allowed to warmed-up. The reaction mixture was diluted with saturated aqueous ammonium chloride solution then extracted with dichloromethane. The organic layer was dried over magnesium sulfate, filtered and evaporated off. The resulting residue was purified by column chromatography on silica gel (AcOEt-hexane) to give alcohol (3-chlorophenyl)(3,5-dichloropyrazin-2-yl)methanol (1.1 g, 38%) as an orange oil. MS (ES+) m/z 271.1 (M(—H2O)+).

Step b: In a round bottom flask, (3-chlorophenyl)(3,5-dichloropyrazin-2-yl)methanol (1.1 g, 3.8 mmol) was dissolved with dichloromethane (10 mL) and wrapped with aluminum foil. Manganese dioxide (2.1 g, 22.8 mmol) was added and the mixture was stirred at room temperature overnight. The mixture was filtrated over celite and evaporated off to deliver (3-chlorophenyl)(3,5-dichloropyrazin-2-yl)methanone (1.05 mg, 95%) as an orange oil.

Step c: To a solution of 3-chlorophenyl)(3,5-dichloropyrazin-2-yl)methanone in dichloromethane (1.0 g, 3.5 mmol) was added hydrazine hydrochloride (714 mg, 10.4 mmol) and di-isopropylethylamine (1.2 mL, 13.92 mmol) was slowly added at rt. After complete addition, the reaction mixture was sealed and stirred at 85° C. for 3 h. The mixture was concentrated and the residue was purified by chromatography on silica gel using AcOEt/hexane to afford 6-chloro-3-(3-chlorophenyl)-1H-pyrazolo[3,4-b]pyrazine (600 mg, 65%) as a red powder. MS (ES+) m/z 265.2 (M+).

Example 4: Preparation of benzyl ((4-hydroxypiperidin-4-yl)methyl)carbamate

Benzyl ((4-hydroxypiperidin-4-yl)methyl)carbamate was prepared as schematically illustrated below.

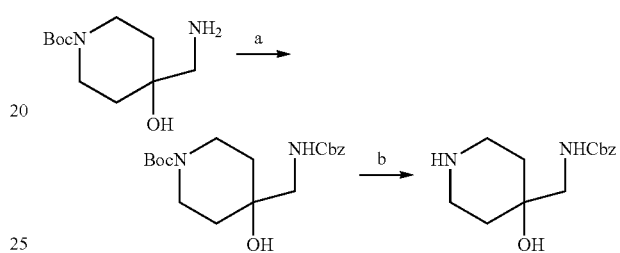

Step a: Tert-butyl 4-(aminomethyl)-4-hydroxypiperidine-1-carboxylate (300 mg, 1.30 mmol) was dissolved in EtOH (10 mL) and water (5 mL) and NaHCO3 (164 mg, 1.95 mmol) was added. Benzyl chloroformate (190 µL, 1.30 mmol) was added dropwise at room temperature and the mixture was stirred at room temperature for 120 min. The mixture was diluted with water (40 mL) and the mixture was extracted twice with Et2O (2×25 mL). Organic layers were combined and washed with brine, dried over magnesium sulfate, filtrated and concentrated. The residue was purified by chromatography on silica gel (hexane/Et2O, 10:1 to 1:1) to afford desired tert-butyl 4-((((benzyloxy)carbonyl)amino)methyl)-4-hydroxypiperidine-1-carboxylate (336 mg, 92%) as a clear oil. MS (ES+) m/z 264.4 (M-C5H9O2).

Step b: Tert-butyl 4-((((benzyloxy)carbonyl)amino)methyl)-4-hydroxypiperidine-1-carboxylate (336 mg, 0.92 mmol) was dissolve in DCM (1 mL) and HCl in dioxane (4M, 2 mL, 8.0 mmol) was added. The mixture was stirred 15 min at room temperature and evaporated off to give pure benzyl ((4-hydroxypiperidin-4-yl)methyl)carbamate hydrochloride (249 mg, 91%), which was taken to the next step without purification.

Example 5: Preparation of (4-chlorophenyl)(3,5-dichloropyrazin-2-yl)methanone (4-chlorophenyl)(3,5-dichloropyrazin-2-yl)methanone was prepared as schematically illustrated below.

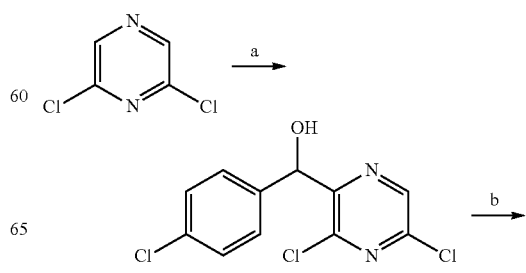

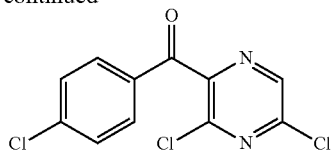

Step a: To a cold (−78° C.) solution of 2,2,6,6-tetramethylpiperidine(3.0 mL, 17.8 mmol) in THF (35 mL) was added n-BuLi (2.5 M, 8.8 mL, 17.0 mmol), then the mixture was warmed up to 0° C. and stirred for 30 min. The mixture was cooled down to −78° C. and 2,6-dichloropyrimidine (2.3 g, 15.4 mmol) in THF (3 mL) was added dropwise to the mixture. After stirring at −78° C. for 30 min., a solution of 4-chlorobenzaldehyde (2.1 g, 18.5 mmol) was added to the mixture and stirred at −78° C. for 3 h and allowed to warmed-up. The reaction mixture was diluted with saturated aqueous ammonium chloride solution then extracted with dichloromethane. The organic layer was dried over magnesium sulfate, filtered and evaporated in vacuo. The resulting residue was purified by column chromatography on silica gel (AcOEt-hexane) to give alcohol (4-chlorophenyl)(3,5-dichloropyrazin-2-yl)methanol (950 mg, 29%) as an orange oil. MS (ES+) m/z 271.1 (M(—H$_2$O)+).

Step b: In a round bottom flask, (4-chlorophenyl)(3,5-dichloropyrazin-2-yl)methanol (950 mg, 3.3 mmol) was dissolved with dichloromethane (10 mL) and wrapped with aluminum foil. Manganese dioxide (2.1 g, 22.8 mmol) was added and the mixture was stirred at room temperature overnight. The mixture was filtrated over celite and evaporated off to deliver (4-chlorophenyl)(3,5-dichloropyrazin-2-yl)methanone (904 mg, 96%) as an orange oil.

Example 6: Preparation of 6-chloro-3-(2-chlorophenyl)-1H-pyrazolo[3,4-b]pyrazine 6-chloro-3-(2-chlorophenyl)-1H-pyrazolo[3,4-b]pyrazine was prepared as schematically illustrated below.

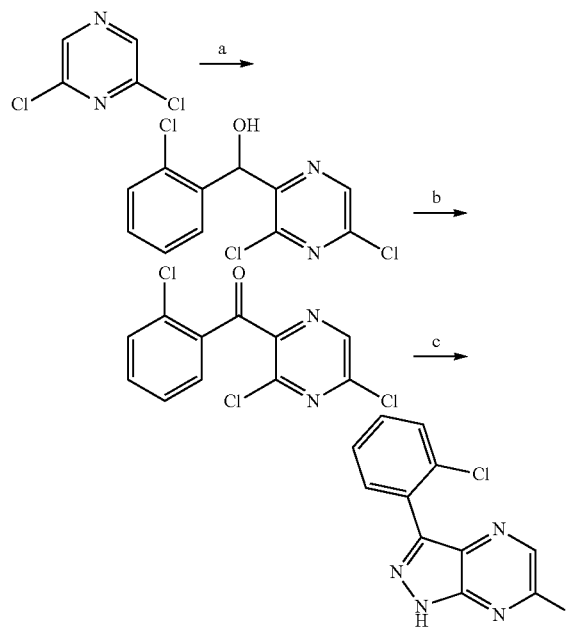

Step a: In a 250 mL flame dried RBF equipped with a temperature probe was added nBuLi (2.46 M, 2.2 mL, 5.39 mmol) and THF (49 mL) under nitrogen. The solution was cooled at −20° C. and 2,2,6,6-tetramethylpiperidine (0.95 mL, 5.64 mmol) was added dropwise. The solution was stirred at 0° C. for 30 min. before cooling at −105° C. with a nitrogen/Et$_2$O bath. A −78° C. solution of 2,6-dichloropyrazine (730 mg, 4.90 mmol) in THF (16 mL) was then cannulated over 10 min. to the −105° C. LiTMP solution. The mixture was allowed to stir an additional 30 min. at −100/−105° C. and a −78° C. solution of 2-chlorobenzaldehyde (0.83 mL, 7.35 mmol) in THF (7 mL) was added. The resulting solution was allowed to stir at −95° C. for an additional 1h15. An aqueous saturated solution of NH$_4$Cl (10 mL) was then added and the mixture was allowed to warm at room temperature. Water (200 mL) was added and the mixture was extracted with Et$_2$O (3×50 mL). Combined organic layers were washed with brine, dried over anhydrous Na$_2$SO$_4$, filtrated and the volatiles were removed under reduced pressure. The resulting residue was purified by silica gel chromatography (5 to 18% gradient of EtOAc/hexanes) to give (2-chlorophenyl)(3,5-dichloropyrazin-2-yl)methanol (1.10 g, 78% yield) as a yellow oil. $^1$H NMR (500 MHz, CDCl$_3$) δ ppm 8.56-8.56 (m, 1H), 7.41 (dd, J=7.7, 1.5 Hz, 1H), 7.27 (td, J=7.4, 1.8 Hz, 1H), 7.23 (td, J=7.5, 1.4 Hz, 1H), 7.12 (dd, J=7.6, 1.8 Hz, 1H), 6.47 (d, J=7.2 Hz, 1H), 4.07 (d, J=7.2 Hz, 1H). MS (ES+) m/z 271/273/275 (MH−H$_2$O)+.

Step b: To a solution of (2-chlorophenyl)(3,5-dichloropyrazin-2-yl)methanol (224 mg, 0.774 mmol) in DCM (4 mL) was added manganese (IV) oxide (650 mg, 7.74 mmol). The mixture was stirred at room temperature for 19 hours. The suspension was filtered on celite and it was washed with DCM and MeOH. The filtrate was evaporated and the resulting oil was dissolved in DCM, dried over anhydrous MgSO$_4$, filtrated and the volatiles were removed under reduced pressure to give (2-chlorophenyl)(3,5-dichloropyrazin-2-yl)methanone (223 mg, 100% yield) as a yellow oil which solidified to a yellowish solid. The obtained material was used crude in the next reaction. $^1$H NMR (500 MHz, CDCl$_3$) δ ppm 8.49 (s, 1H), 7.75 (ddd, J=7.6, 1.7, 0.3 Hz, 1H), 7.55-7.50 (m, 1H), 7.46-7.40 (m, 2H). MS (ES+) m/z 287/289 (M+1).

Step c: (2-chlorophenyl)(3,5-dichloropyrazin-2-yl)methanone (476 mg, 1.66 mmol), hydrazine monohydrochloride (227 mg, 3.31 mmol), DCM (7 mL) and THF (7 mL) were added in a 100 mL pressure vessel. The vessel was capped and the mixture was heated in a 80° C. oil bath for 4 hours. The mixture was cooled at room temperature and the remaining solids were filtered off. The filtrate was diluted with a saturated aqueous solution of NH$_4$Cl and the resulting mixture was extracted with EtOAc (3×50 mL). The combined organic layers were washed with brine, dried over anhydrous Na$_2$SO$_4$, filtrated and the volatiles were removed under reduced pressure. The resulting residue was purified by silica gel chromatography (15 to 25% gradient of EtOAc/hexanes) followed by a trituration in cold DCM to give 6-chloro-3-(2-chlorophenyl)-1H-pyrazolo[3,4-b]pyrazine (181 mg, 41% yield) as a white solid. $^1$H NMR (500 MHz, CDCl$_3$) δ 10.70-10.49 (m, 1H), 8.63 (s, 1H), 7.82 (br. s, 1H), 7.61-7.55 (m, 1H), 7.46-7.41 (m, 2H). MS (ES+) m/z 265/267 (M+1).

Example 7: Preparation of benzyl ((4-methylpiperidin-4-yl)methyl)carbamate

Benzyl ((4-methylpiperidin-4-yl)methyl)carbamate was prepared as schematically illustrated below.

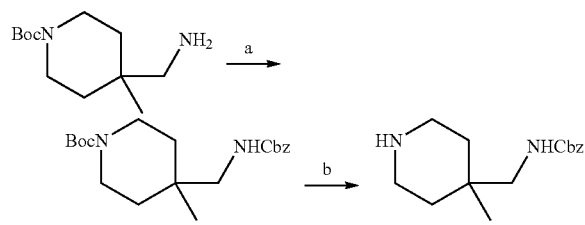

Step a: To a 0° C. solution of tert-butyl 4-(aminomethyl)-4-methylpiperidine-1-carboxylate (7.0 g, 30.66 mmol), $NaHCO_3$ (3.86 g, 45.99 mmol) in ethanol (131 mL) and water (92 mL) was added benzyl chloroformate (4.4 mL, 30.66 mmol). The reaction mixture was stirred at room temperature for 2 hours and most of ethanol was removed under reduced pressure. The resulting mixture was extracted with $Et_2O$ (3×100 mL). Combined organic layers were washed with brine, dried over anhydrous $MgSO_4$, filtrated and the volatiles were removed under reduced pressure. The resulting residue was purified on a silica gel pad (20 to 30% gradient of EtOAc/hexanes) to give tert-butyl 4-((benzyloxycarbonylamino)methyl)-4-methylpiperidine-1-carboxylate (9.78 g, 88% yield) as a yellowish oil. $^1$H NMR (500 MHz, $CDCl_3$) δ ppm 7.41-7.29 (m, 5H), 5.17-5.05 (m, 2H), 4.79 (br. s, 1H), 3.70-3.58 (m, 2H), 3.22-2.99 (m, 4H), 1.45 (s, 9H), 1.42-1.35 (m, 2H), 1.31-1.23 (m, 2H), 0.94 (s, 3H). MS (ES+) m/z 363 (M+1).

Step b: TFA (100 mL, 1310 mmol) was added to a solution tert-butyl 4-((benzyloxycarbonylamino)methyl)-4-methylpiperidine-1-carboxylate (9.50 g, 26.2 mmol) in DCM (131 mL) at room temperature. The mixture was stirred for 1.5 hours and the volatiles were removed under reduced pressure. The resulting oil was dissolved in DCM (100 mL) and a saturated aqueous solution of $NaHCO_3$ (200 mL) was slowly added. The two layers were separated and the aqueous layer was extracted with more DCM (6×50 mL). The combined organic layers were washed with brine (50 mL), dried over anhydrous $MgSO_4$, filtrated and the volatiles were removed under reduced pressure to give benzyl (4-methylpiperidin-4-yl)methylcarbamate (6.0 g, 87% yield) as a beige foam. $^1$H NMR (500 MHz, DMSO-d6) δ ppm 7.31-7.22 (m, 5H), 5.09-4.94 (m, 2H), 4.91-4.73 (m, 1H), 3.08-2.91 (m, 2H), 2.91-2.66 (m, 5H), 1.42-1.29 (m, 2H), 1.28-1.12 (m, 2H), 0.87 (s, 3H). MS (ES+) m/z 263 (M+1).

Example 8: Preparation of benzyl (4-methylpiperidin-4-yl)carbamate

Benzyl (4-methylpiperidin-4-yl)carbamate was prepared as schematically illustrated below.

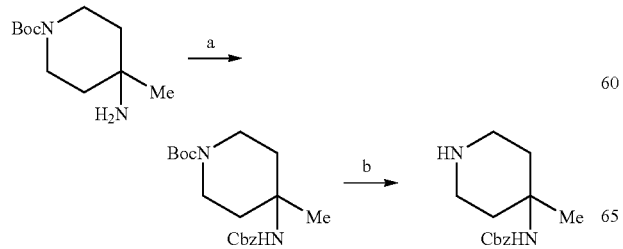

Step a: To a 100 mL round-bottom flask was added 4-amino-4-methyl-N-Boc-piperidine (500 mg, 2.33 mmol, 1.0 equiv). It was dissolved in a mixture of $EtOH:H_2O$ (10:1) (11.7 mL, 0.2 M), and $NaHCO_3$ was added (391 mg, 4.66 mmol, 2.0 equiv). The reaction was initiated by addition of CbzCl (419 mg, 0.36 mL, 2.45 mmol, 1.1 equiv) dropwise. The cloudy solution was stirred at rt for 3 hours. After that period, LCMS showed full conversion to the desired Cbz-protected amine. The reaction was diluted with EtOAc (40 mL) and water (20 mL). The biphasic mixture was transferred to a 125 mL extraction funnel and the layers were separated. The aqueous layer was extracted with EtOAc (3×30 mL) and the layers were combined, washed with brine (3×30 mL), dried over $Na_2SO_4$, filtered, and evaporated to dryness. It resulted in a clear oil which was analyzed by NMR showing the desired product and some other by-products arising from the amine. The crude residue was purified by flash chromatography using a gradient of 100% Hexanes to 70% EtOAc in hexanes over a 40 g SNAP ultra column, using 18 CV. The product came out at around 30% EtOAc in hexanes as a faintly UV-active ($R_f$=0.8 in 20% EtOAc in hexanes) compound. Evaporation to dryness procured the product as a translucent liquid (560 mg, 70% yield). MS (ES+) m/z 349, 293, 249 (M+1, –tBu, –Boc), $R_T$=1.83 min.

Step b: To a 100 mL round-bottom flask was added tert-butyl 4-(((benzyloxy)carbonyl)amino)-4-methylpiperidine-1-carboxylate (560 mg, 1.6 mmol, 1.0 equiv). It was dissolved in anhydrous DCM (8.0 mL, 0.2 M). TFA (6.1 mL, 80.0 mmol, 50 equiv) was then added dropwise to the reaction and the yellow solution was stirred for 1.5 hour at room temperature. After that period, LCMS showed full conversion to the desired deprotected amine. The reaction solvents were evaporated to dryness and the resulting residue was redissolved in EtOAc (40 mL) and quenched by addition of $NaHCO_3$ sat. aq. (20 mL) until pH was found to be 10-11. The biphasic mixture was transferred to a 125 mL extraction funnel and the layers were separated. The aqueous layer was extracted with EtOAc (3×30 mL) and the layers were combined, washed with brine (3×30 mL), dried over $Na_2SO_4$, filtered, and evaporated to dryness. It resulted in a clear oil which was which was used in the next step without further purification (390 mg, 97% yield). MS (ES+) m/z 249 (M+1), $R_T$=1.07 min.

Example 9: Preparation of 3-(2,3-dichlorophenyl)-6-(piperidin-1-yl)-1H-pyrazolo[3,4-b]pyrazine 3-(2,3-dichlorophenyl)-6-(piperidin-1-yl)-1H-pyrazolo[3,4-b]pyrazine was prepared as schematically illustrated below.

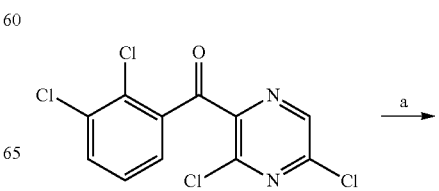

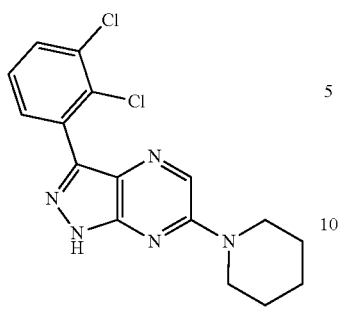

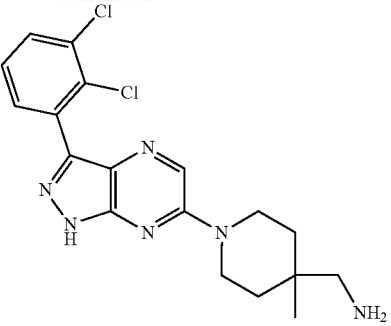

Step a: To a solution (2,3-dichlorophenyl)(3,5-dichloropyrazin-2-yl)methanone (100 mg, 0.31 mmol) in DMAc (1. mL) was slowly added piperidine (31 μL, 0.31 mmol) at 0-5° C., and stirred at the same temperature for 0.5-3 h. Then, hydrazine monohydrate (40 μL, 1.24 mmol) was slowly added at 0-5° C. (exothermic). After complete addition, the reaction mixture was stirred at 0-5° C. for 1 h, and heat at 90° C. for 1-5 h. The reaction mixture was cooled to 0° C., and adjusted water (10 mL) and EtOAc (10 mL) were charged, respectively. After phase separation, the aqueous layer was extracted with EtOAc (10 mL). The combined organic layers were washed with water (10 mL), brine (10 mL), dried over magnesium sulfate and concentrated. The residue was purified by chromatography on silica gel (hexane/EtOAc, 1:0 to 1:1) to afford desired product 3-(2, 3-dichlorophenyl)-6-(piperidin-1-yl)-1H-pyrazolo[3,4-b] pyrazine (48 mg, 45%) as a yellow foam. $^1$H NMR (400 MHz, CDCl$_3$) δ 8.25 (s, 1H), 7.64 (dd, J=7.7, 1.6 Hz, 1H), 7.54 (dt, J=6.0, 3.0 Hz, 1H), 7.32 (dd, J=9.4, 6.3 Hz, 1H), 3.74 (d, J=5.8 Hz, 4H), 1.93-1.49 (m, 6H). MS (ES+) m/z 348.0 (MH+).

Example 10: Preparation of (1-(3-(2,3-dichlorophenyl)-1H-pyrazolo[3,4-b]pyrazin-6-yl)-4-methylpiperidin-4-yl)methanamine (1-(3-(2,3-dichlorophenyl)-1H-pyrazolo[3,4-b]pyrazin-6-yl)-4-methylpiperidin-4-yl)methanamine was prepared as schematically illustrated below.

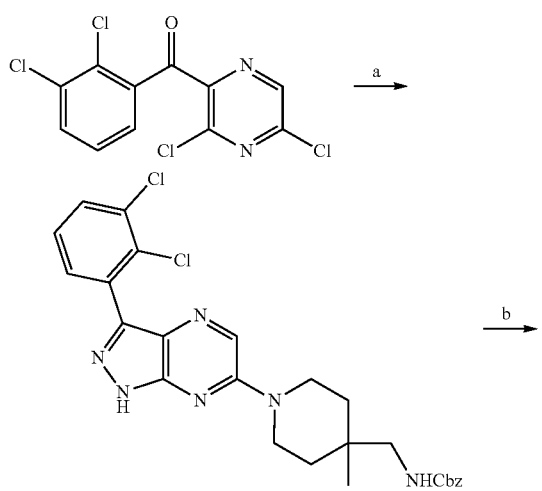

Step a: To a solution (2,3-dichlorophenyl)(3,5-dichloropyrazin-2-yl)methanone (100 mg, 0.31 mmol) in DMAc (1.0 mL) was slowly added benzyl ((4-methylpiperidin-4-yl) methyl)carbamate (81 mg, 0.31 mmol) at 0-5° C., and stirred at the same temperature for 0.5-3 h. Then, hydrazine monohydrate (40 μL, 1.24 mmol) was slowly added at 0-5° C. (exothermic). After complete addition, the reaction mixture was stirred at 0-5° C. for 1 h, and heat at 90° C. for 1-5 h. The reaction mixture was cooled to 0° C., and adjusted water (10 mL) and EtOAc (10 mL) were charged, respectively. After phase separation, the aqueous layer was extracted with EtOAc (10 mL). The combined organic layers were washed with water (10 mL), brine (10 mL), dried over magnesium sulfate and concentrated. The residue was purified by chromatography on silica gel (hexane/EtOAc=1:1, 1:3) to afford desired product benzyl ((1-(3-(2,3-dichlorophenyl)-1H-pyrazolo [3,4-b]pyrazin-6-yl)-4-methylpiperidin-4-yl) methyl)carbamate (66 mg, 42%) as a yellow foam. MS (ES+) m/z 524.9 (MH+).

Step b: HBr in acid acetic (33% wt %, 1.0 mL) was added dropwise benzyl ((1-(3-(2,3-dichlorophenyl)-1H-pyrazolo [3,4-b]pyrazin-6-yl)-4-methylpiperidin-4-yl)methyl)carbamate (66 mg, 0.21 mmol). The mixture was stirred for 1 hr at room temperature. Water and diethyl ether was then added. The aqueous phase was extracted three times with diethyl ether and basified with saturated solution of NaHCO$_3$. The aqueous phase was extract three times with dichloromethane. The combined organic extract was dried over magnesium sulfate, filtered and evaporated off. The crude product was purified by flash chromatography using MeOH/DCM as eluant to afford (1-(3-(2,3-dichlorophenyl)-1H-pyrazolo[3,4-b]pyrazin-6-yl)-4-methylpiperidin-4-yl) methanamine (32 mg, 65%) as a white solid. $^1$H NMR (500 MHz, CDCl$_3$) δ 8.20 (s, 1H), 7.59 (dd, J=7.7, 1.5 Hz, 1H), 7.48 (dd, J=8.0, 1.6 Hz, 1H), 7.25 (t, J=7.9 Hz, 1H), 3.97 (d, J=13.3 Hz, 2H), 3.39 (dd, J=47.9, 37.8 Hz, 2H), 2.52 (s, 2H), 1.74-1.30 (m, 4H), 1.19 (s, 3H). MS (ES+) m/z 390.2 (M+).

Example 11: Preparation of (1-(3-(2-chlorophenyl)-1H-pyrazolo[4,3-b]pyrazin-6-yl)-4-methylpiperidin-4-yl)methanamine (1-(3-(2-chlorophenyl)-1H-pyrazolo[4,3-b]pyrazin-6-yl)-4-methylpiperidin-4-yl)methanamine was prepared as schematically illustrated below.

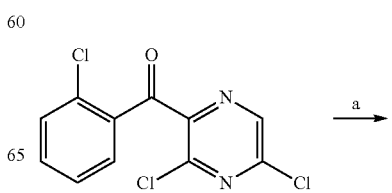

-continued

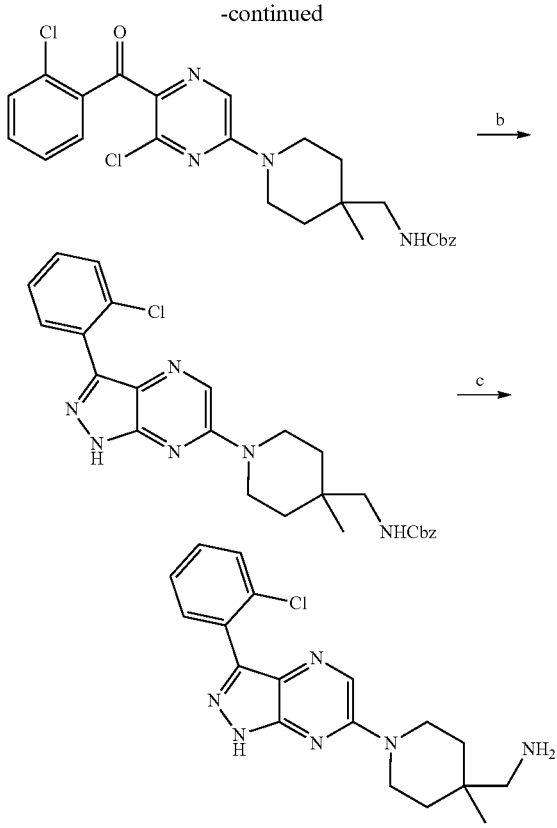

Step a: To a mixture of (2-chlorophenyl)(3,5-dichloropyrazin-2-yl)methanone (310 mg, 1.08 mmol) and benzyl ((4-methylpiperidin-4-yl)methyl)carbamate (283 mg, 1.08 mmol) in DMAc (5.4 mL) was added cesium fluoride (508 mg, 3.34 mmol). The resulting mixture was stirred in a 75° C. oil bath for 21 hours. The reaction mixture was then diluted with water (10 mL) and an aqueous saturated solution of NaHCO$_3$ (75 mL). The resulting mixture was extracted with Et$_2$O (3×25 mL) and the combined organic layers were washed with brine, dried over anhydrous Na$_2$SO$_4$, filtrated and the volatiles were removed under reduced pressure. The resulting residue was purified by silica gel chromatography (5 to 30% gradient of EtOAc/hexanes) to give benzyl (1-(6-chloro-3-(2-chlorobenzoyl)pyrazin-2-yl)-4-methylpiperidin-4-yl)methylcarbamate (undesired regioisomer, 86 mg, 16% yield, yellow solid) and benzyl (1-(6-chloro-5-(2-chlorobenzoyl)pyrazin-2-yl)-4-methylpiperidin-4-yl)methylcarbamate (desired regioisomer, 328 mg, 59% yield, beige solid): $^1$H NMR (500 MHz, CDCl$_3$) δ ppm 7.91 (s, 1H), 7.48-7.44 (m, 1H), 7.40-7.29 (m, 8H), 5.17-5.06 (m, 2H), 4.89 (t, J=6.5 Hz, 1H), 4.00-3.82 (m, 2H), 3.61-3.37 (m, 2H), 3.20-3.07 (m, 2H), 1.60-1.51 (m, 2H), 1.50-1.37 (m, 2H), 1.02 (s, 3H). MS (ES+) m/z 513/515 (M+1).

Step b: To a solution of 6 benzyl (1-(6-chloro-5-(2-chlorobenzoyl)pyrazin-2-yl)-4-methylpiperidin-4-yl)methylcarbamate (45 mg, 0.088 mmol) in DMAc (0.9 mL) was added a solution of hydrazine hydrate (50-60%, 0.40 mL, 7.01 mmol). The reaction mixture was stirred in a 75° C. oil bath for 20 hours and it was diluted with water (50 mL). The resulting mixture was extracted with Et$_2$O (3×25 mL) and the combined organic layers were washed with brine, dried over anhydrous Na$_2$SO$_4$, filtrated and the volatiles were removed under reduced pressure. The resulting residue was purified by silica gel chromatography (20 to 60% gradient of EtOAc/hexanes) to give benzyl (1-(3-(2-chlorophenyl)-1H-pyrazolo[4,3-b]pyrazin-6-yl)-4-methylpiperidin-4-yl)methylcarbamate (40 mg, 93% yield) as a beige foam. $^1$H NMR (500 MHz, CDCl$_3$) δ ppm 10.48 (s, 1H), 8.26 (s, 1H), 7.81 (dd, J=7.3, 2.0 Hz, 1H), 7.56-7.52 (m, 1H), 7.43-7.28 (m, 7H), 5.11 (s, 2H), 4.90 (t, J=6.3 Hz, 1H), 4.02-3.94 (m, 2H), 3.61-3.50 (m, 2H), 3.18 (d, J=6.7 Hz, 2H), 1.66-1.53 (m, 2H), 1.53-1.45 (m, 2H), 1.04 (s, 3H). MS (ES+) m/z 491/493 (M+1).

Step c: HBr in AcOH (33%, 1.1 mL) was added to benzyl (1-(3-(2-chlorophenyl)-1H-pyrazolo[4,3-b]pyrazin-6-yl)-4-methylpiperidin-4-yl)methylcarbamate (40 mg, 0.082 mmol) and the solution was stirred at room temperature for 1h30. The reaction mixture was added dropwise to an Et$_2$O solution (20 mL). The resulting solid was filtered and rinsed with Et$_2$O. The residue was diluted in water and purified by reverse phase chromatography (C18, 0 to 80% gradient of MeCN/(10 mM NH$_4$HCO$_3$ in water, pH 10) to give (1-(3-(2-chlorophenyl)-1H-pyrazolo[4,3-b]pyrazin-6-yl)-4-methylpiperidin-4-yl)methanamine (25 mg, 86% yield) as a white solid. $^1$H NMR (500 MHz, DMSO-d6) δ ppm 8.34 (s, 1H), 7.69-7.63 (m, 1H), 7.60-7.55 (m, 1H), 7.48-7.41 (m, 2H), 3.98-3.89 (m, 2H), 3.47-3.39 (m, 2H), 2.42 (s, 2H), 1.49-1.40 (m, 2H), 1.40-1.29 (m, 2H), 0.94 (s, 3H). 3 NH missing. MS (ES+) m/z 357/359 (M+1).

Example 12: Preparation of 7-(3-(2-chlorophenyl)-1H-pyrazolo[3,4-b]pyrazin-6-yl)-7-azaspiro [3.5] nonan-1-amine 7-(3-(2-chlorophenyl)-1H-pyrazolo[3,4-b]pyrazin-6-yl)-7-azaspiro[3.5]nonan-1-amine was prepared as schematically illustrated below.

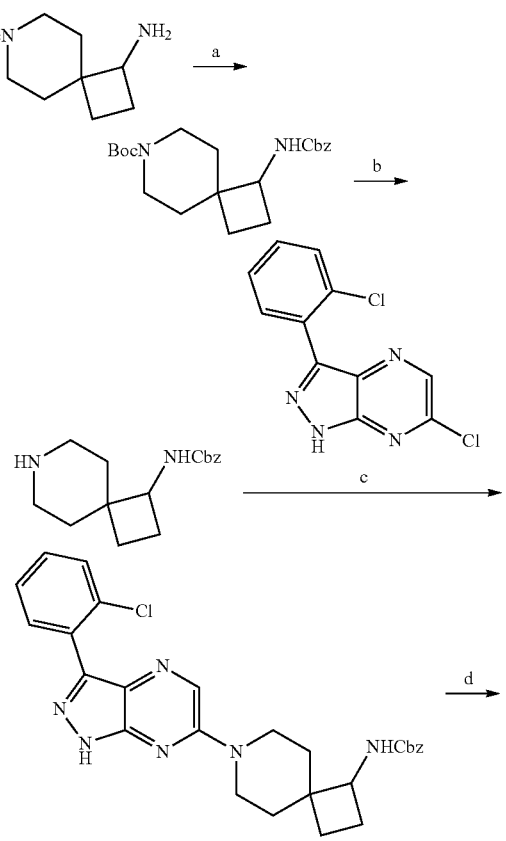

-continued

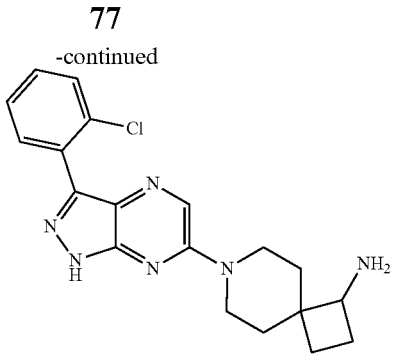

Step a: To a 0° C. solution of tert-butyl 1-amino-7-azaspiro[3.5]nonane-7-carboxylate (252 mg, 1.05 mmol), NaHCO$_3$ (132 mg, 1.58 mmol) in ethanol (3 mL) and water (2 mL) was added benzyl chloroformate (0.15 mL, 1.05 mmol). The reaction mixture was stirred at room temperature for 2 hours and most of ethanol was removed under reduced pressure. Water (20 mL) was added to the resulting mixture and it was extracted with DCM (2×20 mL). Combined organic layers were washed with brine, dried over anhydrous MgSO$_4$, filtrated and the volatiles were removed under reduced pressure. The resulting residue was purified by silica gel chromatography (30% of EtOAc/hexanes) to give tert-butyl 1-(((benzyloxy)carbonyl)amino)-7-azaspiro[3.5]nonane-7-carboxylate (263 mg, 67% yield) as a colorless oil. $^1$H NMR (500 MHz, CDCl$_3$) δ 7.40-7.31 (m, 5H), 5.13 (d, J=12 Hz, 1H), 5.06 (d, J=12.2 Hz, 1H), 4.84 (d, J=8.5 Hz, 1H), 4.00-3.95 (m, 1H), 3.85 (d, J=12.3 Hz, 1H), 3.79 (d, J=13 Hz, 1H), 3.02-2.94 (m, 1H), 2.90-2.81 (m, 1H), 2.37-2.28 (m, 1H), 1.80-1.67 (m, 3H), 1.56-1.49 (m, 4H), 1.46 (s, 9H). MS (ES+) m/z 397 (M+Na).

Step b: TFA (2.7 mL, 35.1 mmol) was added to a solution tert-butyl 1-(((benzyloxy)carbonyl)amino)-7-azaspiro[3.5]nonane-7-carboxylate (263 mg, 0.702 mmol) in DCM (3.5 mL) at room temperature. The mixture was stirred for 1.5 hours and the volatiles were removed under reduced pressure. The resulting oil was dissolved in DCM (10 mL) and a saturated aqueous solution of NaHCO$_3$ (20 mL) was slowly added followed by water (8 mL). The two layers were separated and the aqueous layer was extracted with more DCM (6×10 mL). The combined organic layers were washed with brine, dried over anhydrous MgSO$_4$, filtrated and the volatiles were removed under reduced pressure to give benzyl 7-azaspiro[3.5]nonan-1-ylcarbamate (160 mg, 83% yield) as a pale yellow foam. $^1$H NMR (500 MHz, DMSO-d6) δ ppm δ 7.41-7.32 (m, 5H), 5.14 (d, J=12.0 Hz, 1H), 5.07 (d, J=12.1 Hz, 1H), 4.89 (d, J=8.6 Hz, 1H), 4.00-3.95 (m, 1H), 3.12-3.05 (m, 2H), 2.94-2.92 (m, 1H), 2.83-2.79 (m, 1H), 2.35-2.30 (m, 1H), 1.89-1.85 (m, 1H), 1.79-1.66 (m, 5H), 1.56-1.50 (m, 1H). MS (ES+) m/z 275/277 (M+1).

Step c: To a mixture of 6-chloro-3-(2-chlorophenyl)-1H-pyrazolo[3,4-b]pyrazine (22 mg, 0.083 mmol) and benzyl 7-azaspiro[3.5]nonan-1-ylcarbamate (46 mg, 0.17 mmol) in NMP (0.4 mL) was added K$_3$PO$_4$ (27 mg, 0.13 mmol). The resulting mixture was stirred in a 90° C. oil bath for 14 hours. The reaction mixture was cooled at room temperature, poured in water (10 mL) and extracted with DCM (3×15 mL). The organic layers were combined, washed with a saturated aqueous solution of NaHCO$_3$ (20 mL), brine (20 mL), dried over anhydrous Na$_2$SO$_4$, filtered and the volatiles were removed under reduced pressure. The crude product was purified by reverse phase chromatography (10 to 75% gradient of MeCN//(10 mM NH$_4$HCO$_2$ in water, pH 3.8) to give benzyl (7-(3-(2-chlorophenyl)-1H-pyrazolo[3,4-b]pyrazin-6-yl)-7-azaspiro[3.5]nonan-1-yl)carbamate (39 mg, 93%) as a yellowish powder. MS (ES+) m/z 503 [M+H]$^+$.

Step d: HBr in AcOH (33%, 1.1 mL) was added to benzyl (7-(3-(2-chlorophenyl)-1H-pyrazolo[3,4-b]pyrazin-6-yl)-7-azaspiro[3.5]nonan-1-yl)carbamate (39 mg, 0.076 mmol) and the solution was stirred at room temperature for 1 hour. The reaction mixture was added dropwise to an Et$_2$O solution (20 mL). The resulting solid was filtered and rinsed with Et$_2$O. The residue was diluted in water and purified by reverse phase chromatography (C18, 0 to 80% gradient of MeCN/(10 mM NH$_4$HCO$_3$ in water, pH 10) to give 7-(3-(2-chlorophenyl)-1H-pyrazolo[4,3-b]pyrazin-6-yl)-7-azaspiro[3.5]nonan-1-amine (18 mg, 64% yield) as a white solid. $^1$H NMR (500 MHz, DMSO-d$_6$) δ 13.26 (br. s, 1H), 8.43 (s, 1H), 7.78-7.72 (m, 1H), 7.63-7.56 (m, 1H), 7.50-7.42 (m, 2H), 4.28 (dt, J=7.6, 4.0 Hz, 1H), 4.15 (dt, J=12.7, 3.7 Hz, 1H), 3.18-3.10 (m, 1H), 2.97 (t, J=8.0 Hz, 1H), 2.13-2.03 (m, 1H), 1.88 (s, 2H), 1.72-1.57 (m, 6H), 1.51-1.35 (m, 2H). MS (ES+) m/z 369/371 [M+H]$^+$.

Example 13: Isolation of (S)-7-(3-(2-chlorophenyl)-1H-pyrazolo[3,4-b]pyrazin-6-yl)-7-azaspiro [3.5]nonan-1-amine

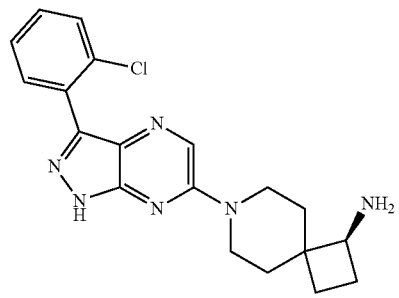 [SMILES: N[C@H]1CCC12CCN(c1cnc3c(-c4ccccc4Cl)n[nH]c3n1)CC2]

Chiral separation of a racemic sample (12 mg) (ChiralPak IA, 5 m 20×250 mm, 15:15:70 (MeOH:DCM:Hexane+0.1% Et$_2$NH), 12 mL/min., RT=8.287 min) provided 3.9 mg of this single enantiomers as white solid. $^1$H NMR (500 MHz, DMSO-d$_6$) δ 13.26 (br. s, 1H), 8.43 (s, 1H), 7.78-7.72 (m, 1H), 7.63-7.56 (m, 1H), 7.50-7.42 (m, 2H), 4.28 (dt, J=7.6, 4.0 Hz, 1H), 4.15 (dt, J=12.7, 3.7 Hz, 1H), 3.18-3.10 (m, 1H), 2.97 (t, J=8.0 Hz, 1H), 2.13-2.03 (m, 1H), 1.88 (s, 2H), 1.72-1.57 (m, 6H), 1.51-1.35 (m, 2H). MS (ES+) m/z 369/371 [M+H]$^+$.

Example 14: Isolation of (R)-7-(3-(2-chlorophenyl)-1H-pyrazolo[3,4-b]pyrazin-6-yl)-7-azaspiro [3.5]nonan-1-amine

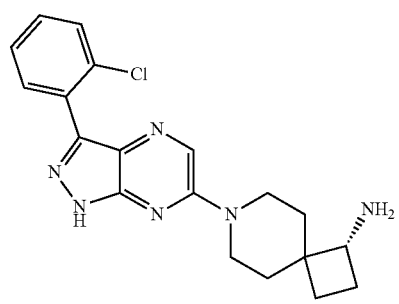 [SMILES: N[C@@H]1CCC12CCN(c1cnc3c(-c4ccccc4Cl)n[nH]c3n1)CC2]

Chiral separation of a racemic sample (12 mg) (ChiralPak IA, 5 m 20×250 mm, 15:15:70 (MeOH:DCM:Hexane+0.1% Et₂NH), 12 mL/min., RT=10.031 min) provided 3.8 mg of this single enantiomers as white solid. $^1$H NMR (500 MHz, DMSO-d$_6$) δ 13.26 (br. s, 1H), 8.43 (s, 1H), 7.78-7.72 (m, 1H), 7.63-7.56 (m, 1H), 7.50-7.42 (m, 2H), 4.28 (dt, J=7.6, 4.0 Hz, 1H), 4.15 (dt, J=12.7, 3.7 Hz, 1H), 3.18-3.10 (m, 1H), 2.97 (t, J=8.0 Hz, 1H), 2.13-2.03 (m, 1H), 1.88 (s, 2H), 1.72-1.57 (m, 6H), 1.51-1.35 (m, 2H). MS (ES+) m/z 369/371 [M+H]⁺.

Example 15: Preparation of 6-(3-(2-chlorophenyl)-1H-pyrazolo[4,3-b]pyrazin-6-yl)-6-azaspiro[2.5]octan-1-amine 6-(3-(2-chlorophenyl)-1H-pyrazolo[4,3-b]pyrazin-6-yl)-6-azaspiro[2.5]octan-1-amine was prepared as schematically illustrated below.

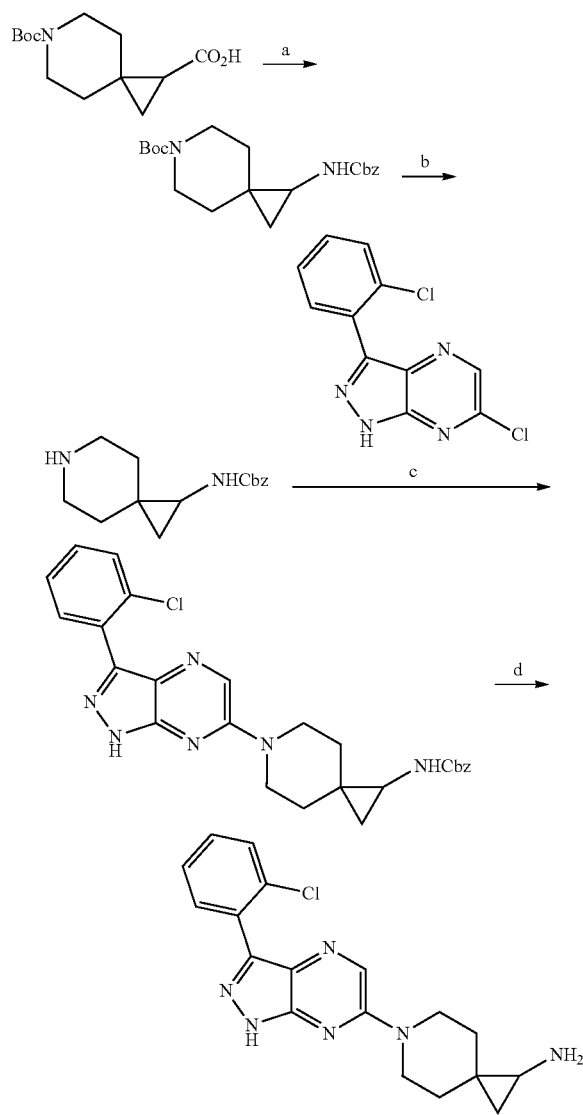

Step a: To a 0° C. suspension of 6-(tert-butoxycarbonyl)-6-azaspiro[2.5]octane-1-carboxylic acid (1.00 g, 3.92 mmol) in toluene were added Et₃N (0.60 mL, 4.31 mmol) and diphenyl phosphoryl azide (0.93 mL, 4.31 mmol). The mixture was ballowed to warm at room temperature and it was heated in a 110° C. oil bath for 2 hours. Benzyl alcohol (0.45 mL, 4.31 mmol) was then added and the solution was heated at 110° C. for an additional 2 hours. The resulting mixture was cooled at room temperature and a saturated solution of NaHCO₃ was added. The mixture was extracted with Et₂O (3×50 mL). Combined organic layers were washed with brine, dried over anhydrous Na₂SO₄, filtrated and the volatiles were removed under reduced pressure. The crude product was purified on a silica gel using CombiFlash (20 to 30% gradient of EtOAc/hexanes) to give tert-butyl 1-(benzyloxycarbonylamino)-6-azaspiro[2.5]octane-6-carboxylate with a LCMS purity of 87%. The obtained material was repurified by reverse phase chromatography (C18, 0 to 80% gradient of MeCN/(10 mM NH₄HCO₂ in water, pH 3.8) to give the desired product (945 mg, 67% yield, >99% purity by LCMS) as a yellowish foam. MS (ES+) m/z 361 (M+1).

Step b: TFA (10 mL, 131 mmol) was added to a solution tert-butyl 1-(benzyloxycarbonylamino)-6-azaspiro[2.5]octane-6-carboxylate (945 mg, 2.62 mmol) in DCM (13 mL) at room temperature. The mixture was stirred for 1h45 and the volatiles were removed under reduced pressure. The resulting oil was dissolved in DCM (25 mL). A saturated aqueous solution of NaHCO₃ (25 mL) was slowly added followed by water (25 mL). The two layers were separated and the aqueous layer was extracted with more DCM (4×50 mL). The combined organic layers were washed with brine (25 mL), dried over anhydrous MgSO₄, filtrated and the volatiles were removed under reduced pressure to give benzyl 6-azaspiro[2.5]octan-1-ylcarbamate (327 mg, 48% yield) as a beige foam. $^1$H NMR (500 MHz, DMSO-d6) δ 7.44-7.25 (m, 5H), 5.14-4.92 (m, 2H), 2.88-2.59 (m, 4H), 2.35 (dt, J=8.0, 4.0 Hz, 1H), 1.47-1.14 (m, 4H), 0.63-0.52 (m, 1H), 0.43-0.28 (m, 1H). 2 NH missing. MS (ES+) m/z 261 (M+1).

Step c: To a mixture of 6-chloro-3-(2-chlorophenyl)-1H-pyrazolo[3,4-b]pyrazine (32 mg, 0.121 mmol) and benzyl 6-azaspiro[2.5]octan-1-ylcarbamate (63 mg, 0.241 mmol) in NMP (0.6 mL) was added K₃PO₄ (38 mg, 0.181 mmol). The resulting mixture was stirred in a 90° C. oil bath for 13 hours. The reaction mixture was diluted with water and the formed solid was collected by filtration. The crude product was purified by silica gel chromatography (5 to 30% gradient of EtOAc/hexanes) to give benzyl 6-(3-(2-chlorophenyl)-1H-pyrazolo[4,3-b]pyrazin-6-yl)-6-azaspiro[2.5]octan-1-ylcarbamate (35 mg, 59% yield) as a yellowish solid. MS (ES+) m/z 489/491 (M+1).

Step d: HBr in AcOH (33%, 1.0 mL) was added to benzyl 6-(3-(2-chlorophenyl)-1H-pyrazolo[4,3-b]pyrazin-6-yl)-6-azaspiro[2.5]octan-1-ylcarbamate (35 mg, 0.0716 mmol) and the solution was stirred at room temperature for 1 hour. The reaction mixture was added dropwise to an Et₂O solution (20 mL). The resulting solid was filtered and rinsed with Et₂O. The residue was diluted in water and purified by reverse phase chromatography (C18, 0 to 80% gradient of MeCN/(10 mM NH₄HCO₃ in water, pH 10) to give 6-(3-(2-chlorophenyl)-1H-pyrazolo[4,3-b]pyrazin-6-yl)-6-azaspiro[2.5]octan-1-amine (20 mg, 79% yield) as a white solid. $^1$H NMR (500 MHz, DMSO-d6) δ 13.30 (br. s, 1H), 8.42 (s, 1H), 7.77-7.71 (m, 1H), 7.61-7.55 (m, 1H), 7.49-7.41 (m, 2H), 3.93-3.80 (m, 2H), 3.72-3.56 (m, 2H), 2.19-2.08 (m, 1H), 1.85 (s, 2H), 1.77-1.66 (m, 1H), 1.63-1.53 (m, 1H), 1.47-1.35 (m, 1H), 1.26-1.17 (m, 1H), 0.45 (dd, J=7.2, 4.5 Hz, 1H), 0.11 (t, J=4.1 Hz, 1H). MS (ES+) m/z 355/357 (M+1).

Example 16: Isolation of (S)-6-(3-(2-chlorophenyl)-1H-pyrazolo[4,3-b]pyrazin-6-yl)-6-azaspiro[2.5]octan-1-amine

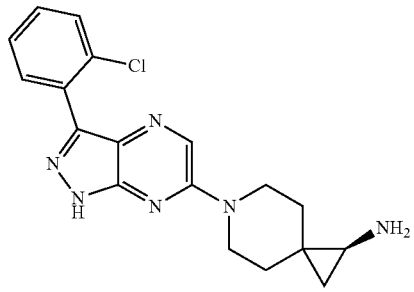 [SMILES: N[C@H]1CC12CCN(c1cnc3c(-c4ccccc4Cl)n[nH]c3n1)CC2]

Chiral separation of a racemic sample (13 mg) (ChiralPak IA, 5 m 20×250 mm, 15:15:70 (MeOH:DCM:Hexane+0.1% Et$_2$NH, RT=7.95 min), 12 mL/min.) provided 4.0 mg of this single enantiomers as white solid. $^1$H NMR (500 MHz, DMSO-d6) δ 13.30 (br. s, 1H), 8.42 (s, 1H), 7.77-7.71 (m, 1H), 7.61-7.55 (m, 1H), 7.49-7.41 (m, 2H), 3.93-3.80 (m, 2H), 3.72-3.56 (m, 2H), 2.19-2.08 (m, 1H), 1.85 (s, 2H), 1.77-1.66 (m, 1H), 1.63-1.53 (m, 1H), 1.47-1.35 (m, 1H), 1.26-1.17 (m, 1H), 0.45 (dd, J=7.2, 4.5 Hz, 1H), 0.11 (t, J=4.1 Hz, 1H). MS (ES+) m/z 355/357 (M+1).

Example 17: Isolation of (R)-6-(3-(2-chlorophenyl)-1H-pyrazolo[4,3-b]pyrazin-6-yl)-6-azaspiro[2.5]octan-1-amine

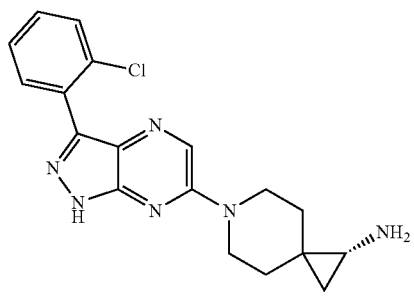 [SMILES: N[C@@H]1CC12CCN(c1cnc3c(-c4ccccc4Cl)n[nH]c3n1)CC2]

Chiral separation of a racemic sample (13 mg) (ChiralPak IA, 5 m 20×250 mm, 15:15:70 (MeOH:DCM:Hexane+0.1% Et$_2$NH, RT=7.95 min), 12 mL/min.) provided 4.0 mg of this single enantiomers as white solid. $^1$H NMR (500 MHz, DMSO-d6) δ 13.30 (br. s, 1H), 8.42 (s, 1H), 7.77-7.71 (m, 1H), 7.61-7.55 (m, 1H), 7.49-7.41 (m, 2H), 3.93-3.80 (m, 2H), 3.72-3.56 (m, 2H), 2.19-2.08 (m, 1H), 1.85 (s, 2H), 1.77-1.66 (m, 1H), 1.63-1.53 (m, 1H), 1.47-1.35 (m, 1H), 1.26-1.17 (m, 1H), 0.45 (dd, J=7.2, 4.5 Hz, 1H), 0.11 (t, J=4.1 Hz, 1H). MS (ES+) m/z 355/357 (M+1).

Example 18: Preparation of (S) 8-(3-(2-chlorophenyl)-1H-pyrazolo[3,4-b]pyrazin-6-yl)-8-azaspiro[4.5]decan-1-amine (S) 8-(3-(2-chlorophenyl)-1H-pyrazolo[3,4-b]pyrazin-6-yl)-8-azaspiro[4.5]decan-1-amine was prepared as schematically illustrated below.

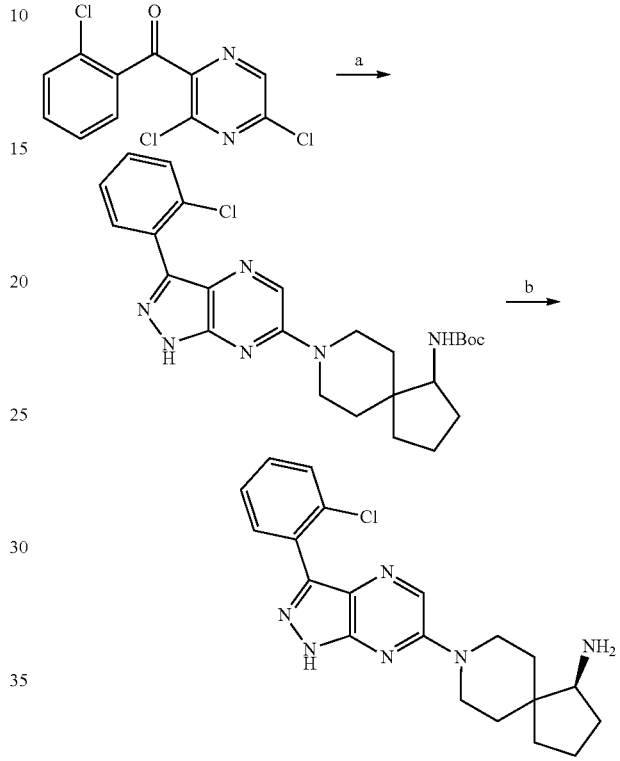

Step a: To a solution (2,3-dichlorophenyl)(2-chloropyrazin-2-yl)methanone (70 mg, 0.24 mmol) in DMAc (1.0 mL) was slowly added benzyl 8-azaspiro[4.5]decan-1-ylcarbamate (70 mg, 0.25 mmol) at 0-5° C., and stirred at the same temperature for 0.5-3 h. Cesium fluoride (40 mg, 26 mmol) was added and the reaction was heated at 80° C. The reaction was cooled down to room temperature and hydrazine monohydrate (31 µL, 0.97 mmol) was slowly added at 0-5° C. After complete addition, the reaction mixture was stirred at 0-5° C. for 1 h, and heat at 90° C. for 1-5 h. The reaction mixture was cooled to 0° C., and adjusted water (10 mL) and EtOAc (10 mL) were charged, respectively. After phase separation, the aqueous layer was extracted with EtOAc (10 mL). The combined organic layers were washed with water (10 mL), brine (10 mL), dried over magnesium sulfate and concentrated. The residue was purified by chromatography on silica gel (hexane/EtOAc, 1:0 to 1:1) to afford desired product benzyl (8-(3-(2-chlorophenyl)-1H-pyrazolo[3,4-b]pyrazin-6-yl)-8-azaspiro[4.5]decan-1-yl)carbamate as a white solid. MS (ES+) m/z 517.3 (M+1).

Step b: HBr in acid acetic (33% wt %, 1.5 mL) was added dropwise benzyl (8-(3-(2-chlorophenyl)-1H-pyrazolo[3,4-b]pyrazin-6-yl)-8-azaspiro[4.5]decan-1-yl)carbamate (50 mg, 0.21 mmol). The mixture was stirred for 1 hr at room temperature. Diethyl ether was then added and a solid crashed out. The liquid was removed and the solid was triturated with diethyl ether. The residue was diluted in water and purified by C18 chromatography (0% to 100% gradient of MeCN/water) (32 mg, 87%) and purified again by semi-preparative SFC-UV (55% CO$_2$ and 45% MeOH+10 mMM NH$_4$HCO$_2$, column ChiralPak IC 250 mm×10 mm, RT=9.64 min) to give (S)-8-(3-(2-chlorophenyl)-1H-pyrazolo[3,4-b]pyrazin-6-yl)-8-azaspiro[4.5]decan-1-amine as a white solid. $^1$H NMR (400 MHz, DMSO) δ 8.46 (s, 1H), 7.72 (dt, J=6.6, 3.1 Hz, 1H), 7.63-7.53 (m, 2H), 7.53-7.34 (m, 2H), 4.34 (dd, J=21.8, 13.9 Hz, 2H), 3.25-3.03 (m, 2H), 2.10-1.94 (m, 1H), 1.94-1.23 (m, 9H). MS (ES+) m/z 382.9 (M+1).

Example 19: Isolation of (R) 8-(3-(2-chlorophenyl)-1H-pyrazolo[3,4-b]pyrazin-6-yl)-8-azaspiro [4.5]decan-1-amine

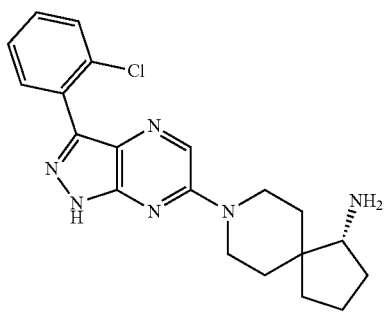 [SMILES: N[C@@H]1CCCC12CCN(c1cnc3c(-c4ccccc4Cl)n[nH]c3n1)CC2]

A racemic sample (32 mg) was purified by semi-preparative SFC-UV (55% CO$_2$ and 45% MeOH+10 mMM NH$_4$HCO$_2$, column ChiralPak IC 250 mm×10 mm, RT=13.25 min) to give (R)-8-(3-(2-chlorophenyl)-1H-pyrazolo[3,4-b]pyrazin-6-yl)-8-azaspiro[4.5]decan-1-amine as a white solid. $^1$H NMR (400 MHz, DMSO) δ 8.46 (s, 1H), 7.72 (dt, J=6.6, 3.1 Hz, 1H), 7.63-7.53 (m, 2H), 7.53-7.34 (m, 2H), 4.34 (dd, J=21.8, 13.9 Hz, 2H), 3.25-3.03 (m, 2H), 2.10-1.94 (m, 1H), 1.94-1.23 (m, 9H). MS (ES+) m/z 382.9 (M+1).

Example 20: Preparation of (1-(3-(3-chlorophenyl)-1H-pyrazolo[3,4-b]pyrazin-6-yl)-4-methylpiperidin-4-yl)methanamine (1-(3-(3-chlorophenyl)-1H-pyrazolo[3,4-b]pyrazin-6-yl)-4-methylpiperidin-4-yl)methanamine was prepared as schematically illustrated below.

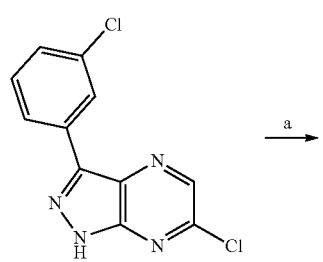

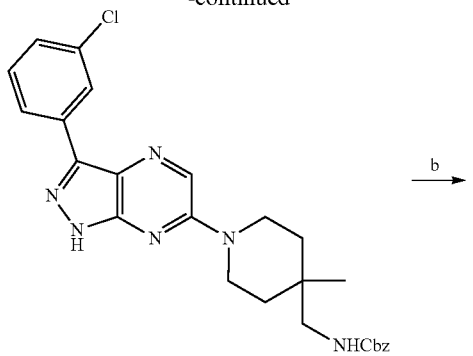

Step a: A mixture 6-chloro-3-(3-chlorophenyl)-1H-pyrazolo[3,4-b]pyrazine (50 mg, 0.19 mmol), benzyl ((4-methylpiperidin-4-yl)methyl)carbamate (49 mg, 0.19 mmol), K$_3$PO$_4$ (60 mg, 0.28 mmol) and DMAc (1 mL) was stirred at 80° C. for 18 h. The reaction mixture was diluted with EtOAc and water and transferred into a separation funnel. The layers were separated and the aqueous phase was extracted with EtOAc. The combined organic phases were washed with brine (3×), dried over MgSO4, filtered, and the volatiles were removed under reduced pressure. The resulting residue was purified by silica gel chromatography (10 to 70% gradient of EtOAc/hexanes) to benzyl ((1-(3-(3-chlorophenyl)-1H-pyrazolo[3,4-b]pyrazin-6-yl)-4-methylpiperidin-4-yl)methyl)carbamate (80 mg, 86%) as a yellow foam. MS (ES+) m/z 491.1 (M+1).

Step b: HBr in acid acetic (33% wt %, 1.5 mL) was added dropwise benzyl ((1-(3-(3-chlorophenyl)-1H-pyrazolo [3,4-b]pyrazin-6-yl)-4-methylpiperidin-4-yl)methyl)carbamate (80 mg, 0.37 mmol). The mixture was stirred for 1 hr at room temperature. Water and diethyl ether was then added. The aqueous phase was extracted three times with diethyl ether and basified with saturated solution of NaHCO$_3$. The aqueous phase was extract three times with dichloromethane containing 10% of methanol. The combined organic extract was dried over magnesium sulfate, filtered and evaporated off affording (1-(3-(3-chlorophenyl)-1H-pyrazolo[3,4-b]pyrazin-6-yl)-4-methylpiperidin-4-yl)methanamine (52 mg, 76%) as a beige solid. $^1$H NMR (400 MHz, DMSO-d6) δ 8.50 (s, 1H), 8.41-8.33 (m, 1H), 8.29-8.17 (m, 1H), 7.51 (t, J=7.9 Hz, 1H), 7.42 (ddd, J=8.0, 2.2, 1.1 Hz, 1H), 3.96 (dd, J=9.0, 5.1 Hz, 2H), 3.57-3.40 (m, 2H), 1.60-1.27 (m, 6H), 1.17 (S, 3H). MS (ES+) m/z 357.3 (M+1).

Example 21: Preparation of 4-amino-1-(3-(3-chlorophenyl)-1H-pyrazolo[3,4-b]pyrazin-6-yl)piperidine-4-carbonitrile 4-amino-1-(3-(3-chlorophenyl)-1H-pyrazolo[3,4-b]pyrazin-6-yl)piperidine-4-carbonitrile was prepared as schematically illustrated below.

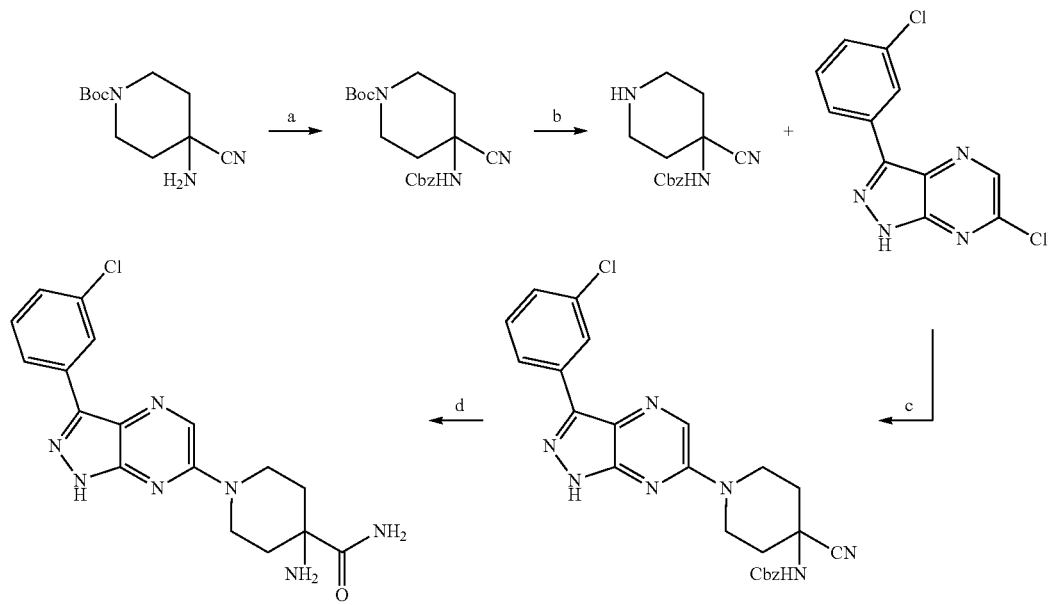

Step a: To a 100 mL round-bottom flask was added 4-amino-4-cyano-N-Boc-piperidine (500 mg, 2.2 mmol, 1.0 equiv). It was dissolved in a mixture of EtOH:H₂O (10:1) (11.0 mL, 0.2 M), and NaHCO₃ was added (373 mg, 4.44 mmol, 2.0 equiv). The reaction was initiated by addition of CbzCl (417 mg, 0.35 mL, 2.44 mmol, 1.1 equiv) dropwise. The cloudy solution was stirred at rt for 3 hours. After that period, LCMS showed full conversion to the desired Cbz-protected amine. The reaction was diluted with EtOAc (40 mL) and water (20 mL). The biphasic mixture was transferred to a 125 mL extraction funnel and the layers were separated. The aqueous layer was extracted with EtOAc (3×30 mL) and the layers were combined, washed with brine (3×30 mL), dried over Na₂SO₄, filtered, and evaporated to dryness. It resulted in a clear oil which was analyzed by NMR showing the desired product and some other by-products arising from the amine. The crude residue was purified by flash chromatography using a gradient of 100% Hexanes to 70% EtOAc in hexanes over a 40 g SNAP ultra column, using 18 CV. The product came out at around 30% EtOAc in hexanes as a faintly UV-active ($R_f$=0.7 in 30% EtOAc in hexanes) compound. Evaporation to dryness procured the product as a white foamy solid (610 mg, 77% yield). MS (ES+) m/z 360, 304, 260 (M+1, −tBu, −Boc), $R_T$=1.72 min.

Step b: To a 100 mL round-bottom flask was added tert-butyl 4-(((benzyloxy)carbonyl)amino)-4-cyanopiperidine-1-carboxylate (630 mg, 1.75 mmol, 1.0 equiv). It was dissolved in anhydrous DCM (8.75 mL, 0.2 M). TFA (6.7 mL, 87.7 mmol, 50 equiv) was then added dropwise to the reaction and the yellow solution was stirred for 1.5 hour at room temperature. After that period, LCMS showed full conversion to the desired deprotected amine. The reaction solvents were evaporated to dryness and the resulting residue was redissolved in EtOAc (40 mL) and quenched by addition of NaHCO₃ sat. aq. (20 mL) until pH was found to be 10-11. The biphasic mixture was transferred to a 125 mL extraction funnel and the layers were separated. The aqueous layer was extracted with EtOAc (3×30 mL) and the layers were combined, washed with brine (3×30 mL), dried over Na₂SO₄, filtered, and evaporated to dryness. It resulted in a clear oil which was which was used in the next step without further purification (410 mg, 91% yield). MS (ES+) m/z 260 (M+1), $R_T$=1.10 min.

Step c: To a flame-dried, nitrogen-flushed 0.5-2.0 mL microwave vial equipped with a conic stirbar and a white 14-septum was added 6-chloro-3-(3-chlorophenyl)-1H-pyrazolo[3,4-b]pyrazine (50 mg, 0.189 mmol, 1.0 equiv), benzyl (4-cyanopiperidin-4-yl)carbamate (54 mg, 0.208 mmol, 1.1 equiv) and K₃PO₄ (40 mg, 0.284 mmol, 1.5 equiv). The reactants were dissolved in DMAc (0.630 mL, 0.3 M), the vial was capped with a Teflon cap and the reaction was stirred at 90° C. overnight in a oil bath. The reaction was cooled back to RT and opened to air. The crude was diluted with EtOAc (20 mL) while being transferred to a 60 mL extraction funnel. A mix of NaHCO₃:brine (1:1) was added (10 mL) and the layers were extracted and separated. Aqueous layer was further extracted with EtOAc (2×10 mL) and layers were combined. The organic layer was then washed further with brine (3×10 mL), dried over Na₂SO₄, filtered, and evaporated to dryness. The crude was further purified by flash chromatography using a 4 g Silicycle column using a gradient of 100% Hexanes to 100% EtOAc. The starting chloride came off at 20% EtOAc in hexanes and the product came off at around 50-60% EtOAc in hexanes as yellow fractions followed by a broad product at 80% EtOAc in hexanes. The fractions containing the desired product were evaporated to dryness. It resulted in a yellow film which consisted in pure product by NMR (12 mg, 13% yield). MS (ES+) m/z 488.2 (M+1), $R_T$=2.04 min.

Step d: To a 100 mL round bottom flask equipped with a magnetic stirbar was added benzyl (1-(3-(3-chlorophenyl)-1H-pyrazolo[3,4-b]pyrazin-6-yl)-4-cyanopiperidin-4-yl) carbamate (10 mg, 0.020 mmol, 1.00 equiv). It was directly reacted with excess amounts of HBr 33% in AcOH (1.0 mL) and the reaction was stirred at RT until it was judged to be finished by LCMS. After 1 hour, water (10 mL) was added to the reaction followed by EtOAc (10 mL) while transferring the biphasic mixture to a 60 mL extraction funnel. The aqueous layer was further extracted with EtOAc (2×20 mL) and the organic layer was disposed of. Then, the aqueous layer was basified by addition of $Na_2CO_3$ sat. aq. until pH was found to be 11-12 and it was further diluted with DCM (15 mL). The aqueous layer was back-extracted and layers were separated. The aqueous layer was extracted with more DCM (3×20 mL). Organic layer was then dried over $Na_2SO_4$, filtered, and evaporated to dryness. The product was lyophilized overnight in a mixture of MeCN and $H_2O$. It procures a yellow powder which consisted in the desired product (5.9 mg, 68% yield, 96.0% purity). $^1$H NMR (400 MHz, $CDCl_3$) δ 8.40 (dd, J=7.9, 6.2 Hz, 1H), 8.32 (s, 1H), 8.30-8.26 (m, 1H), 7.46-7.33 (m, 2H), 5.31 (s, 2H), 4.26 (dt, J=13.7, 4.6 Hz, 2H), 3.52 (ddd, J=13.7, 10.7, 3.3 Hz, 2H), 2.37-2.28 (m, 2H), 1.40-1.20 (br m, 2H), 1.30 (s, 2H). MS (ES+) m/z 372 (M+1), $R_T$=1.24 min.

Example 22: Preparation of 1-(3-(3-chlorophenyl)-1H-pyrazolo[3,4-b]pyrazin-6-yl)-4-methylpiperidin-4-amine 1-(3-(3-chlorophenyl)-1H-pyrazolo[3,4-b]pyrazin-6-yl)-4-methylpiperidin-4-amine was prepared as schematically illustrated below.

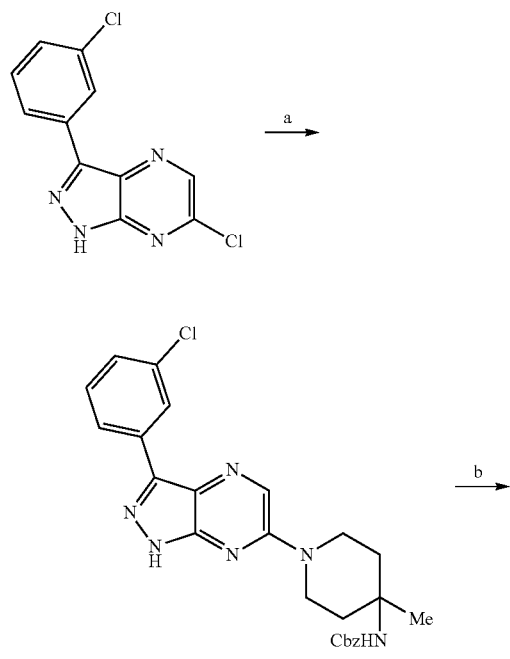

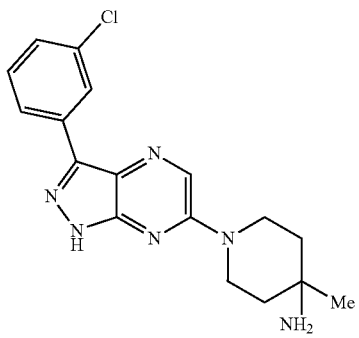

Step a: To a flame-dried, nitrogen-flushed 0.5-2.0 mL microwave vial equipped with a conic stirbar and a white 14-septum was added 6-chloro-3-(3-chlorophenyl)-1H-pyrazolo[3,4-b]pyrazine (50 mg, 0.189 mmol, 1.0 equiv), benzyl (4-methylpiperidin-4-yl)carbamate (52 mg, 0.208 mmol, 1.1 equiv) and $K_3PO_4$ (40 mg, 0.284 mmol, 1.5 equiv). The reactants were dissolved in DMAc (0.630 mL, 0.3 M), the vial was capped with a Teflon cap and the reaction was stirred at 90° C. overnight in a oil bath. The reaction was cooled back to RT and opened to air. The crude was diluted with EtOAc (20 mL) while being transferred to a 60 mL extraction funnel. A mix of $NaHCO_3$:brine (1:1) was added (10 mL) and the layers were extracted and separated. Aqueous layer was further extracted with EtOAc (2×10 mL) and layers were combined. The organic layer was then washed further with brine (3×10 mL), dried over $Na_2SO_4$, filtered, and evaporated to dryness. The crude was further purified by flash chromatography using a 4 g Silicycle column using a gradient of 100% Hexanes to 100% EtOAc. The starting chloride came off at 20% EtOAc in hexanes and the product came off at around 50-60% EtOAc in hexanes as translucent fractions. The fractions containing the desired product were evaporated to dryness. It resulted in a yellow film which consisted in pure product by NMR (61 mg, 68% yield). MS (ES+) m/z 477 (M+1), $R_T$=1.92 min.

Step b: To a 100 mL round bottom flask equipped with a magnetic stirbar was added benzyl (1-(3-(3-chlorophenyl)-1H-pyrazolo[3,4-b]pyrazin-6-yl)-4-methylpiperidin-4-yl) carbamate (56 mg, 0.117 mmol, 1.00 equiv). It was directly reacted with excess amounts of HBr 33% in AcOH (1.0 mL) and the reaction was stirred at RT until it was judged to be finished by LCMS. After 1 hour, water (10 mL) was added to the reaction followed by EtOAc (10 mL) while transferring the biphasic mixture to a 60 mL extraction funnel. The aqueous layer was further extracted with EtOAc (2×20 mL) and the organic layer was disposed of. Then, the aqueous layer was basified by addition of $Na_2CO_3$ sat. aq. until pH was found to be 11-12 and it was further diluted with DCM (15 mL). The aqueous layer was back-extracted and layers were separated. The aqueous layer was extracted with more DCM (3×20 mL). Organic layer was then dried over $Na_2SO_4$, filtered, and evaporated to dryness. The product was lyophilized overnight in a mixture of MeCN and $H_2O$. It procures a yellow powder which consisted in the desired product (29 mg, 73% yield, 94.6% purity). $^1$H NMR (400 MHz, $CDCl_3$) δ 8.39 (dd, J=10.6, 8.8 Hz, 1H), 8.30 (s, 1H), 8.28 (dd, J=7.6, 1.4 Hz, 1H), 7.45-7.31 (m, 2H), 3.92-3.81 (m, 2H), 3.80-3.68 (m, 2H), 1.72-1.63 (m, 2H), 1.61-1.53 (m, 2H), 1.26-1.19 (m, 2H), 1.23 (s, 3H). MS (ES+) m/z 343 (M+1), $R_T$=1.29 min.

Example 23: Preparation of (1-(3-(4-chlorophenyl)-1H-pyrazolo[3,4-b]pyrazin-6-yl)-4-methylpiperidin-4-yl)methanamine (1-(3-(4-chlorophenyl)-1H-pyrazolo[3,4-b]pyrazin-6-yl)-4-methylpiperidin-4-yl)methanamine was prepared as schematically illustrated below.

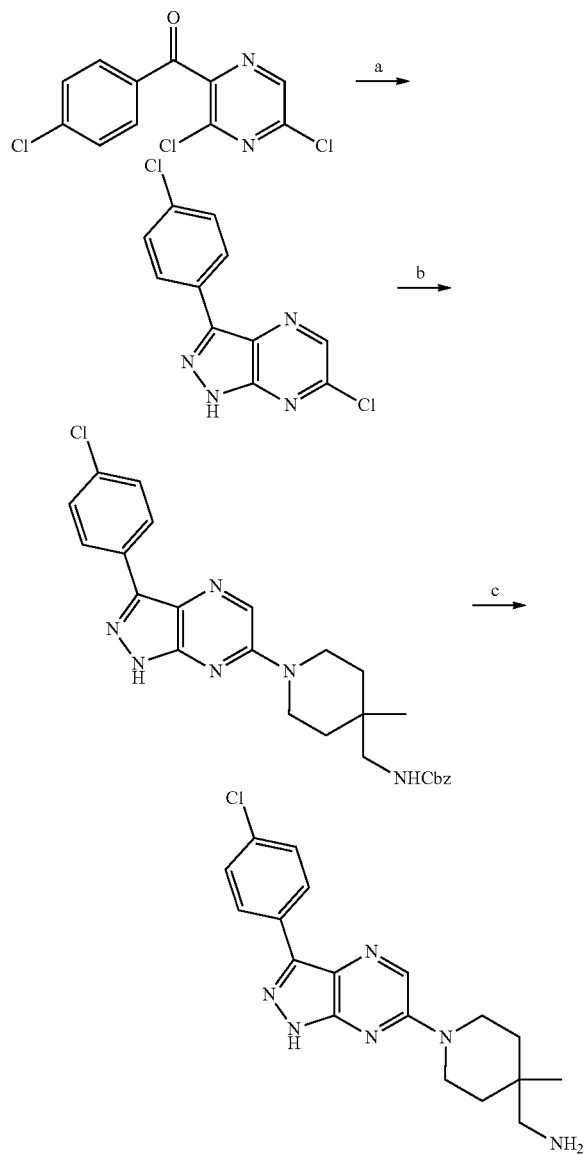

Step a: To a solution of 4-chlorophenyl)(3,5-dichloropyrazin-2-yl)methanone in dichloromethane (950 mg, 3.4 mmol) was added hydrazine (714 mg, 10.4 mmol) and di-isopropylethylamine (1.2 mL, 13.92 mmol) was slowly added at rt. After complete addition, the reaction mixture was sealed and stirred at 85° C. for 3 h. The mixture was concentrated and the residue was purified by chromatography on silica gel using AcOEt/hexane to afford 6-chloro-3-(4-chlorophenyl)-1H-pyrazolo[3,4-b]pyrazine (625 mg, 69%) as a red powder. MS (ES+) m/z 265.2 (M+)

Step b: A mixture 6-chloro-3-(4-chlorophenyl)-1H-pyrazolo[3,4-b]pyrazine (50 mg, 0.19 mmol), benzyl ((4-methylpiperidin-4-yl)methyl)carbamate (49 mg, 0.19 mmol), $K_3PO_4$ (60 mg, 0.28 mmol) and DMAc (1 mL) was stirred at 80° C. for 18 h. The reaction mixture was diluted with EtOAc and water and transferred into a separation funnel. The layers were separated and the aqueous phase was extracted with EtOAc. The combined organic phases were washed with brine (3×), dried over MgSO4, filtered, and the volatiles were removed under reduced pressure. The resulting residue was purified by silica gel chromatography (10 to 70% gradient of EtOAc/hexanes) to benzyl ((1-(3-(4-chlorophenyl)-1H-pyrazolo[3,4-b]pyrazin-6-yl)-4-methylpiperidin-4-yl)methyl)carbamate (50 mg, 54%) as a yellow foam. MS (ES+) m/z 491.2 (M+1).

Step c: HBr in acid acetic (33% wt %, 1.5 mL) was added dropwise benzyl ((1-(3-(4-chlorophenyl)-1H-pyrazolo [3,4-b]pyrazin-6-yl)-4-methylpiperidin-4-yl)methyl)carbamate- (80 mg, 0.37 mmol). The mixture was stirred for 1 hr at room temperature. Diethyl ether was then added and a solid crashed out. The liquid was removed and the solid was triturated with diethyl ether. The residue was diluted in water and purified by C18 chromatography (0% to 100% gradient of MeCN/(0.1% NH4HCO3 in water) to give (1-(3-(4-chlorophenyl)-1H-pyrazolo[3,4-b]pyrazin-6-yl)-4-methylpiperidin-4-yl)methanamine (12 mg, 22%) as a white solid. $^1$H NMR (400 MHz, DMSO-d6) δ 8.59-8.39 (m, 1H), 8.30 (t, J=6.7 Hz, 2H), 7.52 (t, J=7.1 Hz, 2H), 4.09-3.78 (m, 2H), 3.39 (dd, J=47.9, 37.8 Hz, 2H), 2.61 (S, 2H), 1.63-1.23 (m, 4H), 1.03 (s, 3H). MS (ES+) m/z 357.2 (M+1).

Example 24: Preparation of 1-(3-(2-Chlorophenyl)-1H-pyrazolo[3,4-b]pyrazin-6-yl)-4-methylpiperidin-4-amine 1-(3-(2-Chlorophenyl)-1H-pyrazolo[3,4-b]pyrazin-6-yl)-4-methylpiperidin-4-amine was prepared as described below.

Step a: To a flame-dried, nitrogen-flushed 0.5-2.0 mL microwave vial equipped with a conic stirbar and a white 14-septum was added 6-chloro-3-(2-chlorophenyl)-1H-pyrazolo[3,4-b]pyrazine (41 mg, 0.155 mmol, 1.0 equiv), benzyl (4-methylpiperidin-4-yl)carbamate (58 mg, 0.232 mmol, 1.5 equiv) and $K_3PO_4$ (49 mg, 0.232 mmol, 1.5 equiv). The reactants were dissolved in DMAc (0.520 mL, 0.3 M), the vial was capped with a Teflon cap and the reaction was stirred at 100° C. overnight in a oil bath. The reaction was cooled back to RT and opened to air. The crude was diluted with EtOAc (20 mL) while being transferred to a 60 mL extraction funnel. A mix of NaHCO$_3$:brine (1:1) was added (10 mL) and the layers were extracted and separated. Aqueous layer was further extracted with EtOAc (2×10 mL) and layers were combined. The organic layer was then washed further with brine (3×10 mL), dried over Na$_2$SO$_4$, filtered, and evaporated to dryness. The crude was further purified by flash chromatography using a 4 g Silicycle column using a gradient of 100% Hexanes to 80% EtOAc in hexanes. The product came off at around 50-60% EtOAc in hexanes as translucent fractions. The fractions containing the desired product were evaporated to dryness. It resulted in a yellow film which consisted in pure product by NMR (29 mg, 39% yield). MS (ES+) m/z 477 (M+1), R$_T$=1.75 min.

Step b: To a 100 mL round bottom flask equipped with a magnetic stirbar was added benzyl (1-(3-(2-chlorophenyl)-1H-pyrazolo[3,4-b]pyrazin-6-yl)-4-methylpiperidin-4-yl) carbamate (29 mg, 0.061 mmol, 1.00 equiv). It was directly reacted with excess amounts of HBr 33% in AcOH (0.7 mL) and the reaction was stirred at RT until it was judged to be finished by LCMS. After 30 minutes, water (10 mL) was added to the reaction followed by EtOAc (10 mL) while transferring the biphasic mixture to a 60 mL extraction funnel. The aqueous layer was further extracted with EtOAc (2×20 mL) and the organic layer was disposed of. Then, the aqueous layer was basified by addition of $Na_2CO_3$ sat. aq. until pH was found to be 11-12 and it was further diluted with DCM (15 mL). The aqueous layer was back-extracted and layers were separated. The aqueous layer was extracted with more DCM (3×20 mL). Organic layer was then dried over $Na_2SO_4$, filtered, and evaporated to dryness. The product was lyophilized overnight in a mixture of MeCN and $H_2O$. It procures a white powder which consisted in the desired product (16 mg, 76% yield, >99.5% purity). $^1H$ NMR (400 MHz, DMSO-$d_6$) δ 13.1 (br s, 1H), 8.38 (s, 1H), 7.71 (dd, J=5.9, 3.7 Hz, 1H), 7.59-7.53 (m, 1H), 7.46-7.38 (m, 2H), 3.84 (dt, J=13.5, 7.5 Hz, 2H), 3.70-3.55 (m, 2H), 1.54-1.36 (m, 4H), 1.19 (s, 2H), 1.06 (s, 3H). MS (ES+) m/z 343 (M+1), $R_T$=1.12 min.

Example 25: Preparation of 4-(aminomethyl)-1-(3-(3-chlorophenyl)-1H-pyrazolo[3,4-b]pyrazin-6-yl)piperidin-4-ol 4-(aminomethyl)-1-(3-(3-chlorophenyl)-1H-pyrazolo[3,4-b]pyrazin-6-yl)piperidin-4-ol was prepared as schematically illustrated below.

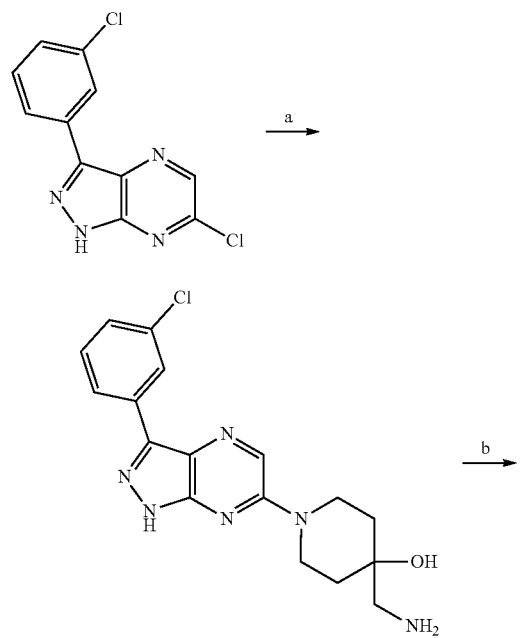

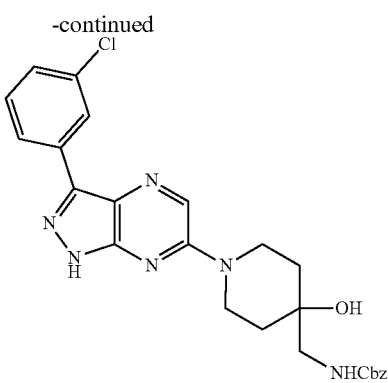

Step a: A mixture 6-chloro-3-(3-chlorophenyl)-1H-pyrazolo[3,4-b]pyrazine (75 mg, 0.28 mmol), benzyl ((4-hydroxypiperidin-4-yl)methyl)carbamate (85 mg, 0.28 mmol), $K_3PO_4$ (150 mg, 0.71 mmol) and DMAc (1 mL) was stirred at 80° C. for 18 h. The reaction mixture was diluted with EtOAc and water and transferred into a separation funnel. The layers were separated and the aqueous phase was extracted with EtOAc. The combined organic phases were washed with brine (3×), dried over MgSO4, filtered, and the volatiles were removed under reduced pressure. The resulting residue was purified by silica gel chromatography (10 to 70% gradient of EtOAc/hexanes) to benzyl ((1-(3-(3-chlorophenyl)-1H-pyrazolo[3,4-b]pyrazin-6-yl)-4-hydroxypiperidin-4-yl)methyl)carbamate (66 mg, 47%) as a yellow foam. MS (ES+) m/z 493.1 (M+1).

Step b: HBr in acid acetic (33% wt %, 1.5 mL) was added dropwise benzyl ((1-(3-(3-chlorophenyl)-1H-pyrazolo[3,4-b]pyrazin-6-yl)-4-hydroxypiperidin-4-yl)methyl)carbamate (80 mg, 0.37 mmol). The mixture was stirred for 1 hr at room temperature. Diethyl ether was then added and a solid crashed out. The liquid was removed and the solid was tritured with diethyl ether. The residue was diluted in water and purified by C18 chromatography (0% to 100% gradient of MeCN/(0.1% NH4HCO3 in water) to give 4-(aminomethyl)-1-(3-(3-chlorophenyl)-1H-pyrazolo[3,4-b]pyrazin-6-yl)piperidin-4-ol (12 mg, 22%) as a beige solid. $^1H$ NMR (400 MHz, DMSO-d6) δ 8.52 (s, 1H), 8.44-8.29 (m, 1H), 8.23 (ddd, J=8.7, 4.9, 3.6 Hz, 1H), 7.50 (t, J=7.9 Hz, 1H), 7.45-7.38 (m, 1H), 4.23 (t, J=31.0 Hz, 2H), 4.09-3.78 (m, 2H), 2.68 (s, 2H), 1.75-1.40 (m, 4H). MS (ES+) m/z 359.1 (M+1).

Example 26: Preparation of (1-(3-(2-Chlorophenyl)-1H-pyrazolo[3,4-b]pyrazin-6-yl)-4-methoxypiperidin-4-yl)methanamine (1-(3-(2-Chlorophenyl)-1H-pyrazolo[3,4-b]pyrazin-6-yl)-4-methoxypiperidin-4-yl)methanamine was prepared as schematically illustrated below.

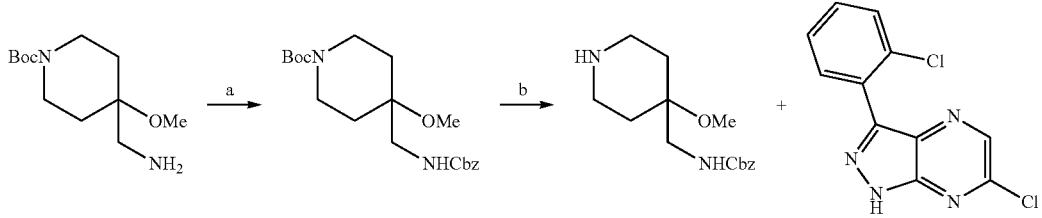

-continued

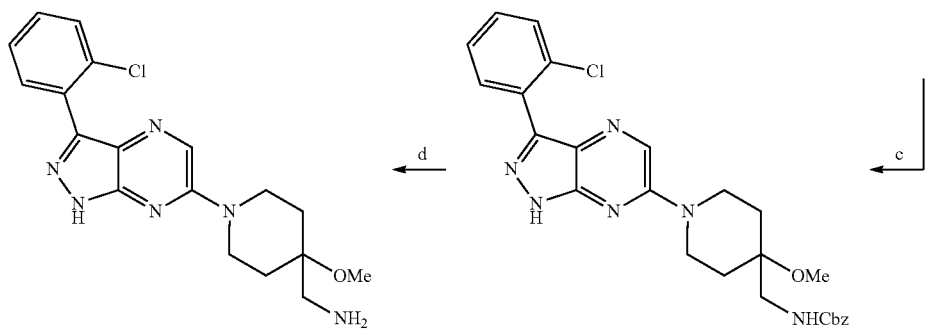

Step a: To a 100 mL round-bottom flask was added tert-butyl 4-(aminomethyl)-4-methoxypiperidine-1-carboxylate (500 mg, 2.05 mmol, 1.0 equiv). It was dissolved in a mixture of EtOH:H$_2$O (10:1) (10.3 mL, 0.2 M), and NaHCO$_3$ was added (361 mg, 4.30 mmol, 2.0 equiv). The reaction was initiated by addition of CbzCl (367 mg, 0.31 mL, 2.15 mmol, 1.05 equiv) dropwise. The cloudy solution was stirred at rt for 3 hours. After that period, LCMS showed full conversion to the desired Cbz-protected amine. The reaction was diluted with EtOAc (40 mL) and water (20 mL). The biphasic mixture was transferred to a 125 mL extraction funnel and the layers were separated. The aqueous layer was extracted with EtOAc (3×30 mL) and the layers were combined, washed with brine (3×30 mL), dried over Na$_2$SO$_4$, filtered, and evaporated to dryness. It resulted in a clear oil which was analyzed by NMR showing the desired product and some other by-products arising from CbzCl. The crude protected amine was carried to the next step without further purification (750 mg, 96% yield). MS (ES+) m/z 379, 323, 279 (M+1), R$_T$=1.71 min.

Step b: To a 100 mL round-bottom flask was added tert-butyl 4-((((benzyloxy) carbonyl)amino)methyl)-4-methoxypiperidine-1-carboxylate (750 mg, 1.98 mmol, 1.0 equiv). It was dissolved in anhydrous DCM (10.0 mL, 0.2 M). TFA (7.5 mL, 80.0 mmol, 50 equiv) was then added dropwise to the reaction and the yellow solution was stirred for 1.5 hour at room temperature. After that period, LCMS showed full conversion to the desired deprotected amine. The reaction solvents were evaporated to dryness and the resulting residue was redissolved in EtOAc (40 mL) and quenched by addition of NaHCO$_3$ sat. aq. (20 mL) until pH was found to be 10-11. The biphasic mixture was transferred to a 125 mL extraction funnel and the layers were separated. The aqueous layer was extracted with EtOAc (3×30 mL) and the layers were combined, washed with brine (3×30 mL), dried over Na$_2$SO$_4$, filtered, and evaporated to dryness. It resulted in a yellow oil which was which was used in the next step without further purification (420 mg, 72% yield). MS (ES+) m/z 279 (M+1), R$_T$=1.08 min.

Step c: To a flame-dried, nitrogen-flushed 0.5-2.0 mL microwave vial equipped with a conic stirbar and a white 14-septum was added 6-chloro-3-(2-chlorophenyl)-1H-pyrazolo[3,4-b]pyrazine (45 mg, 0.170 mmol, 1.0 equiv), benzyl ((4-methoxypiperidin-4-yl)methyl)carbamate (95 mg, 0.340 mmol, 2.0 equiv) and K$_3$PO$_4$ (54 mg, 0.255 mmol, 1.5 equiv). The reactants were dissolved in DMAc (0.600 mL, 0.3 M), the vial was capped with a Teflon cap and the reaction was stirred at 90° C. overnight in a oil bath. The reaction was cooled back to RT and opened to air. The crude was diluted with EtOAc (20 mL) while being transferred to a 60 mL extraction funnel. A mix of NaHCO$_3$:brine (1:1) was added (10 mL) and the layers were extracted and separated. Aqueous layer was further extracted with EtOAc (2×10 mL) and layers were combined. The organic layer was then washed further with brine (3×10 mL), dried over Na$_2$SO$_4$, filtered, and evaporated to dryness. The crude was further purified by flash chromatography using a 4 g Silicycle column using a gradient of 100% Hexanes to 80% EtOAc in hexanes. The product came off at around 50-60% EtOAc in hexanes as translucent fractions. The fractions containing the desired product were evaporated to dryness. It resulted in a yellow film which consisted in pure product by NMR (75 mg, 87% yield). MS (ES+) m/z 507 (M+1), R$_T$=1.65 min.

Step d: To a 100 mL round bottom flask equipped with a magnetic stirbar was added benzyl ((1-(3-(2-chlorophenyl)-1H-pyrazolo[3,4-b]pyrazin-6-yl)-4-methoxypiperidin-4-yl) methyl)carbamate (75 mg, 0.146 mmol, 1.00 equiv). It was directly reacted with excess amounts of HBr 33% in AcOH (1.5 mL) and the reaction was stirred at RT until it was judged to be finished by LCMS. After 30 minutes, water (10 mL) was added to the reaction followed by EtOAc (10 mL) while transferring the biphasic mixture to a 60 mL extraction funnel. The aqueous layer was further extracted with EtOAc (2×20 mL) and the organic layer was disposed of. Then, the aqueous layer was basified by addition of Na$_2$CO$_3$ sat. aq. until pH was found to be 11-12 and it was further diluted with DCM (15 mL). The aqueous layer was back-extracted and layers were separated. The aqueous layer was extracted with more DCM (3×20 mL). Organic layer was then dried over Na$_2$SO$_4$, filtered, and evaporated to dryness. The product was lyophilized overnight in a mixture of MeCN and H$_2$O. It procures a white powder which consisted in the desired product (43 mg, 80% yield, >99.5% purity). $^1$H NMR (400 MHz, CDCl$_3$) δ 8.28 (s, 1H), 7.83-7.75 (m, 1H), 7.57-7.51 (m, 1H), 7.44-7.33 (m, 2H), 4.20 (dt, J=13.5, 8.0 Hz, 2H), 3.44-3.35 (m, 2H), 3.26 (s, 3H), 2.73 (s, 2H), 1.98 (dd, J=13.5, 3.5 Hz, 2H), 1.58-1.50 (m, 2H), 1.25 (s, 2H). MS (ES+) m/z 373 (M+1), R$_T$=1.14 min.

Example 27: Preparation of (1-(3-(2-Chlorophenyl)-1H-pyrazolo[3,4-b]pyrazin-6-yl)-4-fluoropiperidin-4-yl)methanamine (1-(3-(2-Chlorophenyl)-1H-pyrazolo[3,4-b]pyrazin-6-yl)-4-fluoropiperidin-4-yl)methanamine was prepared as schematically illustrated below.

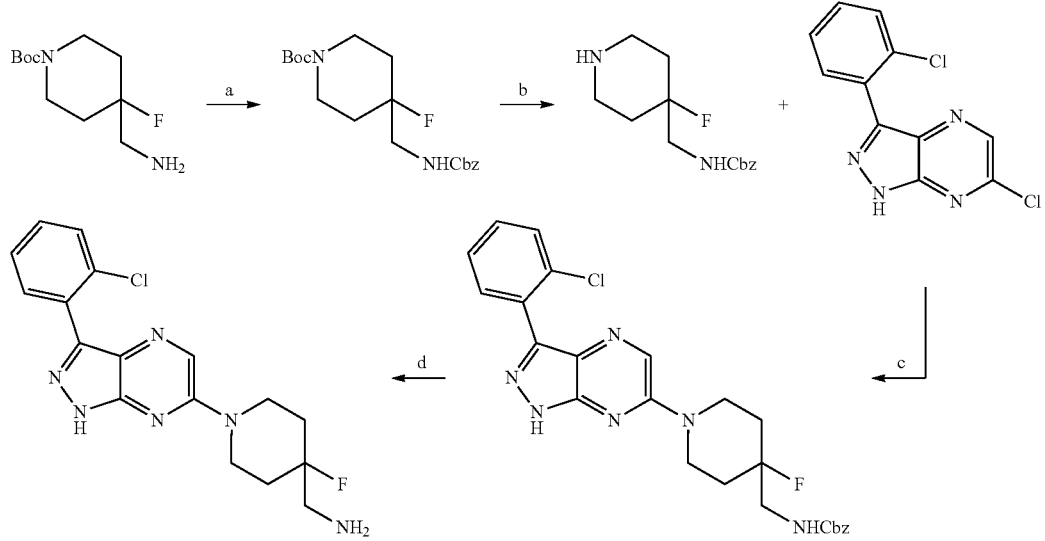

Step a: To a 100 mL round-bottom flask was added tert-butyl 4-(aminomethyl)-4-fluoropiperidine-1-carboxylate (500 mg, 2.15 mmol, 1.0 equiv). It was dissolved in a mixture of EtOH:H$_2$O (10:1) (10.8 mL, 0.2 M), and NaHCO$_3$ was added (361 mg, 4.30 mmol, 2.0 equiv). The reaction was initiated by addition of CbzCl (386 mg, 0.32 mL, 2.26 mmol, 1.05 equiv) dropwise. The cloudy solution was stirred at rt for 3 hours. After that period, LCMS showed full conversion to the desired Cbz-protected amine. The reaction was diluted with EtOAc (40 mL) and water (20 mL). The biphasic mixture was transferred to a 125 mL extraction funnel and the layers were separated. The aqueous layer was extracted with EtOAc (3×30 mL) and the layers were combined, washed with brine (3×30 mL), dried over Na$_2$SO$_4$, filtered, and evaporated to dryness. It resulted in a clear oil which was analyzed by NMR showing the desired product and some other by-products arising from CbzCl. The crude protected amine was carried to the next step without further purification. MS (ES+) m/z 367.2 (M+1), R$_T$=1.90 min.

Step b: To a 100 mL round-bottom flask was added tert-butyl 4-((((benzyloxy) carbonyl)amino)methyl)-4-fluoropiperidine-1-carboxylate (787 mg, 2.15 mmol, 1.0 equiv). It was dissolved in anhydrous DCM (10.8 mL, 0.2 M). TFA (8.2 mL, 107.5 mmol, 50 equiv) was then added dropwise to the reaction and the yellow solution was stirred for 1.5 hour at room temperature. After that period, LCMS showed full conversion to the desired deprotected amine. The reaction solvents were evaporated to dryness and the resulting residue was redissolved in EtOAc (40 mL) and quenched by addition of NaHCO$_3$ sat. aq. (20 mL) until pH was found to be 10-11. The biphasic mixture was transferred to a 125 mL extraction funnel and the layers were separated. The aqueous layer was extracted with EtOAc (3×30 mL) and the layers were combined, washed with brine (3×30 mL), dried over Na$_2$SO$_4$, filtered, and evaporated to dryness. It resulted in a yellow solid which was which was used in the next step without further purification (535 mg, 98% yield). MS (ES+) m/z 253 (M+1), R$_T$=1.07 min.

Step c: To a flame-dried, nitrogen-flushed 0.5-2.0 mL microwave vial equipped with a conic stirbar and a white 14-septum was added 6-chloro-3-(2-chlorophenyl)-1H-pyrazolo[3,4-b]pyrazine (45 mg, 0.170 mmol, 1.0 equiv), benzyl ((4-fluoropiperidin-4-yl)methyl)carbamate (91 mg, 0.340 mmol, 2.0 equiv) and K$_3$PO$_4$ (54 mg, 0.255 mmol, 1.5 equiv). The reactants were dissolved in DMAc (0.600 mL, 0.3 M), the vial was capped with a Teflon cap and the reaction was stirred at 90° C. overnight in a oil bath. The reaction was cooled back to RT and opened to air. The crude was diluted with EtOAc (20 mL) while being transferred to a 60 mL extraction funnel. A mix of NaHCO$_3$:brine (1:1) was added (10 mL) and the layers were extracted and separated. Aqueous layer was further extracted with EtOAc (2×10 mL) and layers were combined. The organic layer was then washed further with brine (3×10 mL), dried over Na$_2$SO$_4$, filtered, and evaporated to dryness. The crude was further purified by flash chromatography using a 4 g Silicycle column using a gradient of 100% Hexanes to 80% EtOAc in hexanes. The product came off at around 50-60% EtOAc in hexanes as translucent fractions. The fractions containing the desired product were evaporated to dryness. It resulted in a yellow film which consisted in pure product by NMR (80 mg, 95% yield). MS (ES+) m/z 495 (M+1), R$_T$=1.63 min.

Step d: To a 100 mL round bottom flask equipped with a magnetic stirbar was added benzyl ((1-(3-(2-chlorophenyl)-1H-pyrazolo[3,4-b]pyrazin-6-yl)-4-fluoropiperidin-4-yl) methyl)carbamate (80 mg, 0.161 mmol, 1.00 equiv). It was directly reacted with excess amounts of HBr 33% in AcOH (1.5 mL) and the reaction was stirred at RT until it was judged to be finished by LCMS. After 30 minutes, water (10 mL) was added to the reaction followed by EtOAc (10 mL) while transferring the biphasic mixture to a 60 mL extraction funnel. The aqueous layer was further extracted with EtOAc (2×20 mL) and the organic layer was disposed of. Then, the aqueous layer was basified by addition of Na$_2$CO$_3$ sat. aq. until pH was found to be 11-12 and it was further diluted with DCM (15 mL). The aqueous layer was back-extracted and layers were separated. The aqueous layer was extracted with more DCM (3×20 mL). Organic layer was then dried over Na$_2$SO$_4$, filtered, and evaporated to dryness. The product was lyophilized overnight in a mixture of MeCN and H$_2$O. It procures a white powder which consisted in the desired product (39 mg, 68% yield, >99.5% purity). $^1$H NMR (400 MHz, CDCl$_3$) δ 8.30 (s, 1H), 7.83-7.76 (m, 1H), 7.57-7.50 (m, 1H), 7.42-7.34 (m, 2H), 4.20 (dt, J=13.5, 4.0 Hz, 2H), 3.42 (td, J=13.5, 2.9 Hz, 2H), 2.85 (d, J=20.3 Hz, 2H), 2.11-2.02 (m, 2H), 1.78-1.62 (m, 4H). MS (ES+) m/z 361 (M+1), R$_T$=1.14 min.

Example 28: Preparation of (1-(3-(2-chlorophenyl)-1H-pyrazolo[3,4-b]pyrazin-6-yl)-4-(methoxymethyl)piperidin-4-yl)methanamine (1-(3-(2-chlorophenyl)-1H-pyrazolo[3,4-b]pyrazin-6-yl)-4-(methoxymethyl)piperidin-4-yl)methanamine was prepared as schematically illustrated below.

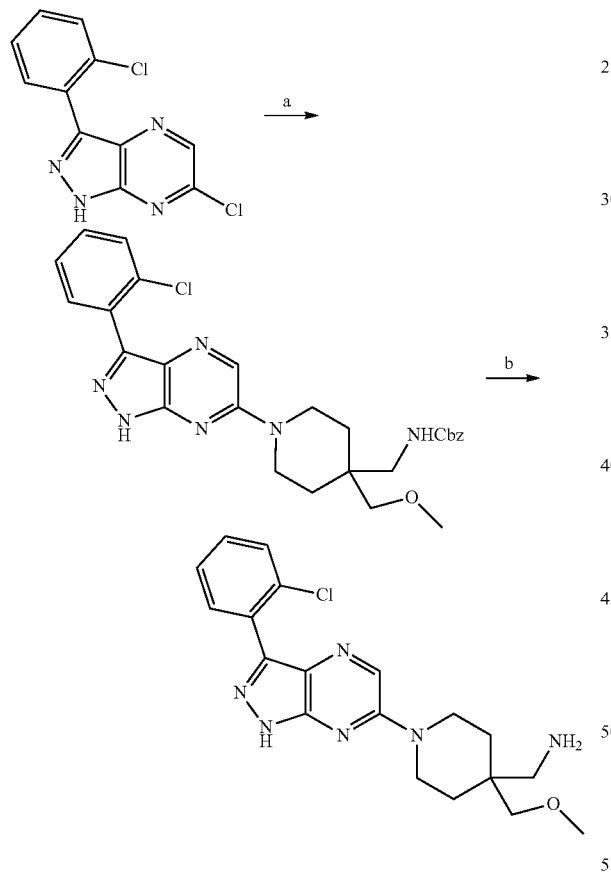

Step a: A mixture of 6-chloro-3-(2-chlorophenyl)-1H-pyrazolo[3,4-b]pyrazine (25 mg, 0.094 mmol), benzyl ((4-(methoxymethyl)piperidin-4-yl)methyl)carbamate (55 mg, 0.19 mmol) and potassium phosphate tribasic (30 mg, 0.14 mmol) are dissolved in N-methyl-2-pyrrolidone (0.4 mL) and the mixture is stirred at 90° C. for 2 h. The reaction mixture is cooled to room temperature, poured into water (10 mL) and extracted with dichloromethane (4×15 mL). The organic layers were combined, washed with a sat. aqueous NaHCO$_3$ solution (20 mL), brine (20 mL), dried over anhydrous Na$_2$SO$_4$, filtered and concentrated under reduced pressure. The pale yellow crude is purified by reverse phase chromatography (35 to 75% gradient of acetonitrile/10 mM aqueous ammonium formate) to give benzyl ((1-(3-(2-chlorophenyl)-1H-pyrazolo [3,4-b]pyrazin-6-yl)-4-(methoxymethyl)piperidin-4-yl)methyl)carbamate (43 mg, 88%) as a pale yellow oil. MS m/z 521.35 [M+H]$^+$.

Step b: In a 10-mL round bottomed flask, benzyl ((1-(3-(2-chlorophenyl)-1H-pyrazolo[3,4-b]pyrazin-6-yl)-4-(methoxymethyl)piperidin-4-yl)methyl)carbamate (43 mg, 0.083 mmol) is slowly dissolved in 33% hydrobromic acid in acetic acid (1 mL), at 0-4° C. The resulting yellow-orange mixture is stirred at this temperature for 30 min and allowed to progressively reach room temperature. The reaction is stirred an additional 30 min at room temperature. The mixture is slowly dropped into diethyl ether (20 mL). The yellow precipitate formed is filtered though filter paper, washed with diethyl ether (4-5 mL). The resulting residue is purified by reverse phase chromatography (10 to 50% gradient of acetonitrile/10 mM aqueous ammonium bicarbonate) to give (1-(3-(2-chlorophenyl)-1H-pyrazolo[3,4-b]pyrazin-6-yl)-4-(methoxymethyl)piperidin-4-yl)methanamine (19 mg, 60%) as an hygroscopic beige solid. $^1$H NMR (500 MHz, DMSO-d$_6$) δ 8.40 (s, 1H), 8.34 (br s, 1H), 7.77-7.73 (m, 1H), 7.62-7.57 (m, 1H), 7.49-7.43 (m, 2H), 3.78-3.64 (m, 6H), 3.28 (s, 3H), 2.68 (br s, 2H), 1.53 (d, J=5.6 Hz, 2H), 1.52 (d, J=5.7 Hz, 2H). MS m/z 387.2 [M+H]$^+$.

Example 29: Preparation of (1-(3-(2-Methoxyphenyl)-1H-pyrazolo[3,4-b]pyrazin-6-yl)-4-methylpiperidin-4-yl)methanamine (1-(3-(2-Methoxyphenyl)-1H-pyrazolo[3,4-b]pyrazin-6-yl)-4-methylpiperidin-4-yl)methanamine was prepared as schematically illustrated below.

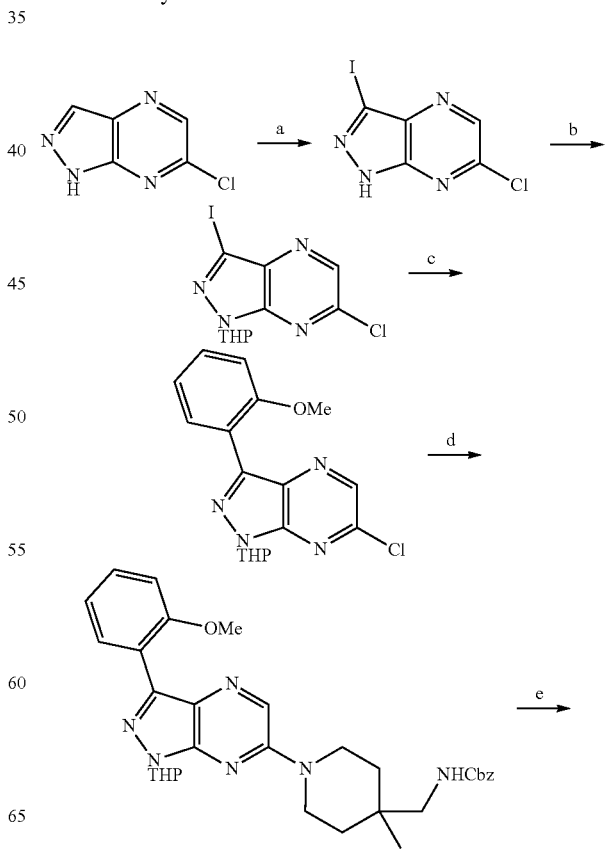

-continued

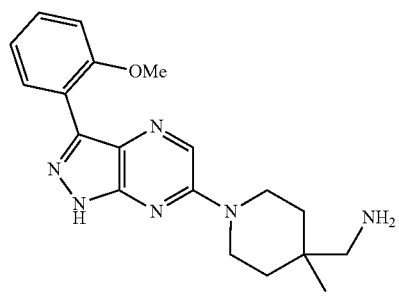

Step a: HBF₄ (48% aq. solution, 0.23 mL, 1.80 mmol) was added to a mixture of 6-chloro-1H-pyrazolo[3,4-b]pyrazine (116 mg, 0.751 mmol), NIS (169 mg, 0.751 mmol) and MeCN (2.5 mL) and the resulting mixture was stirred for 2 h at 80° C. More NIS (85 85, 0.375 mmol) was added and the reaction mixture was stirred for 40 min at 80° C. The mixture was allowed to cool to RT and the suspension was filtered. The collected solid was washed with minimal amount of MeCN and dried under vacuum to give 6-chloro-3-iodo-1H-pyrazolo[3,4-b]pyrazine (165 mg, 78%) as a yellow solid. ¹H NMR (500 MHz, DMSO-d6) δ ppm 14.65 (s, 1H), 8.70 (s, 1H). MS (ES+) m/z 281.0 (M+1).

Step b: 3,4-Dihydro-2H-pyran (83 µL, 0.909 mmol) was added to a solution of 6-chloro-3-iodo-1H-pyrazolo[3,4-b]pyrazine (85 mg, 0.303 mmol) and p-TsOH.H₂O (17 mg, 0.091 mmol) in DCM (1.5 mL) at RT. The resulting mixture was stirred for 20 min at RT, quenched with saturated NaHCO₃ solution and diluted with EtOAc. The mixture was transferred into a separation funnel, the layers were separated and the aqueous phase was extracted with EtOAc. The combined organic phases were washed with brine, dried over MgSO4, filtered, and the volatiles were removed under reduced pressure. The resulting residue was purified by silica gel chromatography (0 to 30% gradient of EtOAc/hexanes) to give 6-chloro-3-iodo-1-(tetrahydro-2H-pyran-2-yl)-1H-pyrazolo[3,4-b]pyrazine (90 mg, 82%) as a white solid. ¹H NMR (500 MHz, CHLOROFORM-d) δ ppm 8.56 (s, 1H), 5.96 (dd, J=10.4, 2.6 Hz, 1H), 4.11 (ddt, J=8.3, 4.1, 1.9 Hz, 1H), 3.79 (td, J=11.5, 2.6 Hz, 1H), 2.69-2.60 (m, 1H), 2.19-2.13 (m, 1H), 2.01-1.95 (m, 1H), 1.85-1.72 (m, 2H), 1.67-1.62 (m, 1H). MS (ES+) m/z 281.0 (M-THP+H+1).

Step c: A vial was charged with 6-chloro-3-iodo-1-(tetrahydro-2H-pyran-2-yl)-1H-pyrazolo[3,4-b]pyrazine (40 mg, 0.110 mmol), 2-methoxyphenylboronic acid (18 mg, 0.115 mmol), Pd(dppf)Cl₂-DCM (9 mg, 0.011 mmol) and K₃PO₄ (70 mg, 0.329 mmol). The vial was purged with N₂, degassed 1,4-dioxane (0.9 mL) and degassed water (0.1 mL) was added, the vial was sealed and stirred at 80° C. for 16 h. Silica gel was added and the resulting mixture was concentrated under reduced pressure. The resulting residue was purified by silica gel chromatography (0 to 25% gradient of EtOAc/hexanes) to give 6-chloro-3-(2-methoxyphenyl)-1-(tetrahydro-2H-pyran-2-yl)-1H-pyrazolo[3,4-b]pyrazine (23 mg, 61%) as a light brown oil. MS (ES+) m/z 261.2 (M-THP+H+1).

Step d: A mixture of 6-chloro-3-(2-methoxyphenyl)-1-(tetrahydro-2H-pyran-2-yl)-1H-pyrazolo[3,4-b]pyrazine (23 mg, 0.067 mmol), benzyl ((4-methylpiperidin-4-yl)methyl)carbamate (35 mg, 0.133 mmol), K₃PO₄ (43 mg, 0.200 mmol) and DMAc (0.7 mL) was stirred at 80° C. for 18 h. The reaction mixture was diluted with EtOAc and water and transferred into a separation funnel. The layers were separated and the aqueous phase was extracted with EtOAc. The combined organic phases were washed with brine (3×), dried over MgSO4, filtered, and the volatiles were removed under reduced pressure. The resulting residue was purified by silica gel chromatography (10 to 70% gradient of EtOAc/hexanes) to give benzyl ((1-(3-(2-methoxyphenyl)-1-(tetrahydro-2H-pyran-2-yl)-1H-pyrazolo[3,4-b]pyrazin-6-yl)-4-methylpiperidin-4-yl)methyl)carbamate (12 mg, 32%) as a white foam. MS (ES+) m/z 571.4 (M+1).

Step e: HBr in AcOH (33%, 1.0 mL) was added to benzyl ((1-(3-(2-methoxyphenyl)-1-(tetrahydro-2H-pyran-2-yl)-1H-pyrazolo [3,4-b]pyrazin-6-yl)-4-methylpiperidin-4-yl)methyl)carbamate (12 mg, 0.021 mmol) and the resulting mixture was stirred at RT for 1 h before being concentrated to dryness under reduced pressure. The residue was diluted in water and purified by C18 chromatography (10% to 100% gradient of MeOH/(0.1% NH4HCO3 in water) to give (1-(3-(2-methoxyphenyl)-1H-pyrazolo[3,4-b]pyrazin-6-yl)-4-methylpiperidin-4-yl)methanamine (6 mg, 80%) as a white solid. ¹H NMR (500 MHz, DMSO-d6) δ ppm 8.40 (s, 1H), 7.78 (br s, 1H), 7.41 (ddd, J=8.4, 7.5, 1.8 Hz, 1H), 7.15 (d, J=8.4 Hz, 1H), 7.06 (t, J=7.4 Hz, 1H), 4.00-3.92 (m, 2H), 3.78 (s, 3H), 3.51-3.23 (m, 4H), 1.56-1.44 (m, 2H), 1.39-1.32 (m, 2H), 0.99 (s, 3H). MS (ES+) m/z 353.2 (M+1).

Example 30: Preparation of 1-(3-(2,3-dichlorophenyl)-1H-pyrazolo[3,4-b]pyrazin-6-yl)-4-methylpiperidin-4-amine 1-(3-(2,3-dichlorophenyl)-1H-pyrazolo[3,4-b]pyrazin-6-yl)-4-methylpiperidin-4-amine can be prepared using methods similar to those described above.

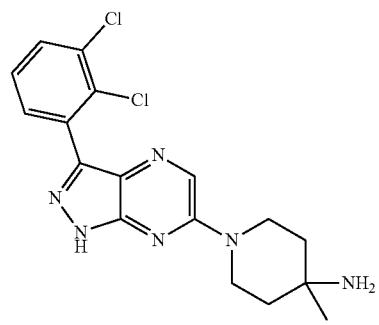

¹H NMR (400 MHz, CD₃OD): δ 8.33 (s, 1H), 7.68-7.65 (m, 1H), 7.59-7.57 (m, 1H), 7.57-7.43 (m, 1H), 3.98-3.91 (m, 2H), 3.82-3.78 (m, 2H), 1.72-1.63 (m, 4H), 1.26 (s, 3H). LCMS: [M+H]⁺ 377.1.

Example 31: Preparation of 4-methyl-1-(3-phenyl-1H-pyrazolo[3,4-b]pyrazin-6-yl)piperidin-4-amine 4-methyl-1-(3-phenyl-1H-pyrazolo[3,4-b]pyrazin-6-yl)piperidin-4-amine can be prepared using methods similar to those described above.

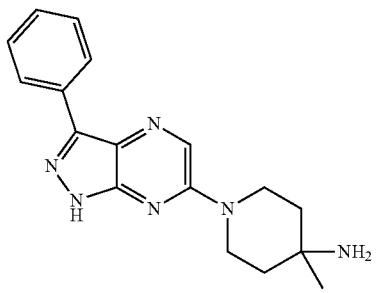 [SMILES: CC1(N)CCN(c2cnc3c(-c4ccccc4)n[nH]c3n2)CC1]

$^1$H NMR (400 MHz, CD$_3$OD): δ 8.40 (s, 1H), 8.29-8.31 (m, 2H), 7.46-7.50 (m, 2H), 7.42-7.39 (m, 1H), 3.93-3.89 (m, 2H), 3.83-3.79 (m, 2H), 1.72-1.65 (m, 4H), 1.26 (s, 3H). LCMS: [M+H]$^+$ 308.9.

Example 32: Preparation of 4-methyl-1-(3-(2-(trifluoromethyl)pyridin-3-yl)-1H-pyrazolo[3,4-b]pyrazin-6-yl)piperidin-4-amine 4-methyl-1-(3-(2-(trifluoromethyl)pyridin-3-yl)-1H-pyrazolo[3,4-b]pyrazin-6-yl)piperidin-4-amine can be prepared using methods similar to those described above.

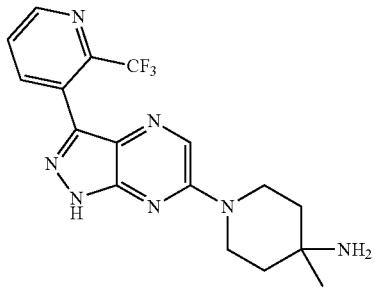 [SMILES: CC1(N)CCN(c2cnc3c(-c4cccnc4C(F)(F)F)n[nH]c3n2)CC1]

$^1$H NMR (400 MHz, CD$_3$OD): δ 8.81-8.79 (m, 1H), 8.34 (s, 1H), 8.19-8.16 (m, 1H), 7.82-7.78 (m, 1H), 3.99-3.92 (m, 2H), 3.83-3.79 (m, 2H), 1.72-1.66 (m, 4H), 1.27 (s, 3H). LCMS: [M+H]$^+$ 378.0.

Example 33: SHP2 Allosteric Inhibition Assay

SHP2 is allosterically activated through binding of bis-tyrosyl-phosphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

More specifically, the phosphatase reactions were performed at room temperature in 96-well black polystyrene plate, flat bottom, low flange, non-binding surface (Corning, Cat #3575) using a final reaction volume of 50 μl and the following assay buffer conditions: 60 mM HEPES, pH 7.2, 75 mM NaCl, 75 mM KCl, 1 mM EDTA 0.005% Brij-35, 5 mM DTT.

The inhibition of SHP2 by compounds of the invention (concentrations varying from 0.003-100 μM) was monitored using an assay in which 0.25 nM of SHP2 was incubated with of 0.5 LM of peptide IRS1_pY1172(dPEG8)pY1222 (sequence: H2N-LN(pY)IDLDLV(dPEG8)LST(pY)AS-INFQK-anide). After 30-60 minutes incubation at 25° C., the surrogate substrate DiFMUP (Invitrogen, cat #D6567, 100 μM final) was added to the reaction and the conversion of DiFMUP to 6,8-difluoro-7-hydroxyl-4-methylcoumarin (DiFMU) was monitored continuously for 10 minutes with excitation at 355 nm and emission at 460 nm using a microplate reader (PolarStar, BMG). The inhibitor dose response curves were analyzed using normalized IC$_{50}$ regression curve fitting with control based normalization. IC$_{50}$ results for compounds of the invention are shown in examples and Table 1. In Table 1, A means an IC$_{50}$ of less than 10 μM; B means an IC$_{50}$ equal to 10 μM but less than 100 μM; and C means an IC$_{50}$ of 100 μM or more.

TABLE 1

| Compound Number | Compound Structure | SHP2 IC$_{50}$ |
|---|---|---|
| 6 | 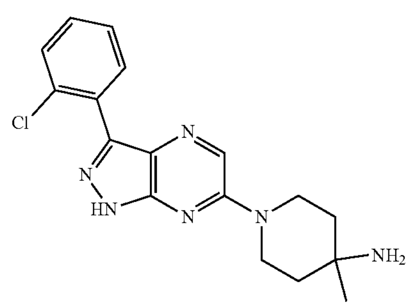 [SMILES: CC1(N)CCN(c2cnc3c(-c4ccccc4Cl)n[nH]c3n2)CC1] | A |

TABLE 1-continued
SHP2 IC$_{50}$ Assay Results
| Compound Number | Compound Structure | SHP2 IC$_{50}$ |
|---|---|---|
| 7 | 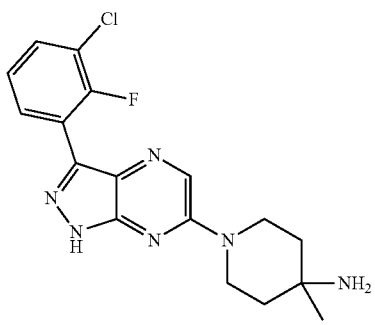 | A |
| 8 | 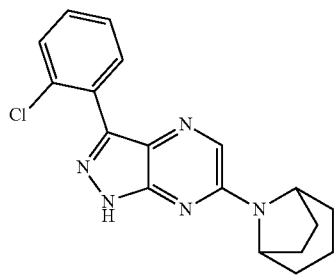 [SMILES: Clc1ccccc1-c1n[nH]c2nc(N3C4CCCC3CC4)cnc12] | B |
| 9 | 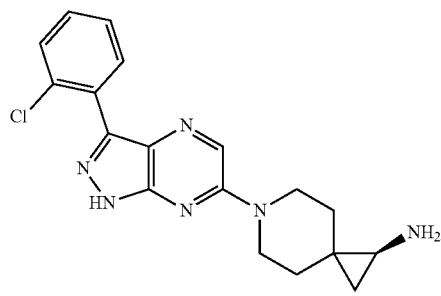 [SMILES: N[C@H]1CC12CCN(c1cnc3c(-c4ccccc4Cl)n[nH]c3n1)CC2] | A |
| 10 | 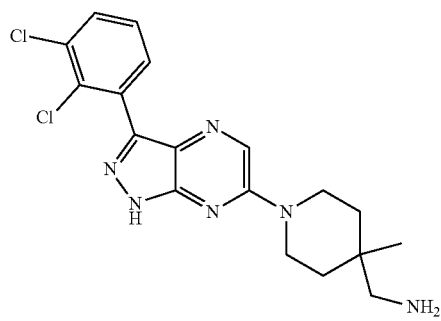 [SMILES: CC1(CN)CCN(c2cnc3c(-c4cccc(Cl)c4Cl)n[nH]c3n2)CC1] | A |

TABLE 1-continued
SHP2 IC$_{50}$ Assay Results
| Compound Number | Compound Structure | SHP2 IC$_{50}$ |
|---|---|---|
| 11 | 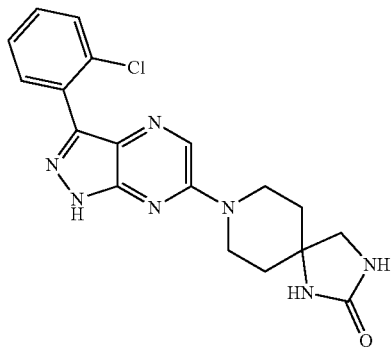 [SMILES: O=C1NCC2(CCN(c3cnc4c(-c5ccccc5Cl)n[nH]c4n3)CC2)N1] | B |
| 12 | 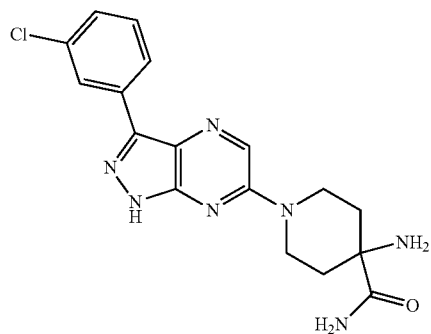 [SMILES: NC(=O)C1(N)CCN(c2cnc3c(-c4cccc(Cl)c4)n[nH]c3n2)CC1] | A |
| 13 | 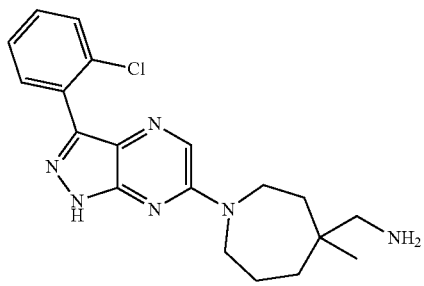 [SMILES: CC1(CN)CCCN(c2cnc3c(-c4ccccc4Cl)n[nH]c3n2)CC1] | A |
| 14 | 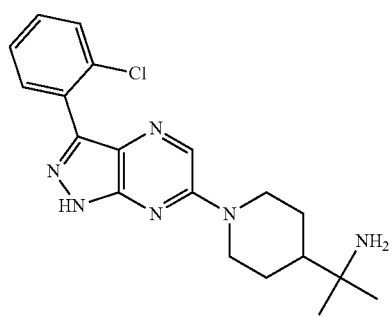 [SMILES: CC(C)(N)C1CCN(c2cnc3c(-c4ccccc4Cl)n[nH]c3n2)CC1] | B |

TABLE 1-continued

SHP2 IC$_{50}$ Assay Results

| Compound Number | Compound Structure | SHP2 IC$_{50}$ |
|---|---|---|
| 15 | 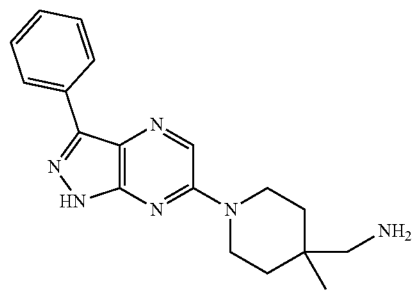 [SMILES: CC1(CN)CCN(c2cnc3c(-c4ccccc4)n[nH]c3n2)CC1] | A |
| 16 | 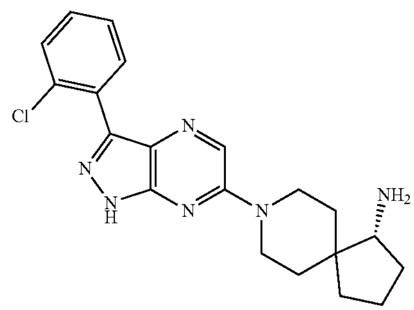 [SMILES: N[C@@H]1CCCC12CCN(c1cnc3c(-c4ccccc4Cl)n[nH]c3n1)CC2] | A |
| 17 | 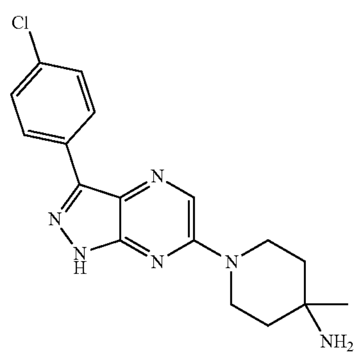 [SMILES: CC1(N)CCN(c2cnc3c(-c4ccc(Cl)cc4)n[nH]c3n2)CC1] | A |
| 18 | 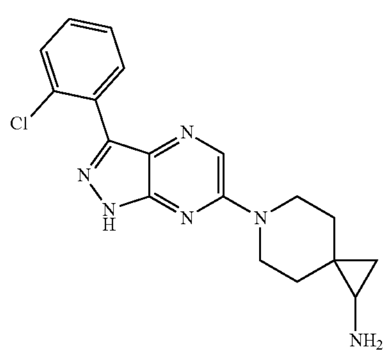 [SMILES: NC1CC12CCN(c1cnc3c(-c4ccccc4Cl)n[nH]c3n1)CC2] | A |

TABLE 1-continued

SHP2 IC$_{50}$ Assay Results

| Compound Number | Compound Structure | SHP2 IC$_{50}$ |
|---|---|---|
| 19 | 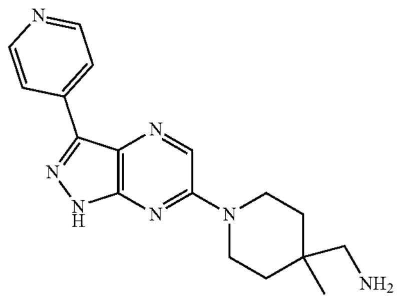 [SMILES: CC1(CN)CCN(c2cnc3c(-c4ccncc4)n[nH]c3n2)CC1] | A |
| 20 | 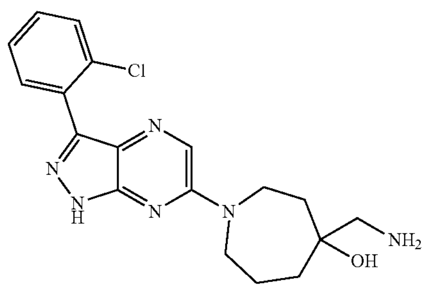 [SMILES: NCC1(O)CCCN(c2cnc3c(-c4ccccc4Cl)n[nH]c3n2)CC1] | A |
| F21 | 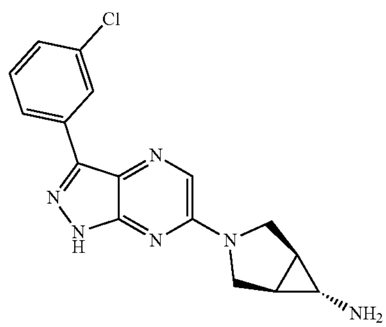 [SMILES: N[C@@H]1[C@H]2CN(c3cnc4c(-c5cccc(Cl)c5)n[nH]c4n3)C[C@@H]12] | A |
| 22 | 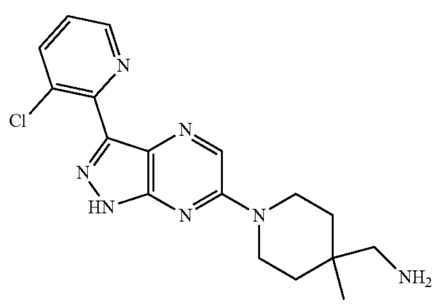 [SMILES: CC1(CN)CCN(c2cnc3c(-c4ncccc4Cl)n[nH]c3n2)CC1] | B |
| 23 | 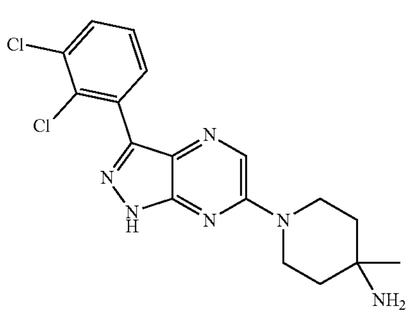 [SMILES: CC1(N)CCN(c2cnc3c(-c4cccc(Cl)c4Cl)n[nH]c3n2)CC1] | A |

TABLE 1-continued
SHP2 IC$_{50}$ Assay Results
| Compound Number | Compound Structure | SHP2 IC$_{50}$ |
|---|---|---|
| 24 | 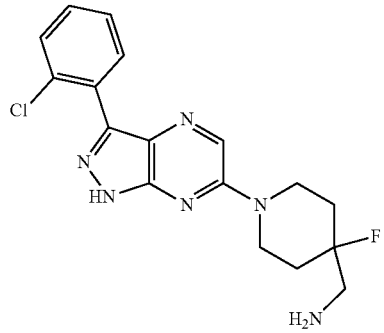 [SMILES: NCC1(F)CCN(c2cnc3c(-c4ccccc4Cl)n[nH]c3n2)CC1] | A |
| 25 | 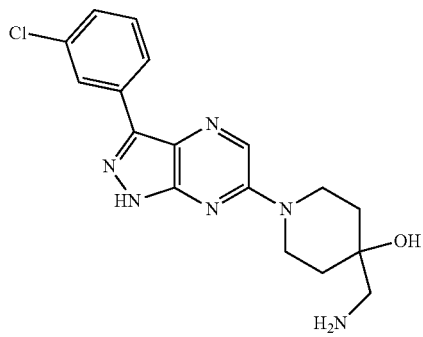 [SMILES: NCC1(O)CCN(c2cnc3c(-c4cccc(Cl)c4)n[nH]c3n2)CC1] | A |
| 26 | 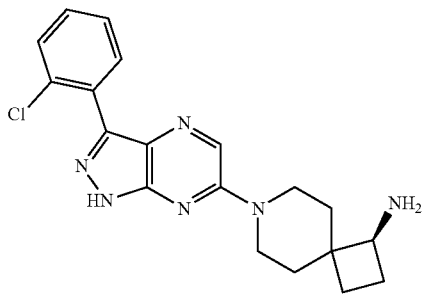 [SMILES: N[C@H]1CCC12CCN(c1cnc3c(-c4ccccc4Cl)n[nH]c3n1)CC2] | A |
| 27 | 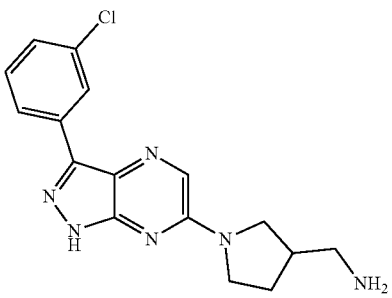 [SMILES: NCC1CCN(c2cnc3c(-c4cccc(Cl)c4)n[nH]c3n2)C1] | A |

TABLE 1-continued
SHP2 IC$_{50}$ Assay Results
| Compound Number | Compound Structure | SHP2 IC$_{50}$ |
|---|---|---|
| 28 | 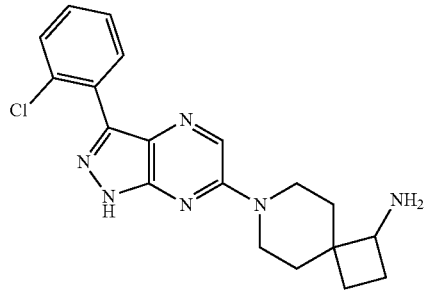 [SMILES: NC1CCC12CCN(c1cnc3c(-c4ccccc4Cl)n[nH]c3n1)CC2] | A |
| 29 | 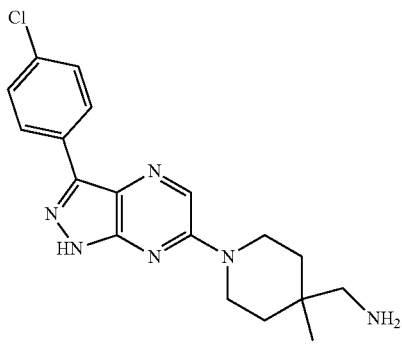 [SMILES: CC1(CN)CCN(c2cnc3c(-c4ccc(Cl)cc4)n[nH]c3n2)CC1] | A |
| 30 | 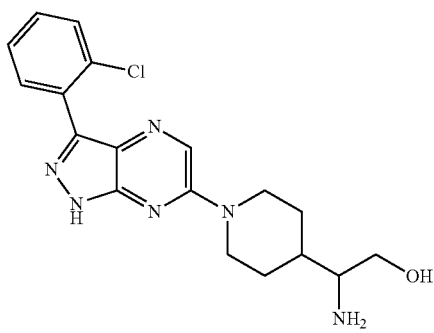 [SMILES: NC(CO)C1CCN(c2cnc3c(-c4ccccc4Cl)n[nH]c3n2)CC1] | A |
| 31 | 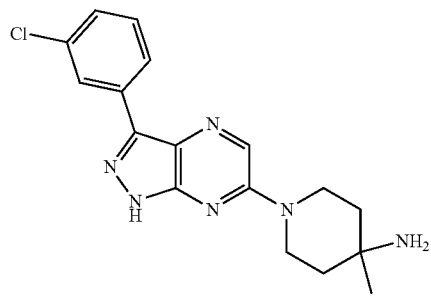 [SMILES: CC1(N)CCN(c2cnc3c(-c4cccc(Cl)c4)n[nH]c3n2)CC1] | A |

TABLE 1-continued

SHP2 IC$_{50}$ Assay Results

| Compound Number | Compound Structure | SHP2 IC$_{50}$ |
|---|---|---|
| 32 | 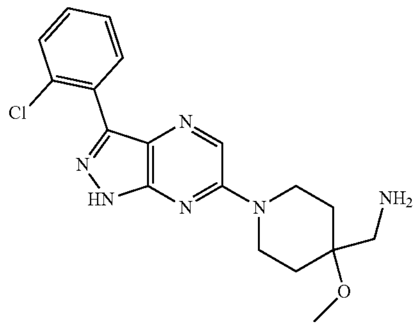 [SMILES: COC1(CN)CCN(c2cnc3c(-c4ccccc4Cl)n[nH]c3n2)CC1] | A |
| 33 | 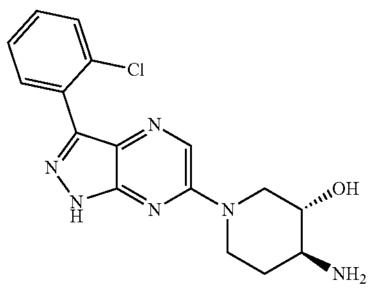 [SMILES: N[C@H]1CCN(c2cnc3c(-c4ccccc4Cl)n[nH]c3n2)C[C@@H]1O] | A |
| 34 | 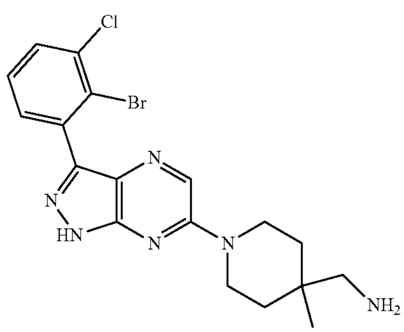 [SMILES: CC1(CN)CCN(c2cnc3c(-c4cccc(Cl)c4Br)n[nH]c3n2)CC1] | A |
| 35 | 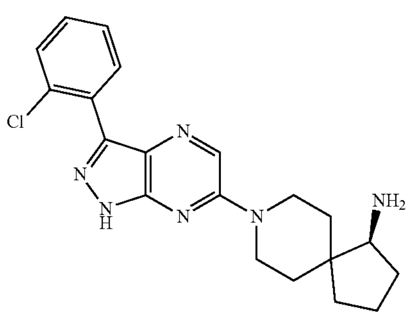 [SMILES: N[C@H]1CCCC12CCN(c1cnc3c(-c4ccccc4Cl)n[nH]c3n1)CC2] | A |
| 36 | 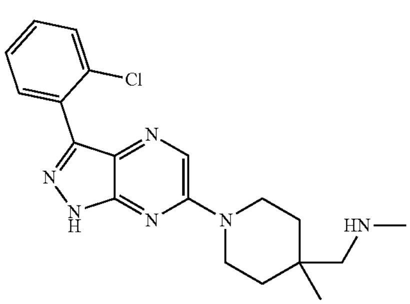 [SMILES: CNCC1(C)CCN(c2cnc3c(-c4ccccc4Cl)n[nH]c3n2)CC1] | B |

TABLE 1-continued

SHP2 IC$_{50}$ Assay Results

| Compound Number | Compound Structure | SHP2 IC$_{50}$ |
|---|---|---|
| 37 | 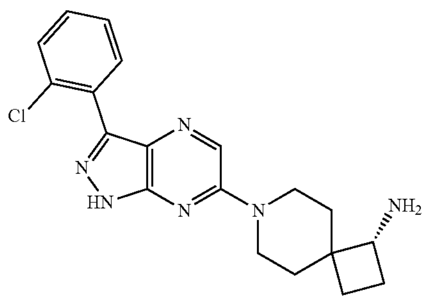 [SMILES: N[C@@H]1CCC12CCN(c1cnc3c(-c4ccccc4Cl)n[nH]c3n1)CC2] | B |
| 38 | 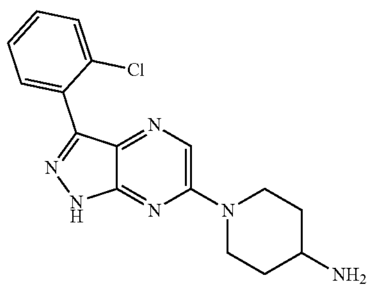 [SMILES: NC1CCN(c2cnc3c(-c4ccccc4Cl)n[nH]c3n2)CC1] | A |
| 39 | 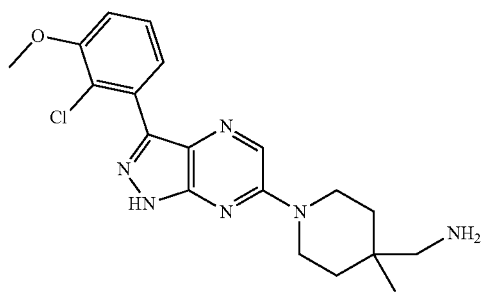 [SMILES: COc1cccc(-c2n[nH]c3nc(N4CCC(C)(CN)CC4)cnc23)c1Cl] | A |
| 40 | 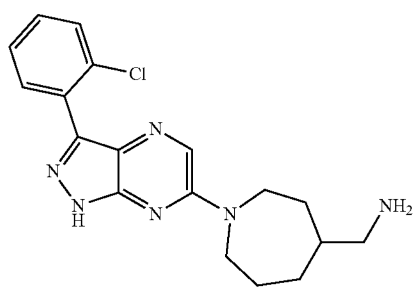 [SMILES: NCC1CCCN(c2cnc3c(-c4ccccc4Cl)n[nH]c3n2)CC1] | A |
| 41 | 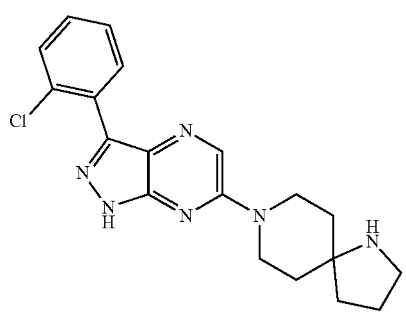 [SMILES: Clc1ccccc1-c1n[nH]c2nc(N3CCC4(CCCN4)CC3)cnc12] | A |

TABLE 1-continued

SHP2 IC$_{50}$ Assay Results

| Compound Number | Compound Structure | SHP2 IC$_{50}$ |
|---|---|---|
| 42 | 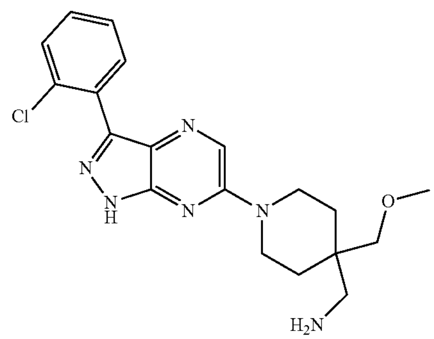 [SMILES: COCC1(CN)CCN(c2cnc3c(-c4ccccc4Cl)n[nH]c3n2)CC1] | A |
| 43 | 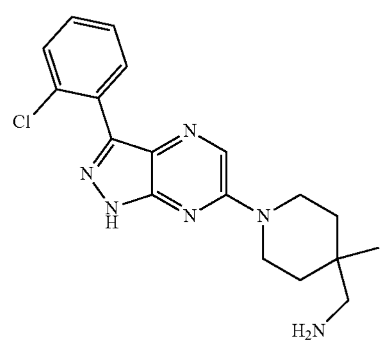 [SMILES: CC1(CN)CCN(c2cnc3c(-c4ccccc4Cl)n[nH]c3n2)CC1] | A |
| 44 | 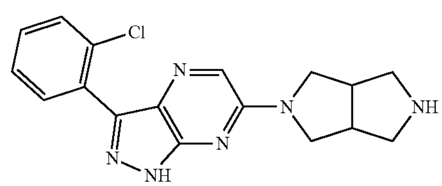 [SMILES: Clc1ccccc1-c1n[nH]c2nc(N3CC4CNCC4C3)cnc12] | A |
| 45 | 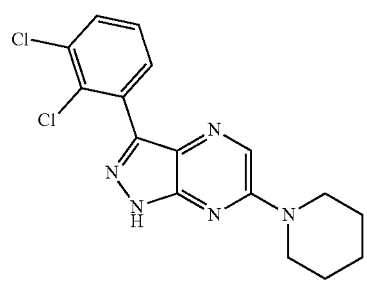 [SMILES: Clc1cccc(-c2n[nH]c3nc(N4CCCCC4)cnc23)c1Cl] | C |
| 46 | 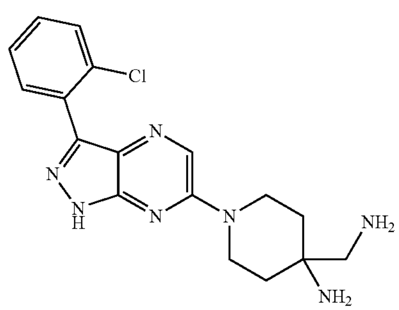 [SMILES: NCC1(N)CCN(c2cnc3c(-c4ccccc4Cl)n[nH]c3n2)CC1] | A |

TABLE 1-continued
SHP2 IC$_{50}$ Assay Results
| Compound Number | Compound Structure | SHP2 IC$_{50}$ |
|---|---|---|
| 47 | 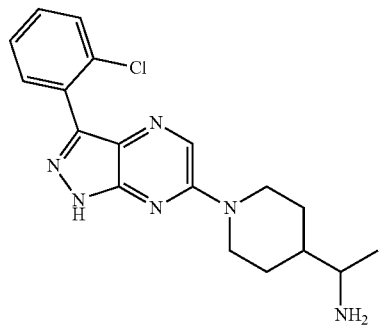 [SMILES: CC(N)C1CCN(c2cnc3c(-c4ccccc4Cl)n[nH]c3n2)CC1] | A |
| 48 | 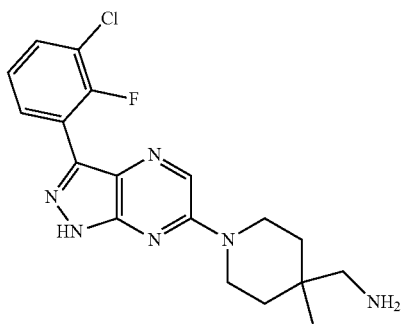 [SMILES: CC1(CN)CCN(c2cnc3c(-c4cccc(Cl)c4F)n[nH]c3n2)CC1] | A |
| 49 | 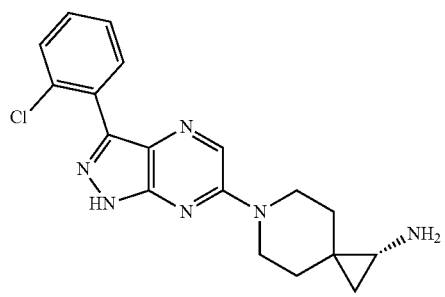 [SMILES: N[C@@H]1CC12CCN(c1cnc3c(-c4ccccc4Cl)n[nH]c3n1)CC2] | B |
| 50 | 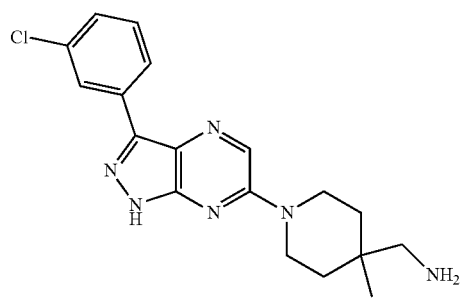 [SMILES: CC1(CN)CCN(c2cnc3c(-c4cccc(Cl)c4)n[nH]c3n2)CC1] | A |

TABLE 1-continued

SHP2 IC$_{50}$ Assay Results

| Compound Number | Compound Structure | SHP2 IC$_{50}$ |
|---|---|---|
| 51 | 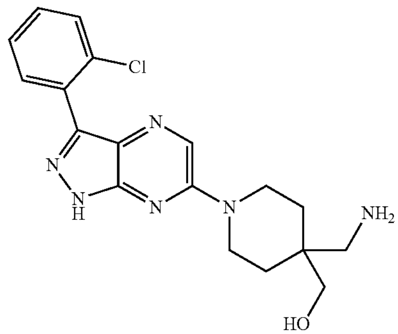 [SMILES: NCC1(CO)CCN(c2cnc3c(-c4ccccc4Cl)n[nH]c3n2)CC1] | A |
| 52 | 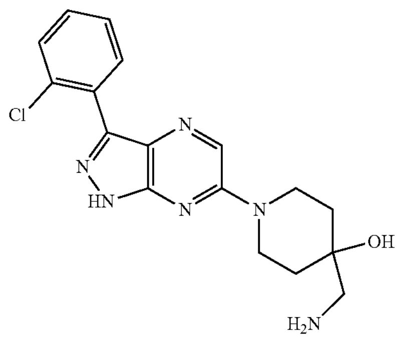 [SMILES: NCC1(O)CCN(c2cnc3c(-c4ccccc4Cl)n[nH]c3n2)CC1] | A |
| 53 | 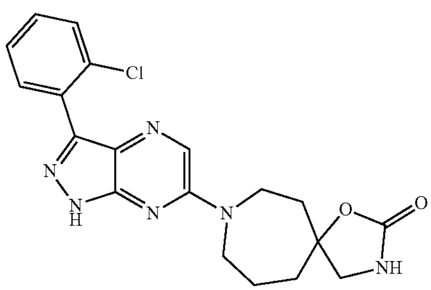 [SMILES: O=C1NCC2(CCCN(c3cnc4c(-c5ccccc5Cl)n[nH]c4n3)CC2)O1] | B |
| 54 | 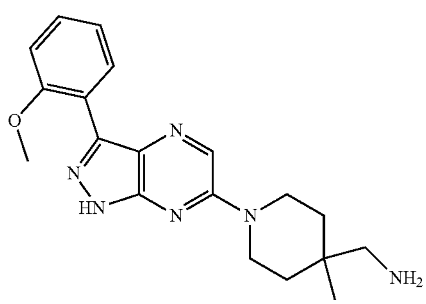 [SMILES: COc1ccccc1-c1n[nH]c2nc(N3CCC(C)(CN)CC3)cnc12] | A |
| 55 | 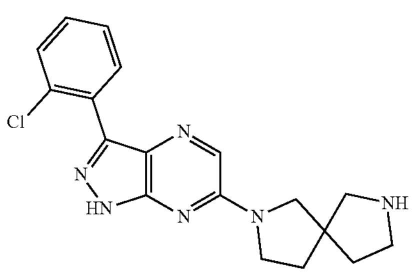 [SMILES: Clc1ccccc1-c1n[nH]c2nc(N3CCC4(CCNC4)C3)cnc12] | B |

TABLE 1-continued

SHP2 IC$_{50}$ Assay Results

| Compound Number | Compound Structure | SHP2 IC$_{50}$ |
|---|---|---|
| 56 | 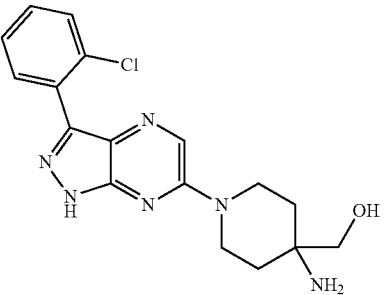 [SMILES: NC1(CO)CCN(c2cnc3c(-c4ccccc4Cl)n[nH]c3n2)CC1] | A |

INCORPORATION BY REFERENCE

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

EQUIVALENTS

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention.

What is claimed is:

1. A compound of formula (I), or a pharmaceutically acceptable salt thereof, (I)

wherein
$R^1$ is selected from the group consisting of

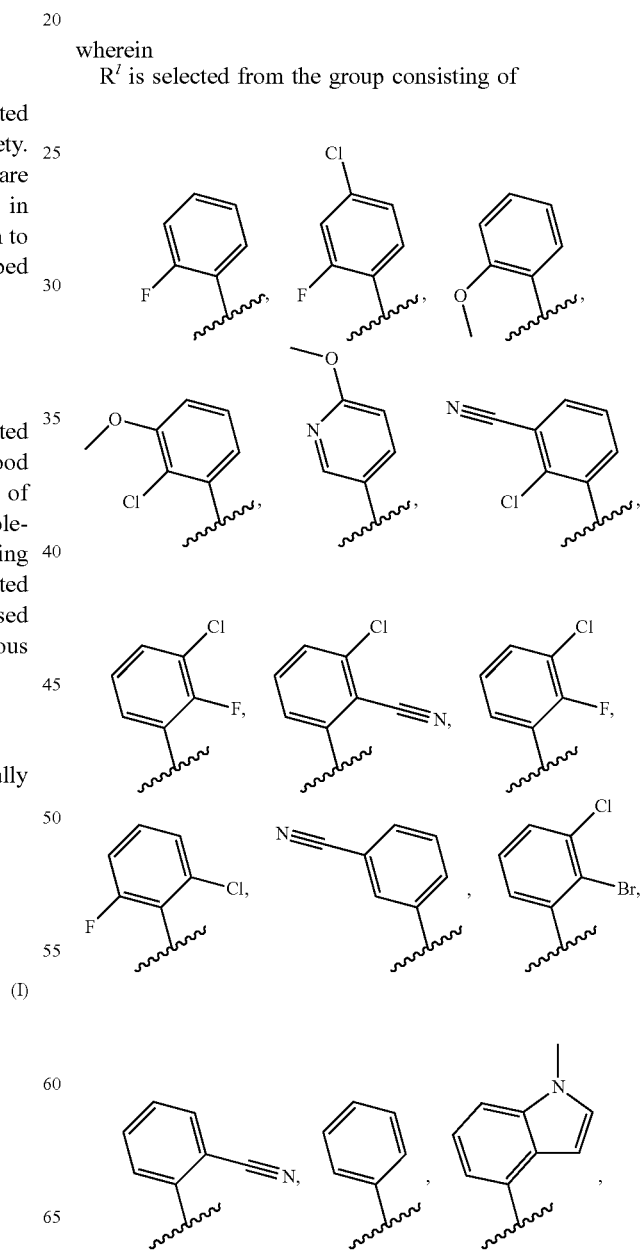

-continued

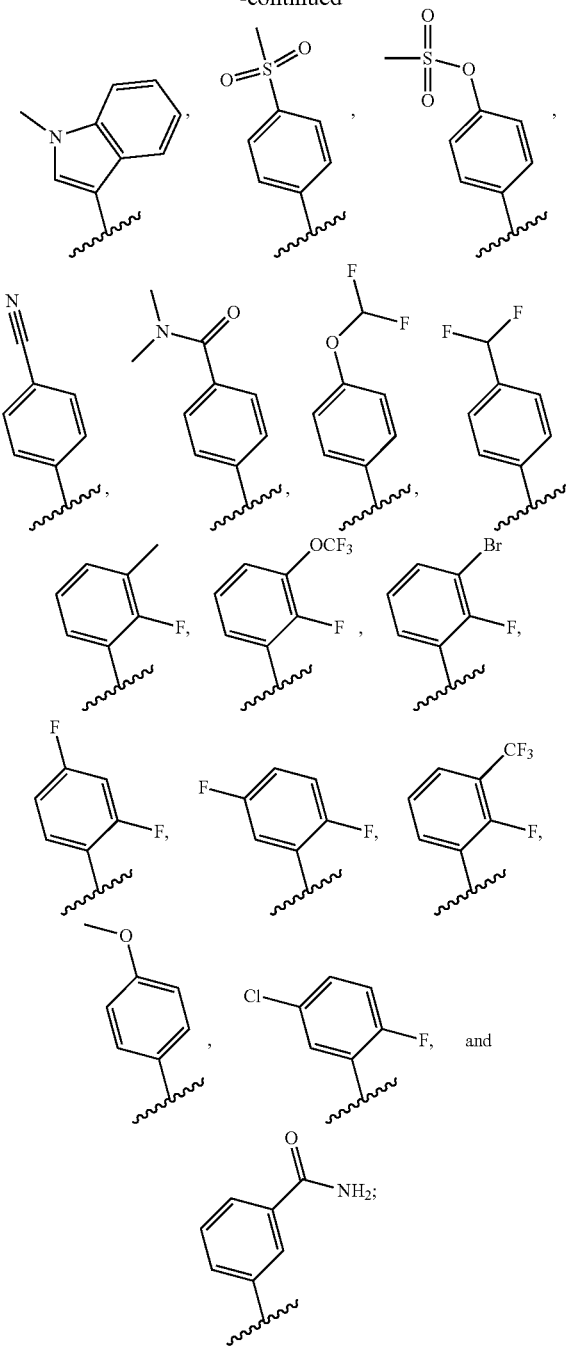

each of R⁴ and R⁵ is, independently, H, OH, (C₁-C₆)alkyl, —O(C₁-C₆)alkyl, —(C₁-C₆)alkyl-O—R⁶, —C(O)NH₂, —N(R⁶)₂, halogen, —(C₁-C₆)alkyl-N(R⁶)₂, or nitrile, wherein said —(C₁-C₆)alkyl, —O(C₁-C₆)alkyl, —(C₁-C₆)alkyl-O—R⁶, or —(C₁-C₆)alkyl-N(R⁶)₂ is optionally substituted with one or more substituents selected from the group consisting of —OH, —N(R⁶)₂, oxo, and halogen, wherein each R⁶ is independently H or —(C₁-C₆)alkyl;

or R⁴ and R⁵, taken together with the atoms to which they are attached, form a 3-7 membered carbocyclic or heterocyclic ring, which ring is optionally substituted with —OH, —(C₁-C₆)alkyl, —O(C₁-C₆)alkyl, —N(R⁶)₂, halogen, oxo, or nitrile;

each of R¹¹ and R¹² is, independently, H, —OH, —(C₁-C₆)alkyl, —O(C₁-C₆)alkyl, —(C₁-C₆)alkyl-O—R⁶, —C(O)NH₂, —N(R⁶)₂, halogen, —(C₁-C₆)alkyl-N(R⁶)₂, —CO₂H, or nitrile, wherein said —(C₁-C₆)alkyl, —O(C₁-C₆)alkyl, —(C₁-C₆)alkyl-O—R⁶, or —(C₁-C₆)alkyl-N(R⁶)₂ is optionally substituted with one or more substituents selected from the group consisting of —OH, —N(R⁶)₂, and halogen;

each of R^g and R^9 is, independently, H, —(C₁-C₆)alkyl, —(C₁-C₆)alkyl-N(R⁶ —OR⁶, —(C₁-C₆)alkyl-O—R⁶, —C(O)NH₂, —N(R⁶)₂, halogen, or nitrile;

and each of m and n is, independently, 0, 1, 2, or 3, with m+n being no more than 4.

2. The compound of claim 1, wherein m is an integer selected from 1 or 2; and n is 1.

3. The compound of claim 2, wherein R⁴ and R⁵ are independently H, —OH, —(C₁-C₃)alkyl, —O(C₁-C₃)alkyl, —(C₁-C₃)alkyl-O—R⁶, —C(O)NH₂, —N(R⁶)₂, halogen, —(C₁-C₃)alkyl-N(R⁶)₂, or nitrile, wherein said —(C₁-C₃)alkyl, —O(C₁-C₃)alkyl, —(C₁-C₃)alkyl-O—R⁶, or —(C₁-C₃)alkyl-N(R⁶)₂, is optionally substituted with one or more substituents selected from the group consisting of —OH, —N(R⁶)₂, and halogen;

or R⁴ and R⁵, taken together with the atoms to which they are attached, form a 3-7 membered carbocyclic or heterocyclic ring; and each R⁶ is independently H, —(C₁-C₃)alkyl.

4. The compound of claim 1, wherein the compound is selected from the group consisting of:

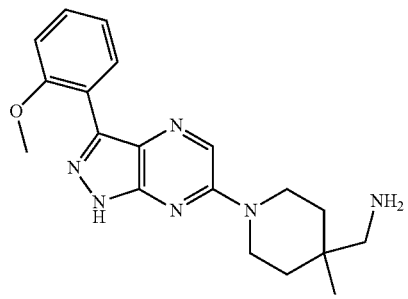 [SMILES: COc1ccccc1-c1n[nH]c2nc(N3CCC(C)(CN)CC3)cnc12]

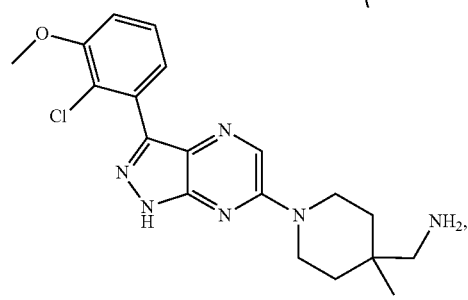

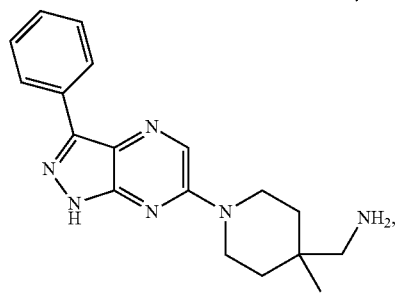

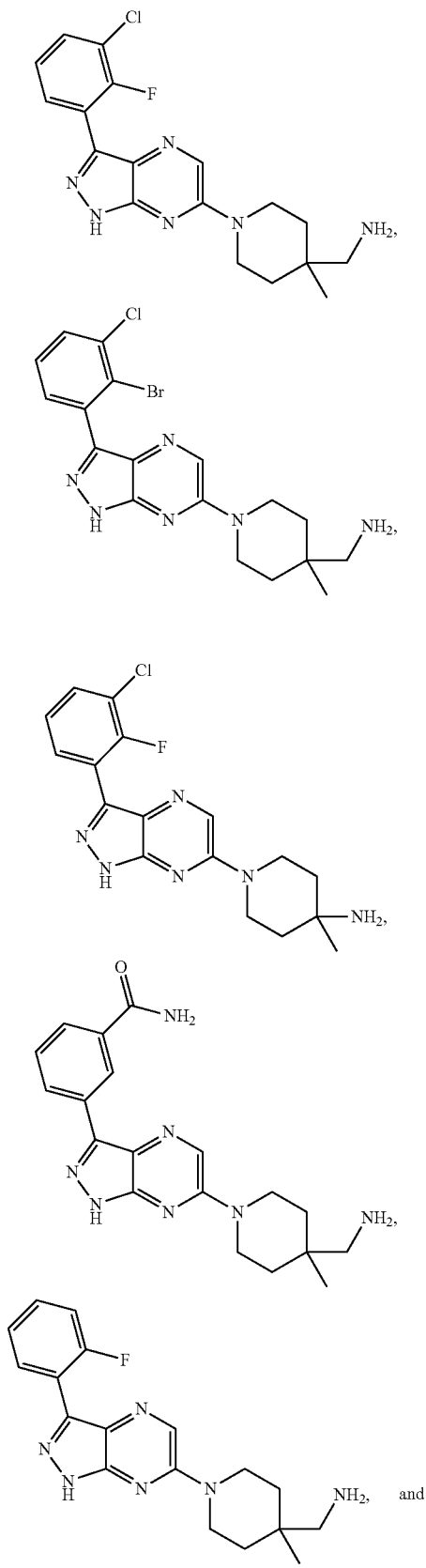
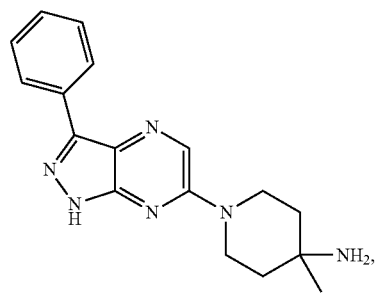
5. The compound of claim 1, wherein the compound is selected from the group consisting of:

-continued
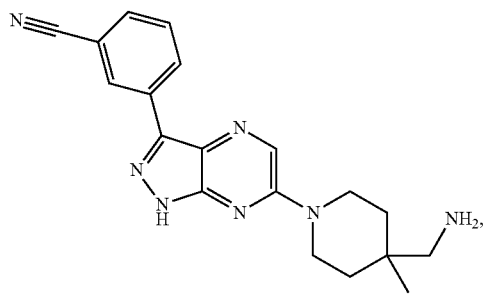
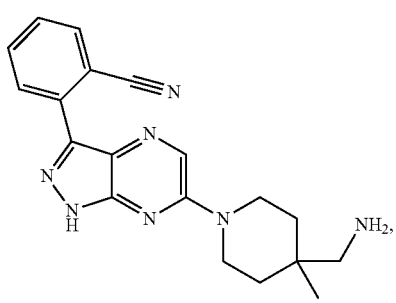
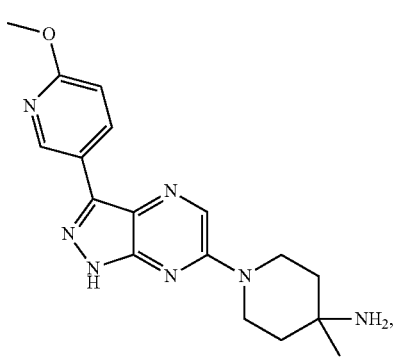
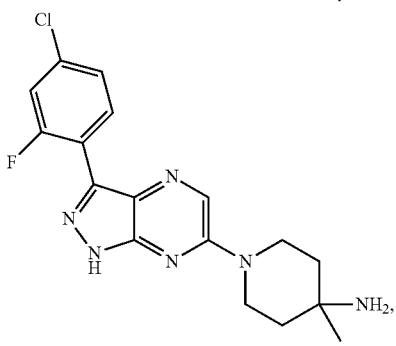
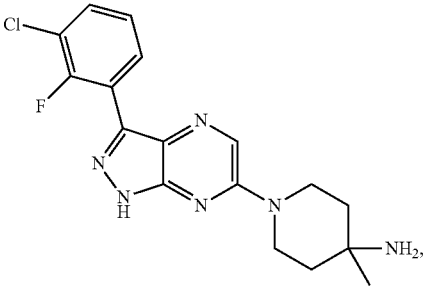
-continued
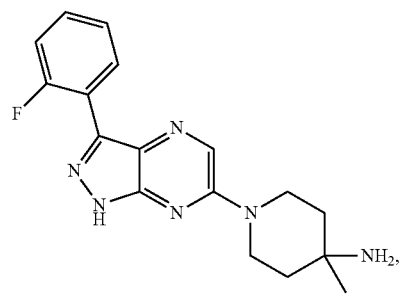
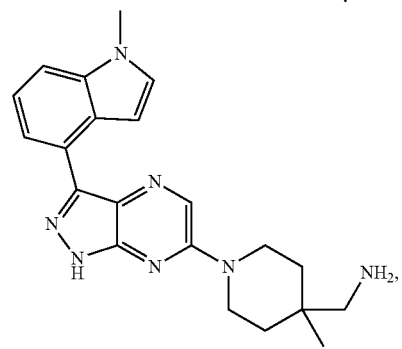
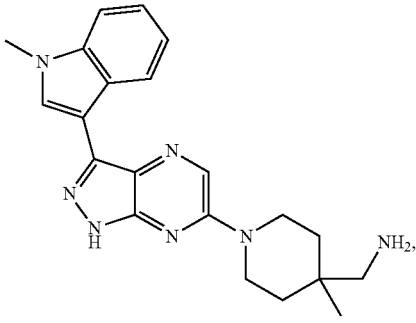
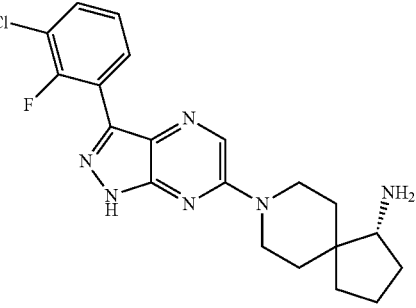
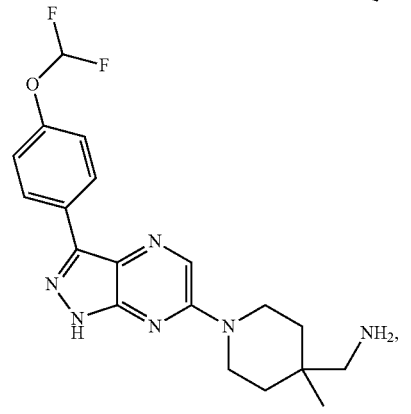

133
-continued
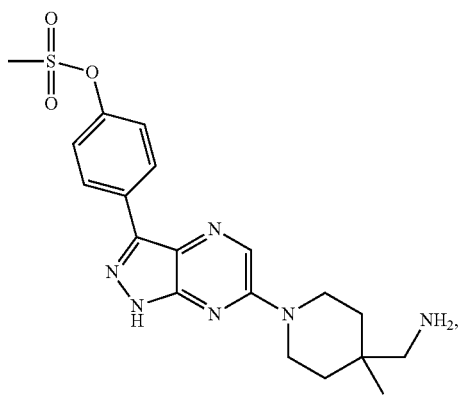
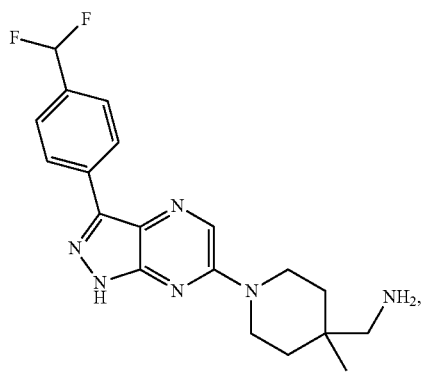
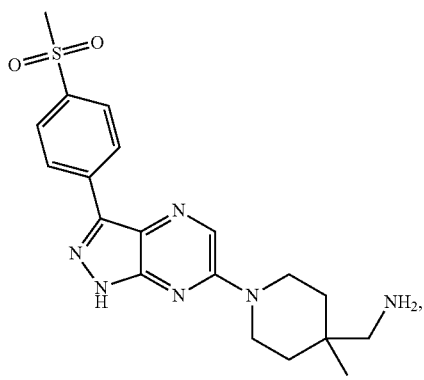
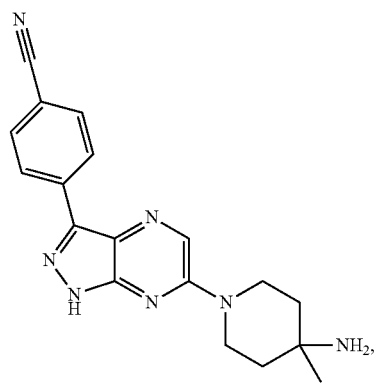
134
-continued
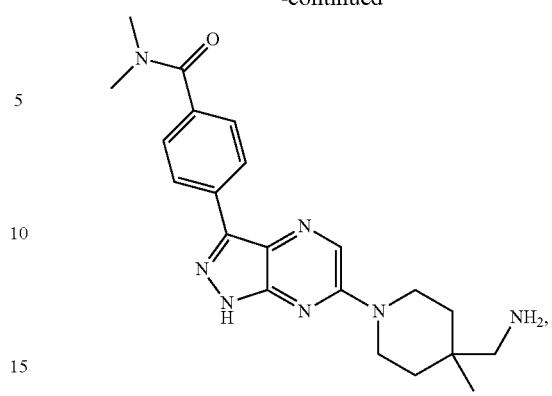
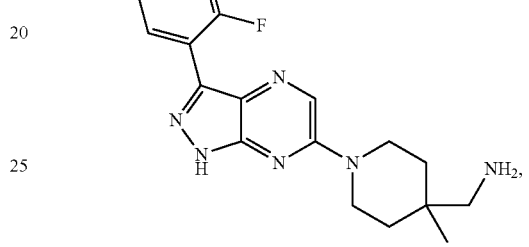
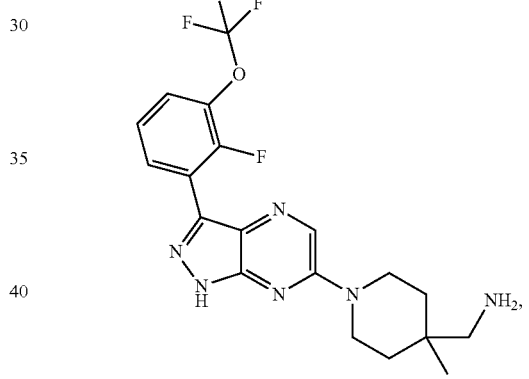
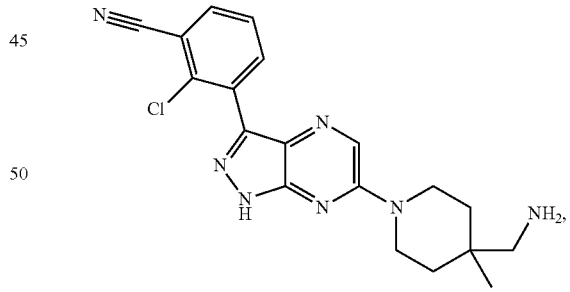
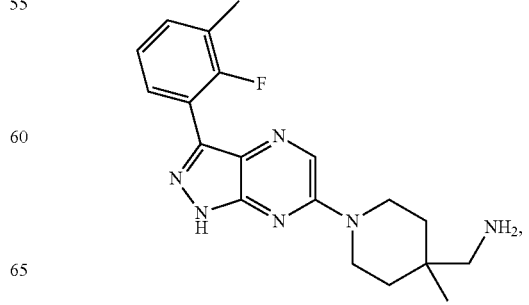

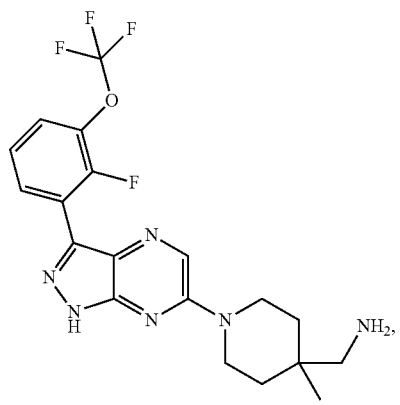
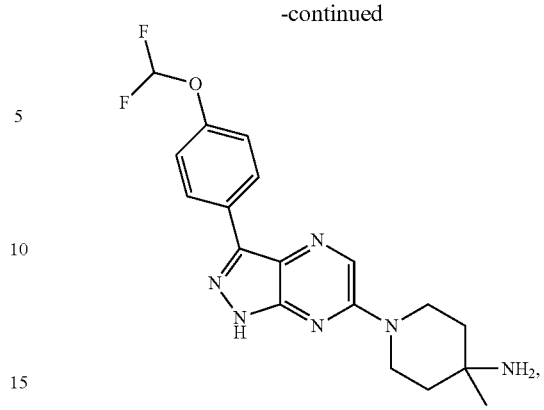
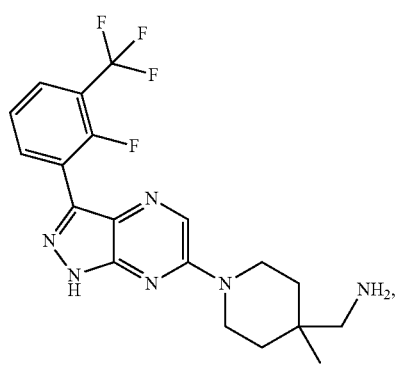
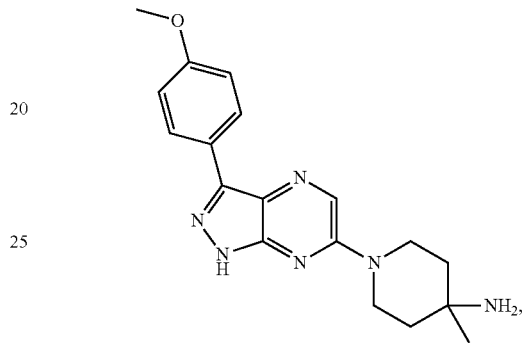
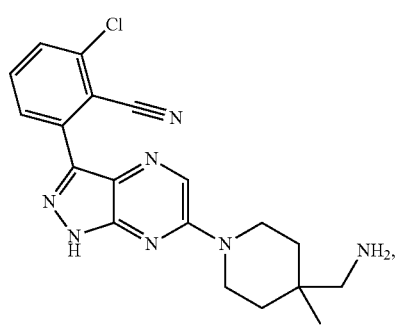
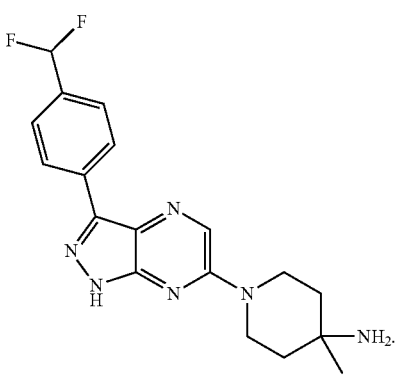
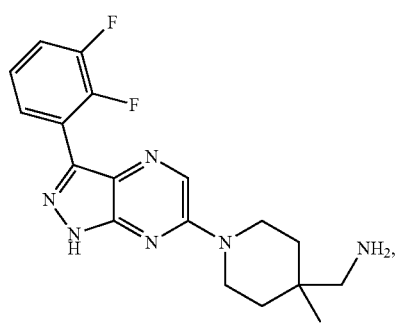 [SMILES: CC1(CN)CCN(c2cnc3c(-c4cccc(Cl)c4Br)n[nH]c3n2)CC1]

6. A pharmaceutical composition comprising a compound of claim 1 and a pharmaceutically acceptable carrier.

7. A method of treating a disorder in a subject comprising administration of a therapeutically effective amount of the compound of claim 1, to a subject in need thereof, wherein the disorder is Noonan syndrome, neuroblastoma, melanoma, acute myeloid leukemia, chronic myelomonocytic leukemia, juvenile myelomonocytic leukemia, breast cancer, lung cancer, or colorectal cancer.

8. The method of claim 7, further comprising administration of a therapeutically effective amount of an antibody, an antibody-drug conjugate, an immunomodulator, or a histone deacetylase inhibitor.

\* \* \* \* \*

UNITED STATES PATENT AND TRADEMARK OFFICE
CERTIFICATE OF CORRECTION

Page 1 of 1

PATENT NO. : 11,529,347 B2
APPLICATION NO. : 16/335933
DATED : December 20, 2022
INVENTOR(S) : Brian K. Albrecht et al.

It is certified that error appears in the above-identified patent and that said Letters Patent is hereby corrected as shown below:

In the Claims

In Claim 1, Column 126, Lines 43-49:
The second instance of " 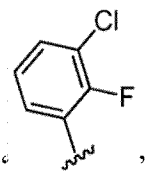 " should be changed to -- 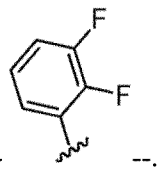 --.

In Claim 1, Column 128, Line 9:
"$R^g$" should be changed to -- $R^8$ --.

In Claim 3, Column 128, Line 29:
"H, -($C_1$-$C_3$)alkyl" should be changed to -- H or -($C_1$-$C_3$)alkyl --.

Signed and Sealed this
Twenty-sixth Day of September, 2023

Katherine Kelly Vidal
*Director of the United States Patent and Trademark Office*